US010433733B2

(12) United States Patent
Wang et al.

(10) Patent No.: US 10,433,733 B2
(45) Date of Patent: Oct. 8, 2019

(54) SINGLE-CELL LABEL-FREE PHOTOACOUSTIC FLOWOXIGRAPHY IN VIVO

(71) Applicant: Washington University, St. Louis, MO (US)

(72) Inventors: Lihong Wang, St. Louis, MO (US); Lidai Wang, St. Louis, MO (US); Konstantin Maslov, St. Louis, MO (US)

(73) Assignee: Washington University, St. Louis, MO (US)

( * ) Notice: Subject to any disclaimer, the term of this patent is extended or adjusted under 35 U.S.C. 154(b) by 63 days.

(21) Appl. No.: 15/148,685

(22) Filed: May 6, 2016

(65) Prior Publication Data

US 2016/0249812 A1 Sep. 1, 2016

Related U.S. Application Data

(60) Continuation of application No. 14/950,189, filed on Nov. 24, 2015, now abandoned, and a continuation of
(Continued)

(51) Int. Cl.
*A61B 8/00* (2006.01)
*A61B 5/00* (2006.01)
(Continued)

(52) U.S. Cl.
CPC .......... *A61B 5/0095* (2013.01); *A61B 5/0059* (2013.01); *A61B 5/0068* (2013.01);
(Continued)

(58) Field of Classification Search
CPC . A61B 5/0095; A61B 5/0068; A61B 5/14546; A61B 5/14542; A61B 5/4848;
(Continued)

(56) References Cited

U.S. PATENT DOCUMENTS 4,029,756 A 6/1977 Gaafar
4,127,318 A 11/1978 Determann et al.
(Continued)

FOREIGN PATENT DOCUMENTS

EP 0012262 A1 6/1980
EP 1493380 A1 1/2005
(Continued)

OTHER PUBLICATIONS

Zhang et al., "In vivo imaging of subcutaneous structures using functional photoacoustic microscopy," Nature Protocols, 2(4): 797-804 (2007).
(Continued)

*Primary Examiner* — Sanjay Cattungal
(74) *Attorney, Agent, or Firm* — Armstrong Teasdale LLP

(57) ABSTRACT

A method for obtaining a 3-D OR-PAM image of microvasculature within a region of interest of a subject is provided. The method includes: focusing a first light pulse at a first depth beneath a first surface position within the region of interest; receiving a first PA signal in response to the first light pulse; focusing a second light pulse at a second depth beneath the first surface position within the region of interest; receiving a second PA signal in response to the second light pulse; and forming the 3-D OR-PAM image by combining the first PA signal and the second PA signal.

18 Claims, 36 Drawing Sheets
(6 of 36 Drawing Sheet(s) Filed in Color)

Related U.S. Application Data application No. 14/164,117, filed on Jan. 24, 2014, now abandoned, said application No. 14/950,189 is a division of application No. 13/874,653, filed on May 1, 2013, now Pat. No. 9,226,666, said application No. 14/164,117 is a continuation-in-part of application No. 13/125,522, filed as application No. PCT/US2009/061435 on Oct. 21, 2009, now Pat. No. 9,528,966, said application No. 13/874,653 is a division of application No. 12/739,589, filed as application No. PCT/US2008/081167 on Oct. 24, 2008, now Pat. No. 8,454,512.

(60) Provisional application No. 61/756,092, filed on Jan. 24, 2013, provisional application No. 61/107,845, filed on Oct. 23, 2008, provisional application No. 60/982,624, filed on Oct. 25, 2007.

(51) Int. Cl.

| | | |
|---|---|---|
| *G01N 21/17* | (2006.01) | |
| *G01N 29/06* | (2006.01) | |
| *G01N 29/24* | (2006.01) | |
| *G02B 21/00* | (2006.01) | |
| *A61B 5/02* | (2006.01) | |
| *A61B 5/145* | (2006.01) | |
| *A61B 8/08* | (2006.01) | |
| *A61B 90/30* | (2016.01) | |

(52) U.S. Cl.
CPC ........ *A61B 5/0082* (2013.01); *A61B 5/02007* (2013.01); *A61B 5/14542* (2013.01); *A61B 5/14546* (2013.01); *A61B 5/444* (2013.01); *A61B 5/4848* (2013.01); *G01N 21/1702* (2013.01); *G01N 29/0681* (2013.01); *G01N 29/2418* (2013.01); *G02B 21/008* (2013.01); *G02B 21/0028* (2013.01); *A61B 8/485* (2013.01); *A61B 2090/306* (2016.02); *G01N 2291/02836* (2013.01); *G01N 2291/02872* (2013.01)

(58) Field of Classification Search
CPC ... A61B 5/444; A61B 5/02007; A61B 5/0082; A61B 5/0059; A61B 2090/306; A61B 8/485; G02B 21/0028; G02B 21/008; G01N 29/2418; G01N 29/0681; G01N 21/1702; G01N 2291/02872; G01N 2291/02836
USPC .................................................. 600/473–480
See application file for complete search history.

(56) References Cited

U.S. PATENT DOCUMENTS

| | | |
|---|---|---|
| 4,255,971 A | 3/1981 | Rosencwaig |
| 4,267,732 A | 5/1981 | Quate |
| 4,375,818 A | 3/1983 | Suwaki et al. |
| 4,385,634 A | 5/1983 | Bowen |
| 4,430,897 A | 2/1984 | Quate |
| 4,462,255 A | 7/1984 | Guess et al. |
| 4,468,136 A | 8/1984 | Murphy et al. |
| 4,489,727 A | 12/1984 | Matsuo et al. |
| 4,546,771 A | 10/1985 | Eggleton et al. |
| 4,596,254 A | 6/1986 | Adrian et al. |
| 5,373,845 A | 12/1994 | Gardineer et al. |
| 5,465,722 A | 11/1995 | Fort et al. |
| 5,713,356 A | 2/1998 | Kruger |
| 5,718,231 A | 2/1998 | Dewhurst et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | William et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1* | 4/2003 | Stern .................. G02B 21/0048 250/216 |
| 6,564,087 B1 | 5/2003 | Pitris et al. |
| 6,567,688 B1 | 5/2003 | Wang |
| 6,626,834 B2 | 9/2003 | Dunne et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1* | 10/2009 | Winchester, Jr. .... A61B 5/0059 600/407 |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |
| 2001/0052979 A1 | 12/2001 | Treado et al. |
| 2002/0093637 A1* | 7/2002 | Yuan .................... F16F 7/1005 355/72 |
| 2002/0176092 A1 | 11/2002 | Deck |
| 2003/0097066 A1 | 5/2003 | Shelby et al. |
| 2004/0039379 A1 | 2/2004 | Viator et al. |
| 2004/0082070 A1 | 4/2004 | Jones et al. |
| 2004/0254474 A1 | 12/2004 | Seibel et al. |
| 2005/0015002 A1 | 1/2005 | Dixon et al. |
| 2005/0154313 A1 | 7/2005 | Desilets et al. |
| 2005/0217381 A1 | 10/2005 | Falk |
| 2005/0234315 A1* | 10/2005 | Mayevsky ........... A61B 5/0059 600/310 |
| 2006/0122516 A1 | 6/2006 | Schmidt et al. |
| 2006/0181791 A1 | 8/2006 | Van Beek et al. |
| 2006/0184042 A1 | 8/2006 | Wang et al. |

(56) References Cited

U.S. PATENT DOCUMENTS

| | | | |
|---|---|---|---|
| 2006/0235299 | A1 | 10/2006 | Martinelli |
| 2007/0088206 | A1 | 4/2007 | Peyman et al. |
| 2007/0093702 | A1 | 4/2007 | Yu et al. |
| 2007/0213590 | A1 | 9/2007 | Squicciarini |
| 2007/0213618 | A1 | 9/2007 | Li et al. |
| 2007/0213693 | A1* | 9/2007 | Plunkett .................. A61F 9/008 606/6 |
| 2008/0029711 | A1* | 2/2008 | Viellerobe ......... G01N 21/6428 250/459.1 |
| 2008/0173093 | A1 | 7/2008 | Wang et al. |
| 2009/0088631 | A1 | 4/2009 | Dietz et al. |
| 2009/0116518 | A1 | 5/2009 | Patel et al. |
| 2010/0245766 | A1 | 9/2010 | Zhang et al. |
| 2010/0245769 | A1 | 9/2010 | Zhang et al. |
| 2010/0245770 | A1 | 9/2010 | Zhang et al. |
| 2010/0249562 | A1 | 9/2010 | Zhang et al. |
| 2010/0268042 | A1* | 10/2010 | Wang .................. A61B 5/0059 600/322 |
| 2010/0309466 | A1 | 12/2010 | Lucassen et al. |
| 2011/0201914 | A1 | 8/2011 | Wang et al. |
| 2011/0282181 | A1 | 11/2011 | Wang et al. |
| 2011/0282192 | A1 | 11/2011 | Axelrod et al. |
| 2014/0142404 | A1 | 5/2014 | Wang et al. |

FOREIGN PATENT DOCUMENTS

| | | |
|---|---|---|
| JP | 2000292416 A | 10/2000 |
| JP | 2009068977 A | 4/2009 |
| JP | 2010017426 A | 1/2010 |
| WO | 2006111929 A1 | 10/2006 |
| WO | 2007088709 A1 | 8/2007 |
| WO | 2007148239 A2 | 12/2007 |
| WO | 2008062354 A1 | 5/2008 |
| WO | 2008100386 A2 | 8/2008 |
| WO | 2009055705 A2 | 4/2009 |
| WO | 2010048258 A1 | 4/2010 |
| WO | 2010080991 A2 | 7/2010 |
| WO | 2011091360 A2 | 7/2011 |
| WO | 2011127428 A2 | 10/2011 |
| WO | 2013086293 A1 | 6/2013 |

OTHER PUBLICATIONS

Zharov et al., "In vivo photoacoustic flow cytometry for monitor of circulating single cancer cells and contrast agents," Optics Letters, 31(24): 3623-3625 (2006).

Zou et al., "BOLD response to visual stimulation in survivors of childhood cancer," NeuroImage, 24(1): 61-69 (2005).

International Search Report and Written Opinion from Application Serial No. PCT/US2008/081167, dated Apr. 22, 2009 (7 pages).

International Search Report and Written Opinion from Application Serial No. PCT/US2009/061435, dated Mar. 29, 2010 (10 pages).

International Search Report and Written Opinion from Application Serial No. PCT/US2010/020488, dated Aug. 31, 2010 (10 pages).

International Search Report and Written Opinion from Application Serial No. PCT/US2011/022253, dated Sep. 22, 2011 (8 pages).

International Search Report and Written Opinion from Application Serial No. PCT/US2011/031823, dated Dec. 26, 2011 (8 pages).

International Search Report and Written Opinion from Application Serial No. PCT/US2012/068403, dated Mar. 19, 2013 (10 pages).

Extended European Search Report from European Application Serial No. 08842292.8, dated Dec. 17, 2013 (8 pages).

Office Action from related U.S. Appl. No. 11/625,099, dated Nov. 1, 2010 (11 pages).

Office Action from related U.S. Appl. No. 11/625,099, dated Apr. 20, 2010 (11 pages).

Office Action from related U.S. Appl. No. 12/254,643, dated Aug. 6, 2010 (9 pages).

Notice of Allowance from related U.S. Appl. No. 12/254,643, dated Nov. 22, 2010 (8 pages).

Office Action from related U.S. Appl. No. 12/568,069, dated Dec. 21, 2012 (10 pages).

Office Action from related U.S. Appl. No. 12/568,069, dated Mar. 29, 2012 (10 pages).

Office Action from related U.S. Appl. No. 12/568,069, dated Sep. 18, 2012 (14 pages).

Notice of Allowance from related U.S. Appl. No. 12/568,069, dated Feb. 22, 2013 (7 pages).

Office Action from related U.S. Appl. No. 12/739,589, dated Jul. 19, 2012 (9 pages).

Notice of Allowance from related U.S. Appl. No. 12/739,589, dated Feb. 5, 2013 (9 pages).

Office Action from related U.S. Appl. No. 13/125,522, dated Jan. 22, 2013 (8 pages).

Office Action from related U.S. Appl. No. 13/125,522, dated May 23, 2013 (10 pages).

Office Action from related U.S. Appl. No. 13/125,522, dated Jul. 17, 2014 (10 pages).

Office Action from related U.S. Appl. No. 13/125,522, dated Oct. 29, 2014 (10 pages).

Office Action from related U.S. Appl. No. 13/143,832, dated Apr. 18, 20914 (14 pages).

Office Action from related U.S. Appl. No. 13/369,558, dated Jun. 20, 2014 (10 pages).

Notice of Allowance from related U.S. Appl. No. 13/369,558, dated Jul. 29, 2014 (7 pages).

Office Action from related U.S. Appl. No. 13/450,793, dated Jun. 5, 2013 (20 pages).

Office Action from related U.S. Appl. No. 13/450,793, dated Nov. 22, 2013 (22 pages).

Office Action from related U.S. Appl. No. 13/450,793, dated Mar. 24, 2014 (22 pages).

Office Action from related U.S. Appl. No. 13/450,793, dated Aug. 1, 2014 (21 pages).

Office Action from related U.S. Appl. No. 13/574,994, dated Mar. 17, 2014 (9 pages).

Office Action from related U.S. Appl. No. 13/574,994, dated Aug. 26, 2014 (10 pages).

Office Action from related U.S. Appl. No. 13/637,897, dated Aug. 1, 2014 (7 pages).

Office Action from related U.S. Appl. No. 14/164,117, dated Dec. 11, 2015 (18 pages).

Final Office Action from related Japanese Patent Application No. 2010-531281, dated Mar. 11, 2014, (5 pages).

Murray et al., "High-sensitivity laser-based acoustic microscopy using a modulated excitation source," Applied Physics Letters, 85(14): 2974-2976 (2004).

Niakajima et al., "Three-dimensional analysis and classification of arteries in the skin and subcutaneous adipofascial tissue by computer graphics imaging," Plastic and Reconstructive Surgery, 102(3): 749-760 (1998).

Nelson et al., "Imaging gliblastoma multiforme," Cancer Journal, 9(2): 134-145 (2003).

Niederhauser et al., "Combined Ultrasound and Optoacoustic System for Real-Time High-Contrast Vascular Imaging in Vivo," IEEE Transactions on Medical Imaging, 24(4): 436-440 (2005).

Oraevsky et al., "Laser Optoacoustic Tomography of Layered Tissues: Signal Processing," Proceedings of SPIE, 2979: 59-70 (1997).

Oraevsky et al., "Ultimate Sensitivity of Time-Resolved Opto-Acoustic Detection," In Biomedical Optoacoustics, Proceedings of SPIE, 3916: 228-239 (2000).

Oraevsky et al., "Optoacoustic Tomography," Biomedical Photonics Handbook, CRC Press LLC, USA, pp. 1-40 (2003).

Oraevsky et al., "Laser opto-acoustic imaging of the breast: detection of cancer angiogenesis," Proceedings of SPIE, 3597: 352-363 (1999).

Petrov et al., "Optoacoustic, Noninvasive, Real-Time, Continuous Monitoring of Cerebral Blood Oxygenation: An In Vivo Study in Sheep," Anesthesiology, 102(1): 69-75 (2005).

Potter et al., "Capillary diameter and geometry in cardiac and skeletal muscle studied by means of corrosion casts," Microvascular Research, 25(1): 68-84 (1983).

(56) References Cited

OTHER PUBLICATIONS

Robert et al., "Fabrication of focused poly (vinylidene fluoride-trifluoroethylene) P (VDF-TrFE) copolymer 40-50 MHz ultrasound transducers on curved surfaces," Journal of Applied Physics, 96(1): 252-256 (2004).
Saager et al., "Direct characterization and removal of interfering absorption trends in two-layer turbid media," Journal of the Optical Society of America A, 22(9): 1874-1882 (2005).
Savateeva et al., "Noninvasive detection and staging of oral cancer in vivo with confocal optoacoustic tomography," Proceedings of SPIE, 3916: 55-66 (2000).
Schmidt et al., "A 32-channel time-resolved instrument for medical optical tomography," Review of Scientific Instruments, 71(1): 256-265 (2000).
Schroeter et al., "Spontaneous slow hemodynamic oscillations are impaired in cerebral microangiopathy," Journal of Cerebral Blood Flow & Metabolism, 25(12): 1675-1684 (2005).
Sethuraman et al., "Development of a combined intravascular ultrasound and photoacoustic imaging system," Proceedings of SPIE, 6086: 60860F.1-60860F.10 (2006).
Sethuraman et al., "Intravascular photoacoustic imaging of atherosclerotic plaques: ex vivo study using a rabbit model of atherosclerosis," Proceedings of SPIE, 6437: 643729.1-643729.9 (2007).
Sheth et al., "Columnar Specificity of Microvascular Oxygenation and Volume Responses: Implications for Functional Brain Mapping," Journal of Neuroscience, 24(3): 634-641 (2004).
Shmueli et al., "Low-frequency fluctuations in the cardiac rate as a source of variance in the resting-state fMRI BOLD signal," NeuroImage, 38(2): 306-320 (2007).
Siphanto et al., "Imaging of Small Vessels Using Photoacoustics: An In Vivo Study," Lasers in Surgery and Medicine, 35(5): 354-362 (2004).
Song et al., "Fast 3-D dark-field reflection-mode photoacoustic microscopy in vivo with a 30-MHz ultrasound linear array," Journal of Biomedical Optics, 13(5): 054028.1-054028.5 (2008).
Song et al., "Section-illumination photoacoustic microscopy for dynamic 3D imaging of microcirculation in vivo," Optics Letters, 35(9): 1482-1484 (2010).
Steinbrink et al., "Illuminating the BOLD signal: combined fMRI-fNIRS studies," Magnetic Resonance Imaging, 24(4): 495-505 (2006).
Stern, MD., "In vivo evaluation of microcirculation by coherent light scattering," Nature, 254(5495): 56-58 (1975).
Tam, A.C., "Applications of photoacoustic sensing techniques," Reviews of Modern Physics, 58(2): 381-431 and Figs. 16, 26 and 32 (1986).
Tearney et al., "Scanning single-mode fiber optic catheter-endoscope for optical coherence tomography," Optics Letters, 21(7): 543-545 (1996).
Tran et al., "In vivo endoscopic optical coherence tomography by use of a rotational microelectromechanical system probe," Optics Letters, 29(11): 1236-1238 (2004).
Van Essen et al., "An Integrated Software Suite for Surface-based Analyses of Cerebral Cortex," Journal of the American Medical Informatics Association, 8(5): 443-459 (2001).
Viator et al., "Design and testing of an endoscopic photoacoustic probe for determination of treatment depth after photodynamic therapy," Proceedings of SPIE in Biomedical Optoacoustics II, 4256: 16-27 (2001).
Wang et al., "Ballistic 2-D Imaging Through Scattering Walls Using an Ultrafast Optical Kerr Gate," Science, 253(5021): 769-771 (1991).
Wang et al., "MCML—Monte Carlo modeling of light transport in multi-layered tissues," Computer Methods and Programs in Biomedicine, 47(2): 131-146 (1995).
Wang et al., "Noninvasive laser-induced photoacoustic tomography for structural and functional in vivo imaging of the brain," Nature Biotechnology, 21(7): 803-806 (2003).
Wang et al., "Three-dimensional laser-induced photoacoustic tomography of mouse brain with the skin and skull intact," Optics Letters, 28(19): 1739-1741 (2003).
Wang et al., "Noninvasive photoacoustic angiography of animal brains in vivo with near-infrared light and an optical contrast agent," Optics Letters, 29(7): 730-732 (2004).
Wang et al., "Biomedical Optics, Principles and Imaging," 2007, Wiley-Interscience, A John Wiley & Sons, Inc., Hoboken, New Jersey, US (7 pages).
Wang, L. V., "Multiscale photoacoustic microscopy and computed tomography," Nature Photonics, 3(9): 503-509 (2009).
Wang et al., "Intravascular Photoacoustic Imaging", IEEE J Quantum Electronics, 16(3): 588-599 (2010).
Xu et al., "Photoacoustic imaging in biomedicine," Review of Scientific Instruments, 77(4): 041101.1-041101.22 (2006).
Xu et al., "Time Reversal Ultrasound Modulated Optical Tomography Using a BSO Phase Conjugate Mirror," poster presented at SPIE Conference 7177 on Jan. 26, 2009; 3 pgs.
Yadlowsky et al., "Multiple scattering in optical coherence microscopy," Applied Optics, 34(25): 1699-5707 (1995).
Yang et al., "Optical coherence and Doppler tomography for monitoring tissue changes induced by laser thermal therapy—An in vivo feasibility study," Review of Scientific Instruments, 74(1): 437-440 (2003).
Yang et al., "Novel biomedical imaging that combines intravascular ultrasound (IVUS) and optical coherence tomography (OCT)," IEEE International Ultrasonics Symposium, Beijing, China, Nov. 2-5, 2008, pp. 1769-1772.
Yao et al., "Monte Carlo simulation of an optical coherence tomography signal in homogeneous turbid media," Physics in Medicine & Biology, 44(9): 2307-2320 (1999).
Yaqoob et al., "Methods and application areas of endoscopic optical coherence tomography," Journal of Biomedical Optics, 11(6): 063001.1-063001.19 (2006).
Yodh et al., "Spectroscopy and Imaging With Diffusing Light," Physics Today, 48(3): 34-40 (1995).
Yodh et al., "Functional Imaging with Diffusing Light," Biomedical Photonics Handbook, 2003, Chapter 21, CRC Press, Boca Raton (45 pgs).
Zeff et al., "Retinotopic mapping of adult human visual cortex with high-density diffuse optical tomography," Proceedings of the National Academy of Sciences, 104(29): 12169-12174 (2007).
Zemp et al., "Realtime photoacoustic microscopy in vivo with a 30-MHz ultrasonic array transducer," Optics Express, 16(11): 7915-7928 (2008).
Zhang et al., "Intrinsic Functional Relations Between Human Cerebral Cortex and Thalamus," J Neurophysiology, 100(4): 1740-1748 (2008).
Zhang et al., "Functional photoacoustic microscopy for high-resolution and noninvasive in vivo imaging," Nature Biotechnology, 24(7): 848-851 (2006).
Ai et al., "Spectral-domain optical coherence tomography: Removal of autocorrelation using an optical switch," Applied Physics Letters, 88(11): 111115-1 to 111115-3 (2006).
Allen et al., "Pulsed near-infrared laser diode excitation system for biomedical photoacoustic imaging," Optics Letters, 31(23): 3462-3464 (2006).
Bell, Alexander Graham "On the Production and Reproduction of Sound by Light," American Journal of Sciences, Third Series, 20(118): 305-324 (1880).
Calasso et al., "Photoacoustic Point Source," Physical Review Letters, 86(16): 3550-3553 (2001).
Cannata et al., "Development of a 35-MHz Piezo-Composite Ultrasound Array for Medical Imaging," IEEE Transactions on Ultrasonics, Ferroelectrics, and Frequency Control, 53(1): 224-236 (2006).
Cheong et al., "A review of the optical properties of biological tissues," IEEE J. Quantum Electronics, 26(12): 2166-2185 (1990).
D'Andrea et al., "Time-resolved optical imaging through turbid media using a fast data acquisition system based on a gated CCD camera," Journal of Physics D: Applied Physics, 36(14): 1675-1681 (2003).

(56) References Cited

OTHER PUBLICATIONS

De Boer et al., "Improved signal-to-noise ratio in spectral-domain compared with time-domain optical coherence tomography," Optics Letters, 28(21): 2067-2069 (2003).
Diebold et al., "Photoacoustic "Signatures" of Particulate Matter: Optical Production of Acoustic Monopole Radiation," Science, 250(4977): 101-104 (1990).
Diebold et al., "Photoacoustic Monopole Radiation in One, Two, and Three Dimensions," Physical Review Letters, 67(24): 3384-3387 and Figs. 1 and 2 (1991).
Dunn et al., "Transport-based image reconstruction in turbid media with small source-detector separations," Optics Letters, 25(24): 1777-1779 (2000).
Ermilov et al., "Laser optoacoustic imaging system for detection of breast cancer," Journal of Biomedical Optics, 14(2): 024007-024007-14 (2009).
Erpelding et al., "Sentinel Lymph Nodes in the Rat: Noninvasive Photoacoustic and US Imaging with a Clinical US System," Radiology, 256(1): 102-110 (2010).
Fan et al., "Development of a laser photothermoacoustic frequency-swept system for subsurface imaging: Theory and experiment," Journal of Acoustical Society of America, 116(6): 3523-3533 (2004).
Fang et al., "Photoacoustic Doppler Effect from Flowing Small Light-Absorbing Particles," Physical Review Letters, 99(18): 184501-184501-4 (2007).
Fercher et al., "Measurement of intraocular distances by backscattering spectral interferometry," Optics Communications, 117(1-2): 43-48 (1995).
Foster et al., "Advances in Ultrasound Biomicroscopy," Ultrasound in Medicine and Biology, 26(1): 1-27 (2000).
Gibson et al., "Recent advances in diffuse optical imaging," Physics in Medicine and Biology, 50(4): R1-R43, (2005).
Guittet et al., "In vivo high-frequency ultrasonic characterization of human dermis," IEEE Transactions on Biomedical Engineering, 46(6): 740-746 (1999).
Hebden et al., "Enhanced time-resolved imaging with a diffusion model of photon transport," Optics Letters, 19(5): 311-313 (1994).
Hee et al., "Femtosecond transillumination tomography in thick tissues," Optics Letters, 18(13): 1107-1109 (1993).
Hillman et al., "Laminar optical tomography: demonstration of millimeter-scale depth-resolved imaging in turbid media," Optics Letters, 29(14): 1650-1652 (2004).
Hoelen et al., "Three-dimensional photoacoustic imaging of blood vessels in tissue," Optics Letters, 23(8): 648-650 (1998).
Hu et al., "Label-free photoacoustic ophthalmic angiography," Optics Letters, 35(1): 1-3 (2010).
Huang et al., "Optical Coherence Tomography," Science, New Series, 254(5035): 1178-1181 (1991).
Huber et al., "Three-dimensional and C-mode OCT imaging with a compact, frequency swept laser source at 1300 nm," Optics Express, 13(26): 10523-10538 (2005).
Karamata et al., "Multiple scattering in optical coherence tomography. I. Investigation and modeling," Journal Optical Society of America, 22(7): 1369-1379 (2005).
Kim et al., "In Vivo Molecular Photoacoustic Tomography of Melanomas Targeted by Bioconjugated Gold Nanocages," ACS Nano, 4(8): 4559-4564 (2010).
Kolkman et al., "In vivo photoacoustic imaging of blood vessels using an extreme-narrow aperture sensor," IEEE Journal on Selected Topics in Quantum Electronics, 9(2): 343-346 (2003).
Kruger et al., "Photoacoustic ultrasound (PAUS)—Reconstruction tomography," Medical Physics, 22(10): 1605-1609 (1995).
Kruger et al., "Thermoacoustic computed tomography—technical considerations," Medical Physics, 26(9): 1832-1837 (1999).
Kruger et al., "Breast Cancer in Vivo: Contrast Enhancement with Thermoacoustic CT at 434 MHz—Feasibility Study," Radiology, 216(1): 279-283 (2000).
Kruger et al., "Thermoacoustic computed tomography using a conventional linear transducer array," Medical Physics, 30(5): 856-860 (2003).
Kruger et al., "Thermoacoustic Molecular Imaging of Small Animals," Molecular Imaging, 2(2): 113-123 (2003).
Ku et al., "Scanning thermoacoustic tomography in biological tissue," Medical Physics, 27(5): 1195-1202 (2000).
Ku et al., "Scanning microwave-induced thermoacoustic tomography: Signal, resolution, and contrast," Medical Physics, 28(1): 4-10 (2001).
Ku et al., "Multiple-bandwidth photoacoustic tomography," Physics in Medicine & Biology, 49(7): 1329-1338 (2004).
Ku et al., "Deeply penetrating photoacoustic tomography in biological tissues enhanced with an optical contrast agent," Optics Letters, 30(5): 507-509 (2005).
Ku et al., "Imaging of tumor angiogenesis in rat brains in vivo by photoacoustic tomography," Applied Optics, 44(5): 770-775 (2005).
Ku et al., "Thermoacoustic and Photoacoustic Tomography of Thick Biological Tissues Toward Breast Imaging," Technology in Cancer Research & Treatment, 4(5): 559-566 (2005).
Leitgeb et al., "Performance of fourier domain vs. time domain optical coherence tomography," Optics Express, 11(8): 889-894 (2003).
Li et al., "Optical coherence computed tomography," Applied Physics Letters, 91(14): 141107-141107-3 (2007).
Li et al., "Simultaneous Molecular and Hypoxia Imaging of Brain Tumors In Vivo Using Spectroscopic Photoacoustic Tomography," Proceedings of the IEEE, 96(3): 481-489 (2008).
Manohar et al., "Initial Results of in vivo non-invasive cancer imaging in the human breast using near-infrared photoacoustics," Optics Express, 15(19): 12277-12285 (2007).
Maslov et al., "Photoacoustic imaging of biological tissue with intensity-modulated continuous-wave laser," Journal of Biomedical Optics, 13(2): 024006-024006-5 (2008).
Maslov et al., "Optical-resolution photoacoustic microscopy for in vivo imaging of single capillaries," Optical Letters, 33(9): 929-931 (2008).
Maslov et al., "In vivo dark-field reflection-mode photoacoustic microscopy," Optics Letters, 30(6): 625-627 (2005).
Mishra et al., "Development and comparison of the DTM, the DOM and the FVM formulations for the short-pulse laser transport through a participating medium," International Journal of Heat & Mass Transfer, 49(11-12): 1820-1832 (2006).
Morgner et al., "Spectroscopic optical coherence tomography," Optics Letters, 25(2) 111-113 (2000).
Partial European Search Report issued for European Application No. 17159220.7, dated Aug. 23, 2017 (10 pages).

* cited by examiner

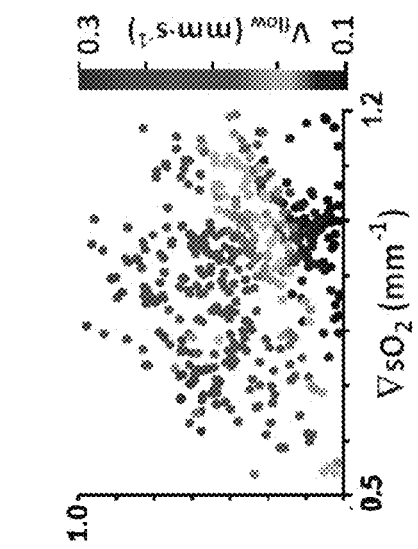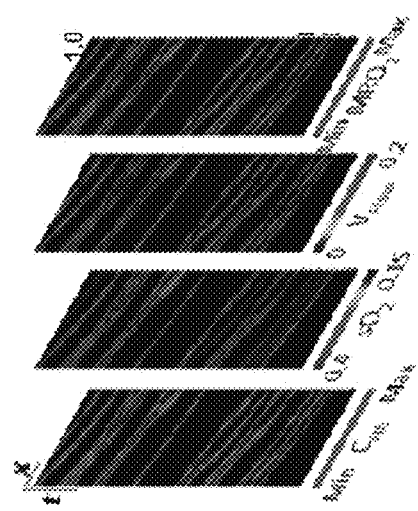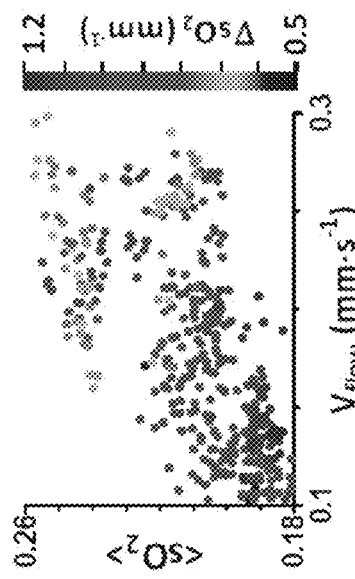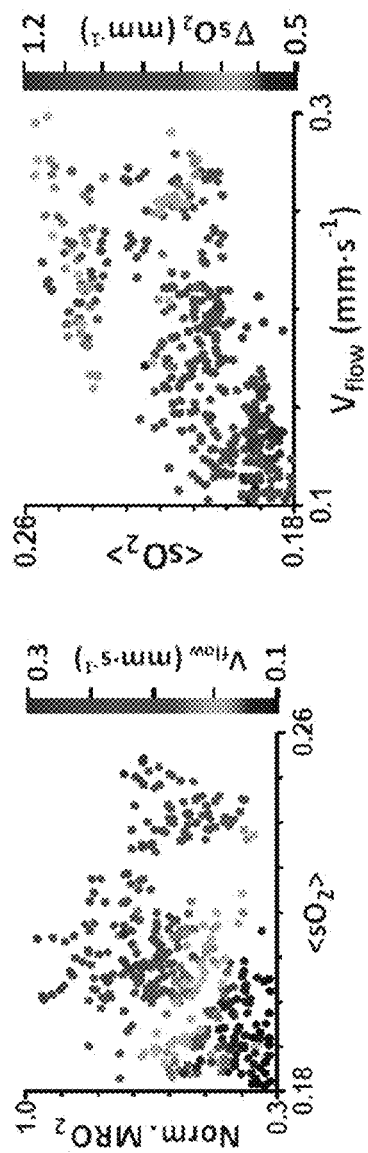
FIG. 15A
FIG. 15B
FIG. 15C
FIG. 15D
FIG. 15E

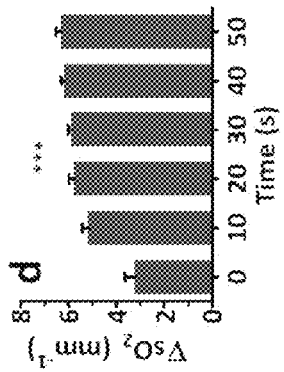
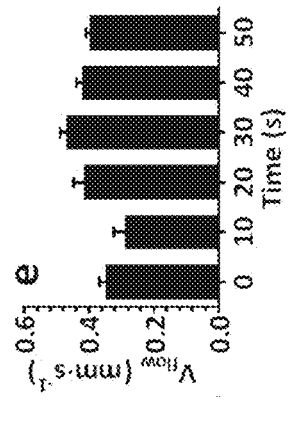
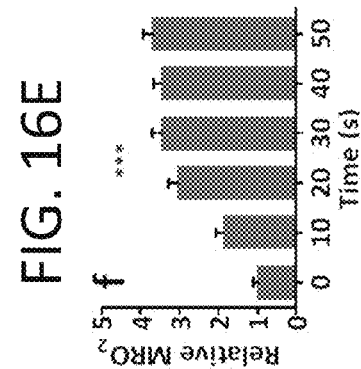
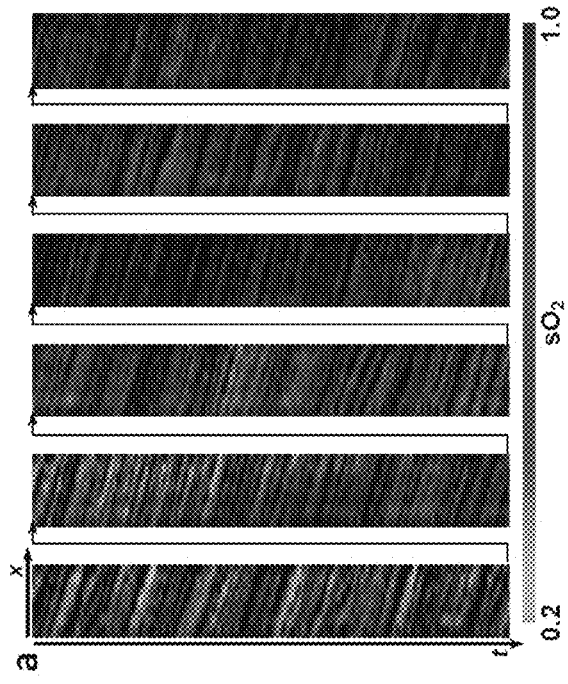
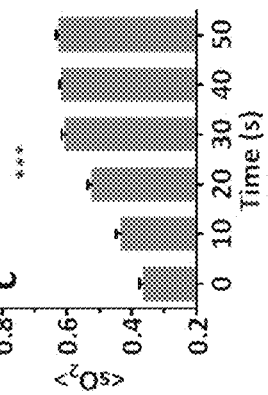
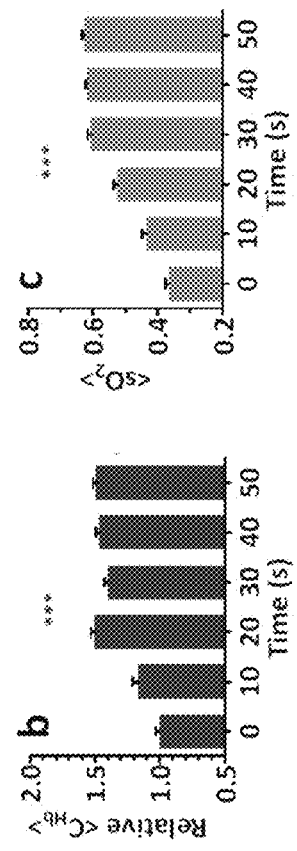
FIG. 16A
FIG. 16B
FIG. 16C
FIG. 16D
FIG. 16E
FIG. 16F

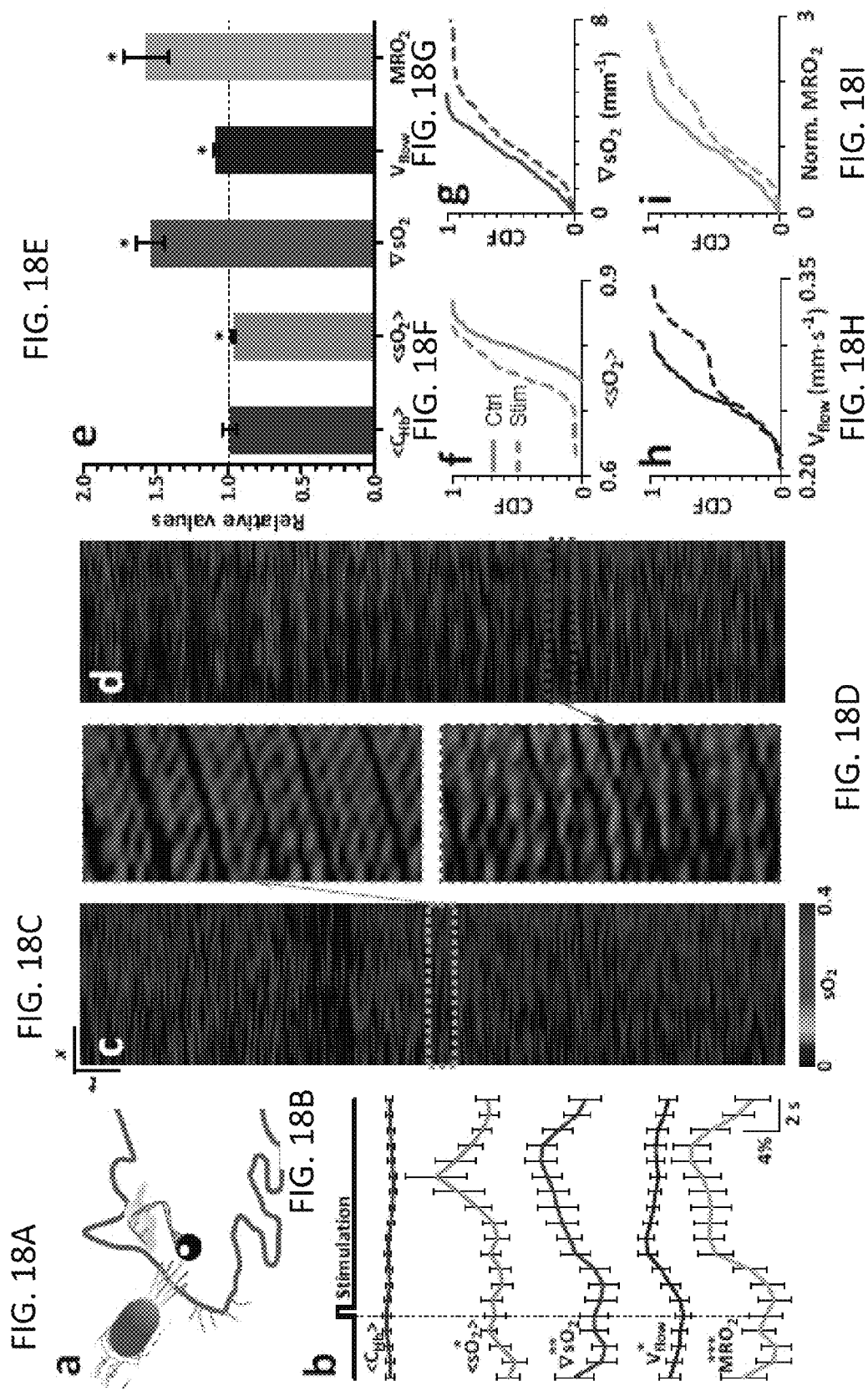

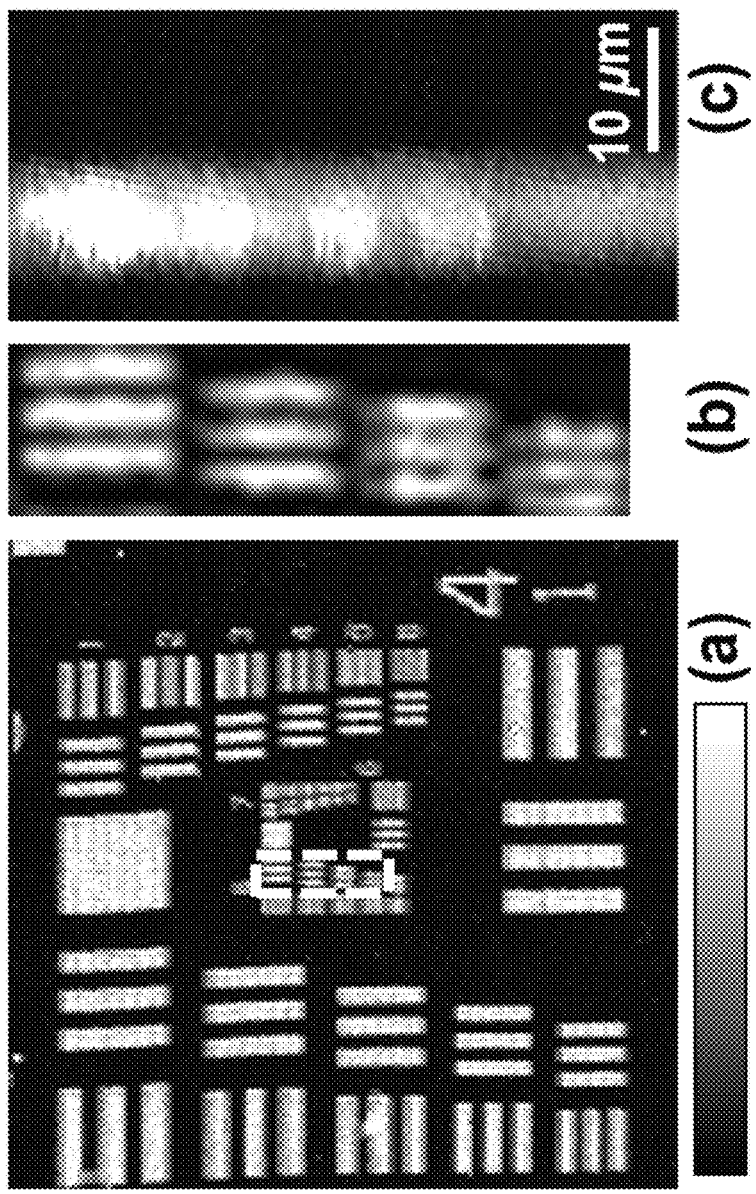

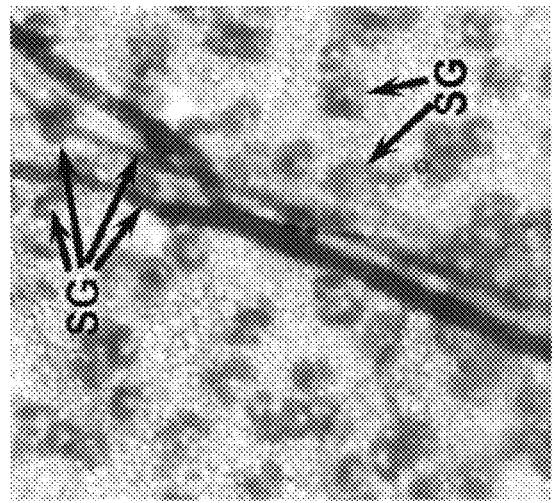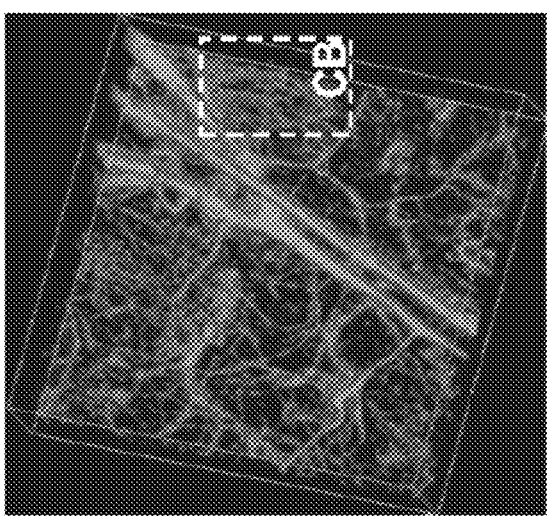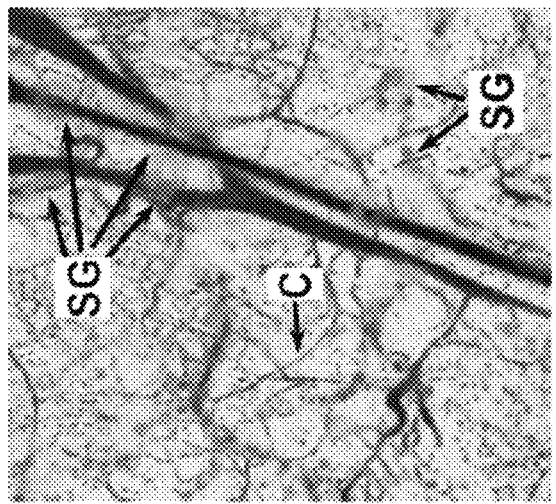
FIG. 34A  FIG. 34B  FIG. 34C

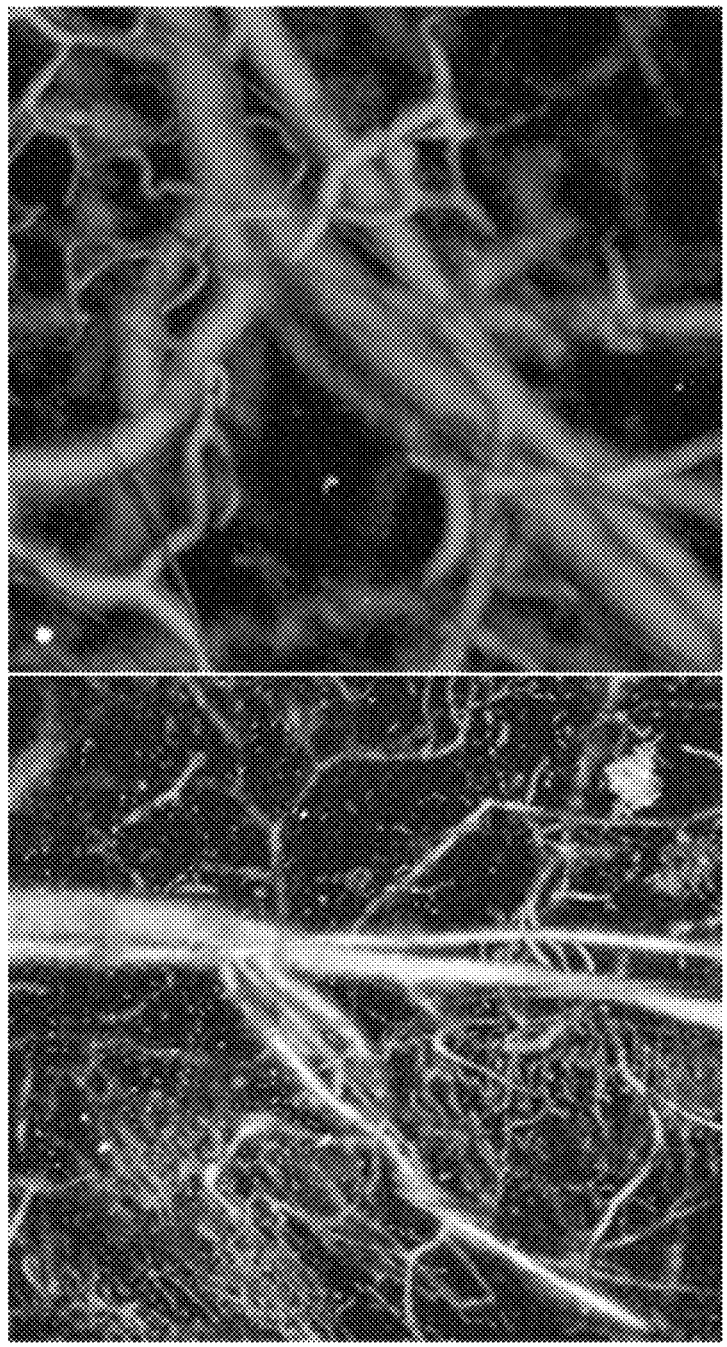

SINGLE-CELL LABEL-FREE PHOTOACOUSTIC FLOWOXIGRAPHY IN VIVO

CROSS REFERENCE TO RELATED APPLICATIONS

This application is a continuation of U.S. patent application Ser. No. 14/950,189 filed Nov. 24, 2015, which is a divisional of U.S. patent application Ser. No. 13/874,653 filed May 1, 2013 (now U.S. Pat. No. 9,226,666), which is a divisional of U.S. patent application Ser. No. 12/739,589 filed Jun. 28, 2010 (now U.S. Pat. No. 8,454,512), which is a U.S. National Phase Patent Application of International Application Serial No. PCT/US2008/081167 filed Oct. 24, 2008, which claims priority to U.S. Provisional Patent Application No. 60/982,624 filed Oct. 25, 2007, of which all disclosures are hereby incorporated by reference in their entirety.

This application is also a continuation of U.S. patent application Ser. No. 14/164,117 filed Jan. 24, 2014, which is a continuation-in-part of U.S. patent application Ser. No. 13/125,522 filed on Apr. 21, 2011, which is a U.S. National Phase Patent Application of International Application Serial No. PCT/US2009/061435 filed on Oct. 21, 2009, which claims priority to U.S. Provisional Application No. 61/107,845 filed on Oct. 23, 2008, of which all disclosures are hereby incorporated by reference in their entirety. U.S. patent application Ser. No. 14/164,117 further claims priority to U.S. Provisional Application No. 61/756,092 filed on Jan. 24, 2013, the disclosure of which is also hereby incorporated by reference in its entirety.

STATEMENT REGARDING FEDERALLY SPONSORED RESEARCH & DEVELOPMENT

This invention was made with government support under grants R01 EB000712 and R01 NS46214, both awarded by the U.S. National Institutes of Health. The government has certain rights in the invention.

COLOR DRAWINGS

The patent or application file contains at least one drawing executed in color. Copies of this patent or patent application publication with color drawing(s) will be provided by the Office upon request and payment of the necessary fee.

BACKGROUND

The subject matter disclosed herein relates generally to photoacoustic imaging and, more specifically, to using photoacoustic tomography to characterize a target or targeted area within a tissue.

Moreover, the field of the invention relates generally to noninvasive imaging and, more particularly, to imaging an area with an object using confocal photoacoustic imaging.

Most living cells require oxygen to metabolize nutrients into usable energy. In vivo imaging of oxygen transport and consumption at high spatial and temporal resolution is required to understand the metabolism of cells and related functionalities. Although individual parameters such as $sO_2$, partial oxygen pressure ($pO_2$), or blood flow speed ($V_{flow}$) may partially characterize tissue oxygenation, no single parameter can provide a comprehensive view of oxygen transport and consumption. To quantify the fundamental metabolic rate of oxygen ($MRO_2$), three primary imaging modalities have been employed in previous research: positron emission tomography (PET), functional magnetic resonance imaging (fMRI), and diffuse optical tomography (DOT). These three imaging modalities are capable of imaging $MRO_2$ at a millimeter-scale spatial resolution, but this resolution is inadequate to visualize $MRO_2$ at a single-cell resolution, at which many important oxygen transport and delivery processes occur.

Photoacoustic (PA) microscopy has been proposed to measure $MRO_2$ of a region at the feeding and draining blood vessels. However, this assessment of $MRO_2$ has been limited to a relatively large region due to the limitations of existing PA microscopy devices. As a result, the feeding and draining blood vessels—especially those surrounding a tumor—may be numerous and difficult to identify. Since micrometer-sized RBCs are the fundamental elements for delivering most of the oxygen to cells and tissues, there exists a need for direct functional imaging of flowing individual RBCs in real time.

The capability of noninvasively imaging capillaries, the smallest blood vessels, in vivo has long been desired by biologists at least because it provides a window to study fundamental physiological phenomena, such as neurovascular coupling, on a microscopic level. Existing imaging modalities, however, are unable to simultaneously provide sensitivity, contrast, and spatial resolution sufficient to noninvasively image capillaries.

BRIEF DESCRIPTION

In one aspect, a device for real-time spectral imaging of single moving red blood cells in a subject in vivo is provided. The device includes: an isosbestic laser to deliver a series of isosbestic laser pulses at an isosbestic wavelength, an isosbestic pulse width of less than 10 ns and an isosbestic pulse repetition rate of at least 2 kHz; a non-isosbestic laser to deliver a series of non-isosbestic laser pulses at a non-isosbestic wavelength, a non-isosbestic pulse width of less than 10 ns and a non-isosbestic pulse repetition rate of at least 2 kHz; an optical fiber to direct the series of isosbestic laser pulses and the series of non-isosbestic laser pulses to an optical assembly; and the optical assembly to focus the series of isosbestic laser pulses and the series of series of non-isosbestic laser pulses into a beam with a beam cross-sectional diameter of less than 10 μm through an optical focus region. Each isosbestic laser pulse is delivered at a pulse separation period of about 20 μs before or after each adjacent non-isosbestic laser pulse.

In another aspect, a system for real-time spectral imaging of single moving red blood cells in a subject in vivo is provided. The system includes: a dual wavelength light source module to produce a series of isosbestic laser pulses at an isosbestic wavelength, an isosbestic pulse width of less than 10 ns and an isosbestic pulse repetition rate of at least 2 kHz and a series of non-isosbestic laser pulses at a non-isosbestic wavelength, a non-isosbestic pulse width of less than 10 ns and a non-isosbestic pulse repetition rate of at least 2 kHz; and an optical module to direct the series of isosbestic laser pulses and the series of non-isosbestic laser pulses through an optical focus region in a cylindrical beam with a beam cross-sectional diameter of less than 10 μm. Each isosbestic laser pulse is delivered at a pulse separation period of about 20 μs before or after each adjacent non-isosbestic laser pulse.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure.

FIG. 15A is a series of images of single RBCs releasing oxygen in a capillary in a mouse brain obtained using a single red blood cell (RBC) photoacoustic flowoxigraphy (FOG) device; scale bars: x=10 µm, z=30 µm.

FIG. 15B includes a series of graphs summarizing simultaneous measurements of multiple functional parameters from the images of single RBCs, including total hemoglobin concentration ($C_{Hb}$), oxygen saturation ($sO_2$), flow speed ($V_{flow}$, unit: mm·s-1), and metabolic rate of oxygen ($MRO_2$).

FIG. 15C is a graph summarizing normalized $MRO_2$ versus $\nabla sO_2$ at various flow speeds within a vessel.

FIG. 15D is a graph summarizing normalized $MRO_2$ versus $<sO_2>$ at various flow speeds within a vessel; $<sO_2>$ denotes the $sO_2$ averaged over the capillary segment in the field of view.

FIG. 15E is a graph summarizing $<sO_2>$ as a function of $V_{flow}$ at various $\nabla sO_2$.

In FIGS. 15C, 15D, and 15E, each point on the graphs represents one measurement averaged over 1 s.

FIG. 16A is a series of images summarizing the dynamic imaging of single-RBC oxygen delivery under a transition from hypoxia to hyperoxia for 60 s as RBCs flow in the positive x-direction through a 30-µm capillary segment obtained using a single red blood cell (RBC) photoacoustic flowoxigraphy (FOG) device; each oblique line in the x-t images tracks one single RBC.

FIGS. 16B, 16C, 16D, 16E, and 16F are graphs summarizing $<C_{Hb}>$, $<sO_2>$, $\nabla sO_2$, $V_{flow}$, and $MRO_2$ averaged over 10 sec, respectively; error bars are SEM, p values were determined by two-way ANOVA tests, and *** indicates $p<0.001$.

FIG. 18A is a schematic of an experimental setup used for imaging of neuron-single-RBC coupling in mouse visual cortex using a single red blood cell (RBC) photoacoustic flowoxigraphy (FOG) device.

FIG. 18B is a series of graphs summarizing the transient responses of $sO_2$, $\nabla sO_2$, $V_{flow}$, and $MRO_2$ to a single visual stimulation; error bars denote SEMs, and * denotes $p<0.05$,  denotes $p<0.01$, and * denotes $p<0.001$ according to two-way ANOVA tests.

FIG. 18C is a MAP image of $sO_2$ obtained without continuous visual stimulations.

FIG. 18D is a MAP image of $sO_2$ obtained with 1 Hz continuous optical flashing stimulations on the left mouse eye. The scale bars in FIGS. 18C and 18D are x=10 µm and t=10 s.

FIG. 18E is a graph summarizing the relative changes of single RBC functional parameters ($<C_{Hb}>$, $<sO_2>$, $\nabla sO_2$, $V_{flow}$, and $MRO_2$) under continuous visual stimulation; all values are normalized to mean values of control images, error bars are SEMs, and * denotes $p<0.05$ according to two-way ANOVA tests.

FIGS. 18F, 18G, 18H, and 18I are graphs summarizing cumulative distribution functions (CDFs) of $<sO_2>$, $\nabla sO_2$, $V_{flow}$, and $MRO_2$, respectively under control (ctrl) and stimulation (stim) conditions; $MRO_2$ was normalized to the mean value of the control experiment.

FIGS. 32A, 32B, and 32C are images representing a lateral resolution measurement by the imaging system using a resolution test target immersed in clear liquid.

FIGS. 34A and 34B are photoacoustic images of a microvasculature by the imaging system.

FIG. 34C is a photograph of the microvasculature of FIGS. 34A and 34B, taken from a transmission microscope.

FIG. 36A is an in vivo image of a capillary bed captured using the imaging system.

FIG. 36B is an in vivo image of multiple levels of blood vessel bifurcations captured using the imaging system.

Corresponding reference characters and labels indicate corresponding elements among the views of the drawings. The headings used in the figures should not be interpreted to limit the scope of the claims.

Figure 1:
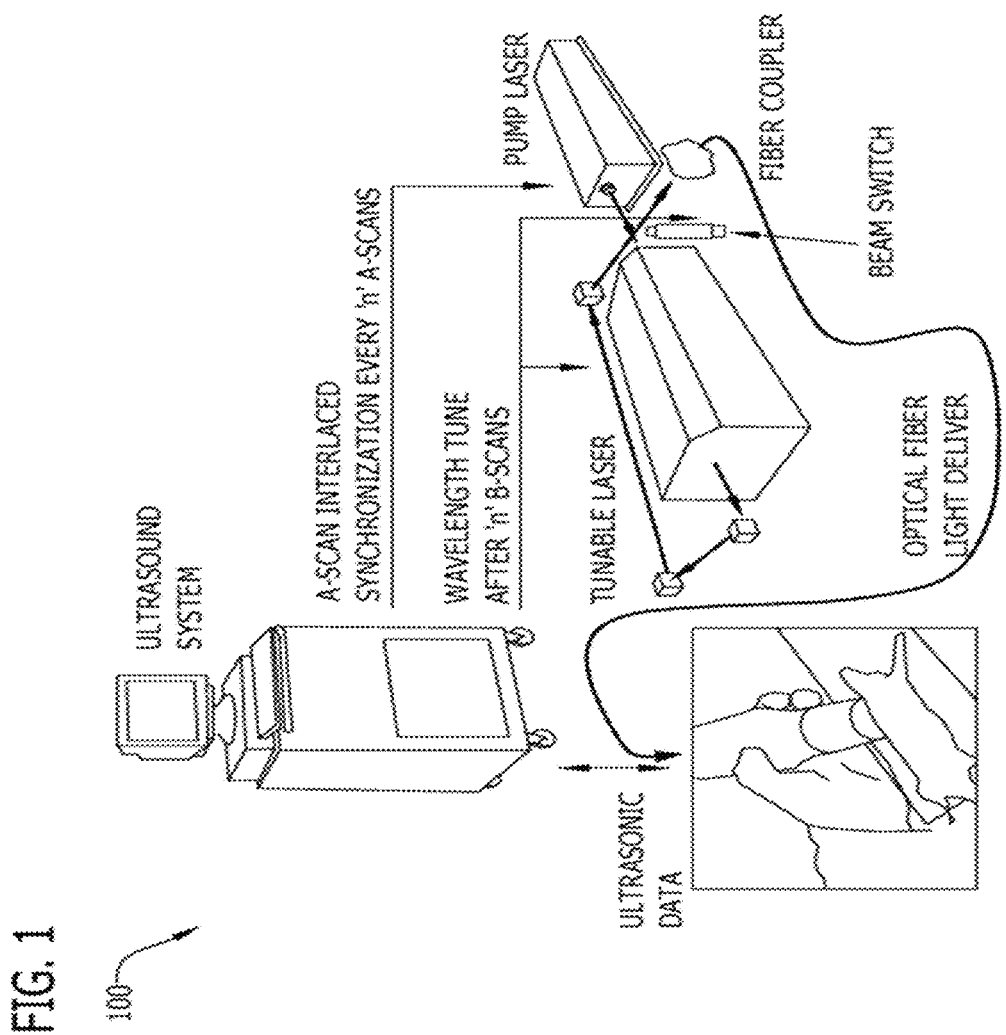
FIG. 1 is a diagram of an imaging system that includes an ultrasonic imaging system and a photoacoustic scanner.

Aspects of the invention may be better understood by referring to the following description in conjunction with the accompanying drawings.

DETAILED DESCRIPTION

While the making and using of various embodiments of the invention are discussed in detail below, it should be appreciated that the presently described embodiments provide many applicable inventive concepts that may be embodied in a wide variety of contexts. The specific embodiments discussed herein are merely illustrative of exemplary ways to make and use embodiments of the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration and are intended to mean that there are one or more of the elements. The terminology herein is used to describe specific embodiments of the invention, but their usage does not delimit the invention, except as outlined in the claims. The terms "comprising," "including," and "having" are intended to be inclusive and mean that there may be additional elements other than the listed elements.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

The terminology herein is used to describe embodiments of the invention, but their usage does not delimit the invention.

To be consistent with the commonly used terminology, whenever possible, the terms used herein follow the definitions recommended by the Optical Society of America (OCIS codes).

In some embodiments, the term "photoacoustic microscopy" refers to a photoacoustic imaging technology that detects pressure waves generated by light absorption in the volume of a material such as, but not limited to, a biological tissue, and propagated to the surface of the material. The term "photoacoustic microscopy" further refers to methods for obtaining images of the optical contrast of a material by detecting acoustic or pressure waves traveling from the object, typically at micrometer scale image resolution. Moreover, "photoacoustic microscopy" includes, but is not limited to, detection of the pressure waves that are still within the object. The methods of photoacoustic microscopy may make use of computer-based image reconstruction although photoacoustic tomography encompasses photoacoustic microscopy.

In various embodiments, the term "photoacoustic tomography" refers to a photoacoustic imaging technology that detects acoustic and/or pressure waves generated by light absorption in the volume of a material such as, but not limited to, biological tissue, and propagated to the surface of the material.

In some embodiments, the term "piezoelectric detectors" refers to detectors of acoustic waves utilizing the principle of electric charge generation upon a change of volume within crystals subjected to a pressure wave.

In some embodiments, the terms "reflection mode" and "transmission mode" refer to modes of operating a photoacoustic imaging system. "Reflection mode" employs the detection of acoustic and/or pressure waves transmitted from a volume from which the waves are generated to an optically irradiated surface. "Transmission mode" employs the detection of acoustic and/or pressure waves transmitted from a volume from which the waves are generated to a surface that is opposite to, or substantially different from, the irradiated surface.

In some embodiments, the term "time-resolved detection" refers to the recording of the time history of a pressure wave with a temporal resolution sufficient to reconstruct the pressure wave profile.

In some embodiments, the term "transducer array" refers to an array of ultrasonic transducers.

In some embodiments, the terms "transducer array" and "phase array transducer" refer to an array of piezoelectric ultrasonic transducers.

In some embodiments, the terms "focused ultrasonic detector," "focused ultrasonic transducer," and "focused piezoelectric transducer" refer to a curved ultrasonic transducer with a hemispherical surface, a planar ultrasonic transducer with an acoustic lens attached, or an electronically focused ultrasonic array transducer.

In some embodiments, the term "photoacoustic waves" refers to pressure waves produced by light absorption.

In some embodiments, "isosbestic wavelength" refers to a wavelength of light characterized by a hemoglobin absorbance that corresponds to an oxyhemoglobin absorbance.

In some embodiments, "non-isosbestic wavelength" refers to a wavelength of light characterized by a hemoglobin absorbance that does not correspond to an oxyhemoglobin absorbance.

In embodiments of the invention, the term "diffraction-limited focus" includes, but is not limited to, an optimal focusing of light within limitations imposed by diffraction.

In embodiments of the invention, the term "confocal" refers to a feature of a photoacoustic imaging system characterized by the focus of the illumination system coinciding with the focus of the detection system.

As will be described below, embodiments of the invention provide a method of characterizing a target within a tissue by focusing one or more laser pulses on the region of interest in the tissue so as to penetrate the tissue and illuminate the region of interest. The pressure waves induced in the object by optical absorption are received using one or more ultrasonic transducers that are focused on the same region of interest. The received acoustic waves are used to image the structure or composition of the object. The one or more laser pulses are focused by an optical assembly, typically including optical fibers, lenses, prisms and/or mirrors, which converges the laser light towards the focal point of the ultrasonic transducer. The focused laser light selectively heats the region of interest, causing the object to expand and produce a pressure wave whose temporal profile reflects the optical absorption and thermo-mechanical properties of the object. In addition to a single-element focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one- or two-directional sector scanning of the object. The cantilever beam is suspended inside a closed, liquid filled container, which has an acoustically and optically transparent window on a side of the transducer-light delivery optics assembly. The window may be permanent or disposable. The window is positioned on an object surface, where acoustic coupling gel is applied. Neither immersion of the object in water nor movement of the scanner relative to the object surface is necessary to perform imaging. Further, a linear transducer array, focused or unfocused in elevation direction, may be used to accelerate image formation. The signal recording includes digitizing the received acoustic waves and transferring the digitized acoustic waves to a computer for analysis. The image of the object is formed from the recorded acoustic waves.

In addition, embodiments of the invention may also include one or more ultrasonic transducers or a combination thereof. The electronic system includes scanner drivers and controllers, an amplifier, a digitizer, laser wavelength tuning electronics, a computer, a processor, a display, a storage device or a combination thereof. One or more components of the electronic system may be in communication remotely with the other components of the electronic system, the scanning apparatus or both.

The imaging method described herein, which uses a confocal photoacoustic imaging system, is one of the possible embodiments, specifically aimed at medical and biological applications but not limited to these applications. The embodiments of the invention are complementary to pure optical and ultrasonic imaging technologies and may be used for diagnostic, monitoring or research purposes. The main applications of the technology include, but are not limited to, the imaging of arteries, veins, capillaries (the smallest blood vessels), pigmented tumors such as melanomas, hematomas, acute burns, and or sentinel lymphatic nodes in vivo in humans or animals. Embodiments of the invention may use the spectral properties of intrinsic optical contrast to monitor blood oxygenation (oxygen saturation of hemoglobin), blood volume (total hemoglobin concentration), and even the metabolic rate of oxygen consumption; it may also use the spectral properties of a variety of dyes or other contrast agents to obtain additional functional or molecular-specific information. In other words, embodiments of the invention are capable of functional and molecular imaging.

In other aspects, a single-RBC photoacoustic flowoxigraphy (FOG) device is described herein, which can noninvasively image oxygen delivery from single flowing RBCs in vivo with 10 millisecond temporal resolution and 3.4 micrometer spatial resolution. The single-RBC photoacoustic flowoxigraphy (FOG) device uses intrinsic optical absorption contrast from oxy-hemoglobin ($HbO_2$) and deoxy-hemoglobin (Hb), and therefore, allows label-free imaging. Multiple single-RBC functional parameters, including the total hemoglobin concentration ($C_{Hb}$), the oxygen saturation ($sO_2$), the gradient of oxygen saturation ($\nabla sO_2$), the flow speed ($V_{flow}$), and the metabolic rate of oxygen ($MRO_2$), may be simultaneously quantified in real time. The system works in reflection instead of transmission mode, allowing noninvasive imaging in vivo.

Other embodiments of the invention may be used to monitor possible tissue changes during x-ray radiation therapy, chemotherapy, or other treatment, and may also be used to monitor topical application of cosmetics, skin creams, sun-blocks or other skin treatment products. Embodiments of the invention, when miniaturized, may also he used endoscopically, e.g. for the imaging of atherosclerotic lesions in blood vessels or precancerous and cancerous lesion in the gastrointestinal tract.

To incorporate photoacoustic imaging into an ultrasonic scanning system or imaging system 100, a photoacoustic excitation source, such as a tunable pulsed dye laser, and a light delivery system are introduced to the ultrasonic scanning system 100 as shown in FIG. 1. The light delivery system, including an optical fiber and light focusing optics, are integrated into the handheld ultrasonic scanner. Light from either the pump laser (before frequency doubling) or the tunable dye laser may be selected with a beam switch and coupled into the optical fiber. The laser must be synchronized with the imaging system 100. In the exemplary embodiment, the imaging system 100 interlaces trigger pulses between the laser and the ultrasonic pulses. The imaging system 100 also controls the emission wavelength of the tunable laser. The light focusing optics is placed inside the ultrasonic scanning head.

Figure 2:
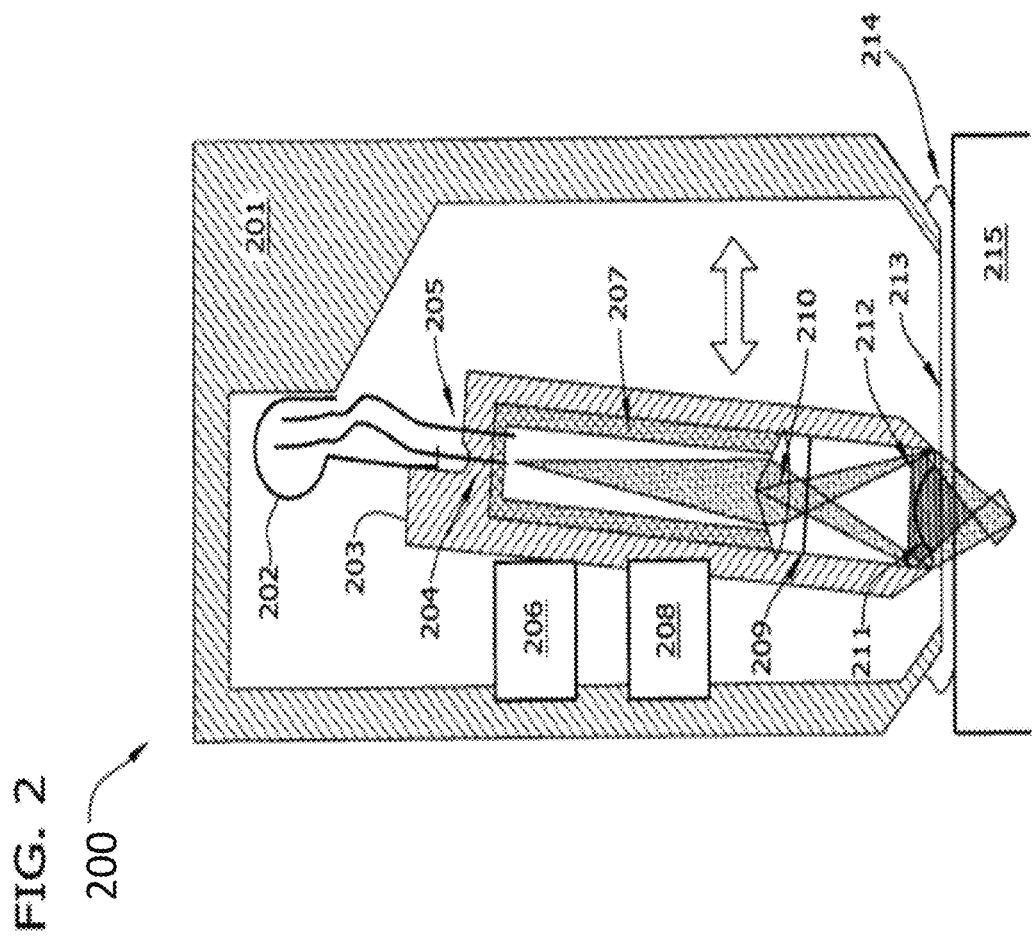
FIG. 2 is a schematic diagram of an exemplary direct contact dark-field photoacoustic microscopy scanner.

FIG. 2 is a diagram of an exemplary photoacoustic scanner 200 of the imaging system in accordance with one embodiment of the invention. As shown in FIG. 2, scanner 200 is implemented as a handheld device. A dye laser, pumped by a Q-switched pulsed neodymium-doped yttrium lithium fluoride (Nd:YLF) laser delivers approximately 1.0 millijoules (mJ) per pulse to a 0.60-mm diameter optical fiber 204. The laser pulse width is approximately 8.0 nanoseconds (ns), and the pulse repetition rate varies from approximately 0.1 kilohertz (kHz) to approximately 2.0 kHz. The fiber output 204 is coaxially positioned with a focused ultrasonic transducer 211. The concave bowl-shaped transducer 211 has a center frequency of approximately 30.0 megahertz (MHz) and a nominal bandwidth of 100%. The laser light from the fiber 204 is expanded by a conical lens 210 and then focused through an annular hollow cone shaped optical condenser 212, which also serves as a back-plate of the ultrasonic transducer. The optical focal region overlaps with the focal spot of the ultrasonic transducer 211, thus forming a confocal optical dark-field illumination and ultrasonic detection configuration. The photoacoustic setup is mounted inside a hollow cylindrical cantilever beam 203 supported by a flexure bearing 202. The cantilever beam 203 is mounted inside a container 201. The container is filled with immersion liquid and sealed with an optically and acoustically transparent membrane 213. The object 215, e.g., animal or human, is placed outside the container 201 below the membrane 213, and the ultrasonic coupling is further secured by coupling gel 214. The cantilever beam is moved by an actuator 206, and its inclination angle is controlled by a sensor 208. Part of the laser pulse energy is reflected from the focusing optics, such as a conical lens 210, and after multiple reflections from the diffusely reflecting coating of the integrating chamber 207, is detected by a photodetector 205. The signal from the photo-detector 205 is used as a reference signal to take into account energy fluctuations of the laser output. An aperture diaphragm 209 screens the photo-detector 205 from ambient light and sample surface reflection.

Compared to alternative designs, the above design provides the following advantages. First, the high axial stiffness of the cantilever beam increases repeatability of the axial position of the photoacoustic detector. Second, the frictionless flexure bearing pivot decreases the lateral position error of the photoacoustic detector and the mass of the system, thereby decreasing mechanical vibration (noise) of the scanner and increasing its overall mechanical stability. Third, the sealed container design makes the photoacoustic scanner portable and ergonomic, which widens the application field of the photoacoustic technique, especially in medical and biological practice. Fourth, the device performs interlaced acquisition of time-resolved laser-induced pressure waves and reflected ultrasonic pulses, which may be used, for example, to measure the tissue metabolic rate through co-registration of ultrasound pulsed-Doppler and photoacoustic spectral data at high temporal and spatial resolution.

Figure 3:
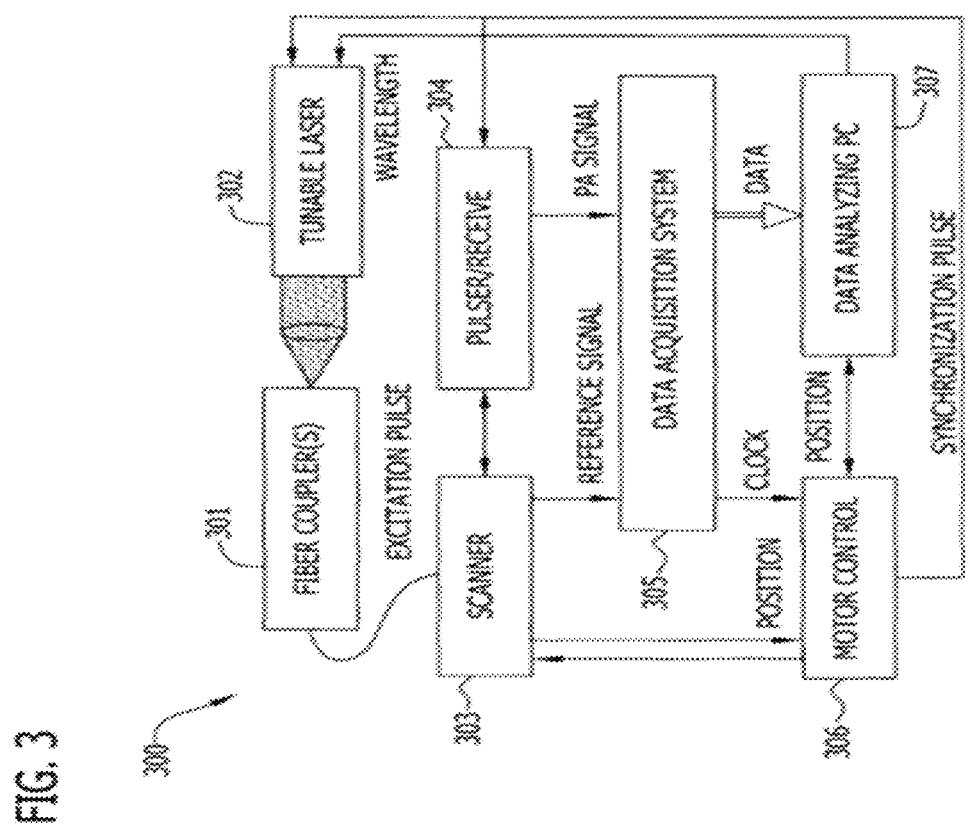
FIG. 3 is a block diagram of an exemplary quantitative spectroscopic measurement system that includes the photoacoustic microscopy scanner shown in FIGS. 1 and 2.

FIG. 3 is a block diagram of an exemplary photoacoustic system 300 that uses dark-field photoacoustic microscopy with sector scanning and quantitative spectroscopic measurement capability in accordance with one embodiment of the invention. The system includes a light delivery subsystem that includes of a tunable pulsed laser subsystem 302, an optical fiber or fibers and the associated fiber coupling optics 301, a scanner 303 that includes a light focusing device and one or more ultrasonic transducers, and an electronic system that may include an ultrasonic pulser/receiver 304, a motion controller 306, a data acquisition system 305, and a data-analyzing computer 307. Depending on the particular application, the photoacoustic system 300 may have an array of peripheral devices (not shown) such as manipulation arm, health and environment monitoring devices, and data storage. The focusing device of the scanner 303 is connected to an output of the fiber coupler 301 via single or multiple optical fibers that receive one or more laser pulses from the tunable laser 302 and focus the one or more laser pulses into a tissue so as to illuminate the tissue. The one or more ultrasonic transducers positioned alongside the focusing optics are focused on the region of interest and receive acoustic or pressure waves induced in the object by the laser light. The electronic system records and processes the received acoustic or pressure waves and controls scanner motion. Ultrasonic transducers may work in two modes, as a receiving transducer for photoacoustic signals and as a pulser/receiver for conventional pulse/echo ultrasonic imaging. The focusing device includes an optical assembly of lenses, prisms, and/or mirrors that expands and subsequently converges the laser light toward the focal point of the one or more ultrasonic transducers.

The dark field confocal photoacoustic sensor is placed on a cantilever beam to perform sector scanning along the tissue surface. The near-simultaneously (e.g., approximately 20.0 microsecond (μs) delayed) recorded photoacoustic and pulse/echo pressure-wave time histories are displayed by the data-analyzing PC 307 versus the photoacoustic sensor position to construct co-registered images of the distribution of the optical and mechanical contrast within the tissue. Depending on the type of scanning (e.g., one or two axis), the device produces cross-sectional (B-scan) or volumetric images of the tissue structure. When the tissue under investigation is an internal organ, the optical fiber and transducer may be incorporated in an endoscope and positioned inside the body.

The data acquisition subsystem 305 produces a clock signal to synchronize all electronic components of the photoacoustic device. The motor controller 306 drives the cantilever beam actuators and measures the current position of the photoacoustic transducer. At transducer locations predefined by the data-analyzing computer 307, the motor controller generates trigger pulses synchronized with the clock signal, which are used to trigger the pulse laser and start the data acquisition sequence.

High-frequency ultrasonic waves generated in the tissue by the laser pulse are recorded and analyzed by the data analyzing computer 307 to reconstruct an image. The shape and dimensions of the optical-contrast tissue structures are generally determined from the temporal profile of the laser-induced ultrasonic waves and the position of the focused ultrasonic transducer. A single axis sector scanning by the ultrasonic transducer positioned within the cantilever beam is used to form a two-dimensional image, and two-axis scanning is used to form a three-dimensional image. However, a transducer array may be used to reduce the time of scanning and light exposure. The following examples are provided for the purpose of illustrating various embodiments of the invention, and are not meant to limit the embodiments of the invention in any fashion.

To obtain functional images, laser pulses from a tunable laser (e.g., a dye laser) are used to illuminate the tissue surface. By switching between several light wavelengths, the optical absorption spectrum of a tissue structure may be measured. This spectrum is influenced by the dispersion of optical absorption and scattering in the object. Nevertheless, in cases where the tissue absorption has definite and distinct spectral features, which is the case, for example, with oxyhemoglobin and deoxyhemoglobin, by using a proper minimization procedure it is possible to separate the contributions of different tissue constituents, and thus permit the measurement of local blood oxygenation in the tissue in order to separate normal and diseased tissues. Similarly, certain tumors may be identified by targeting them with biomolecules conjugated to various contrast agents such as selectively absorbing dyes.

Embodiments of the invention may include any realization of a photoacoustic imaging device which uses a cantilever beam to perform object scanning. The following devices may implement the method described herein: a semi-rigid cantilever beam supported by a flexure bearing, a fixed end flexible cantilever beam, a cantilever beam with two degrees of freedom supported by two perpendicular flexure bearings, and a cantilever beam supported by a flexure bearing attached to a linear scanning stage.

Figure 4:
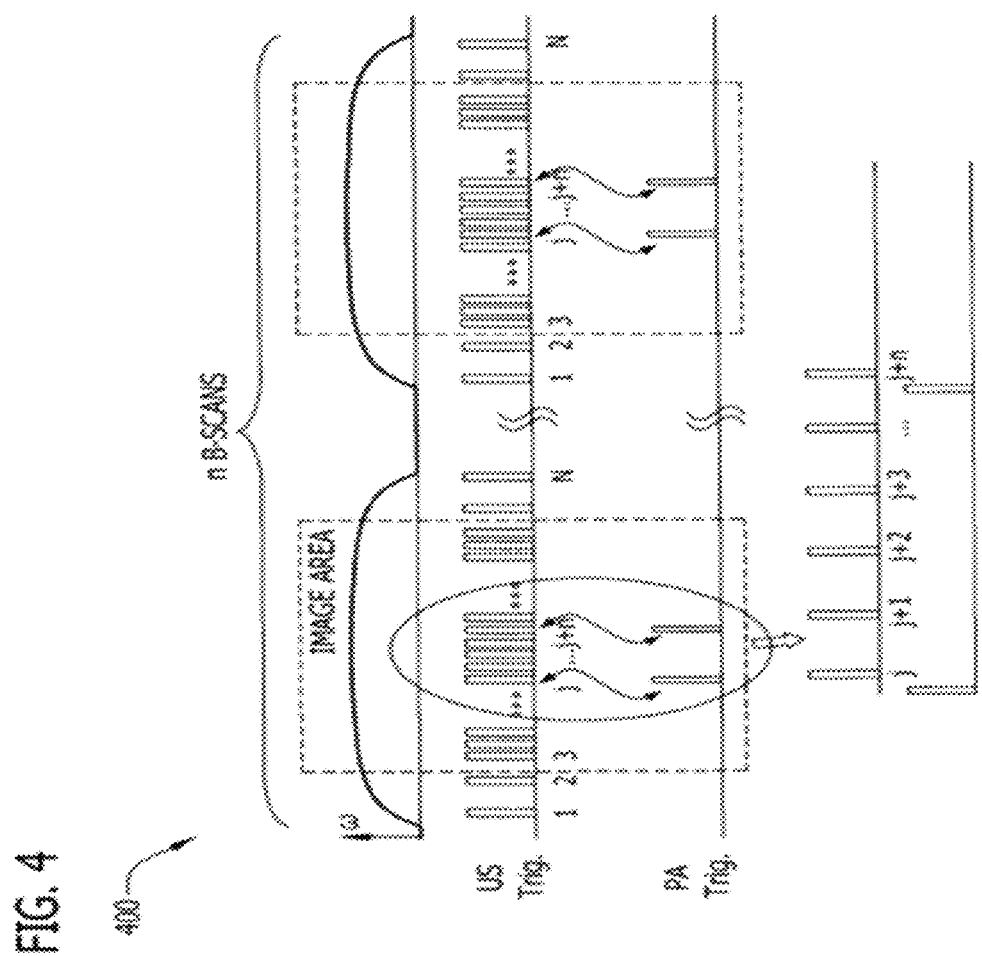
FIG. 4 is a timing diagram for photoacoustic imaging used by the scanner shown in FIGS. 1, 2, and 3.

To synchronize the optical and ultrasonic components of the ultrasonic-based photoacoustic imaging system, the ultrasonic system shown in FIGS. 1-3 generates a triggering signal for the pulsed laser as shown in the timing diagram 400 of FIG. 4. The ultrasonic system acquires signals from the ultrasonic transducer and reference photo-detector and superimposes and/or codisplays photoacoustic images and ultrasound pulse-echo images. More specifically, a pump laser produces a pulse energy of approximately 20.0 mJ at a fundamental wavelength of approximately 1056.0 nm, and/ or a tunable dye laser produces a pulse energy of greater than approximately 2.0 mJ at a frequency of up to approximately 2.0 kHz. The laser system thus provides approximately 8.0 ns wide laser pulses, which are short enough for the targeted spatial resolution. The ANSI safety limits are satisfied for a pulse energy less than or equal to approximately 2.0 mJ, a diameter of illumination greater than or equal to approximately 6.0 mm, a laser frequency less than or equal to approximately 2.0 kHz, and a scanning step size greater than or equal to approximately 0.1 mm. At 2 kHz PRF, the data acquisition time for a B-scan frame consisting of 200 A-lines is approximately 100.0 ms, yielding a B-scan frame rate of approximately 10.0 Hz. When approximately 20.0 mJ of pulse energy is used for deep penetration, the illumination area is increased to greater than or equal to approximately 1.0 cm2 and the laser PRF decreased to approximately 50.0 Hz. Taking into account the decreased resolution for deep imaging, a B-scan frame rate of approximately 1.0 Hz is achieved if fifty A-lines are acquired to per B-scan.

Moreover, the ultrasonic scanning system generates one photoacoustic imaging synchronization signal for every n pulse-echo ultrasonic triggering pulses (shown as trigger pulses j and j+n in the timing diagram in FIG. 4), where n is approximately the ratio of the ultrasound PRF to the laser PRF. As the ultrasonic scanning progresses into the next frame (Bscan), the laser triggers will be generated in connection with pulse-echo triggers j+1 and j+n+1 correspondingly. After n consecutive frames of scanning, a complete photoacoustic image will be acquired, and the cycle will continue. At this time, the ultrasonic scanning system generates a control word to change the wavelength of the dye laser emission if spectral information is to be collected. Because the photoacoustic imaging system works at a fraction of the frame rate of the ultrasonic system, laser triggers will be simply introduced between consecutive pulse-echo triggers a few microseconds depending on imaging depth (e.g., approximately 20.0 μs for a depth of approximately 30.0 mm) ahead of the corresponding pulse-echo trigger. This lead time will be sufficient for the data acquisition of photoacoustic data before the ultrasonic pulser applies a high voltage to the ultrasonic transducer. This mode of operation does not compromise the pure ultrasonic frame rate while the maximum photoacoustic imaging frame rate is achieved.

Various examples of photoacoustic scanners will now be described in reference to FIGS. 5, 6, and 7, wherein the photoacoustic sensor includes an optical focusing device and one or more ultrasonic transducers.

The embodiments of the invention provides fast (e.g., approximately thirty frames per second) high resolution photoacoustic imaging of biological tissues in vivo. This particular embodiment has a lateral resolution as high as approximately 50.0 micrometers (μm) and an imaging depth limit of about 5.0 mm. The image resolution may be further improved by either increasing the frequency and bandwidth of the ultrasonic transducer or increasing the numerical aperture of the optical objective lens. The latter applies when imaging within the depth of one optical transport mean free path is desired. With the help of an ultrasonic array transducer, faster photoacoustic imaging is possible and signal averaging, when needed, is also realistic.

Embodiments of the invention may include any realization of light focusing using any kind of mirrors, prisms, lenses, fibers, and diaphragms that may produce illumination directed to the focal area of the focused ultrasonic transducer if sector scanning of the object is performed. Embodiments of the invention may also include any photoacoustic techniques with any light delivery and ultrasonic detection arrangement placed inside a sealed container for scanning, where the container may remain motionless during acquisition of one image frame.

The following devices may be used to implement photoacoustic sensing for the purpose described herein: (1) a bowl-shaper focusing ultrasonic transducer; (2) a flat ultrasonic transducer attached to an acoustic lens; (3) a linear or (4) an annular focused or unfocused ultrasonic transducer array combined with an optical microscope annular condenser which may consist of lenses, mirrors, prisms or their combination. Various examples of the photoacoustic assembly suitable to be placed inside the hollow cantilever beam will now be described in reference to FIGS. 5, 6, and 7 wherein the focusing assembly includes an optical focusing device and one or more ultrasonic transducers.

Figure 5:
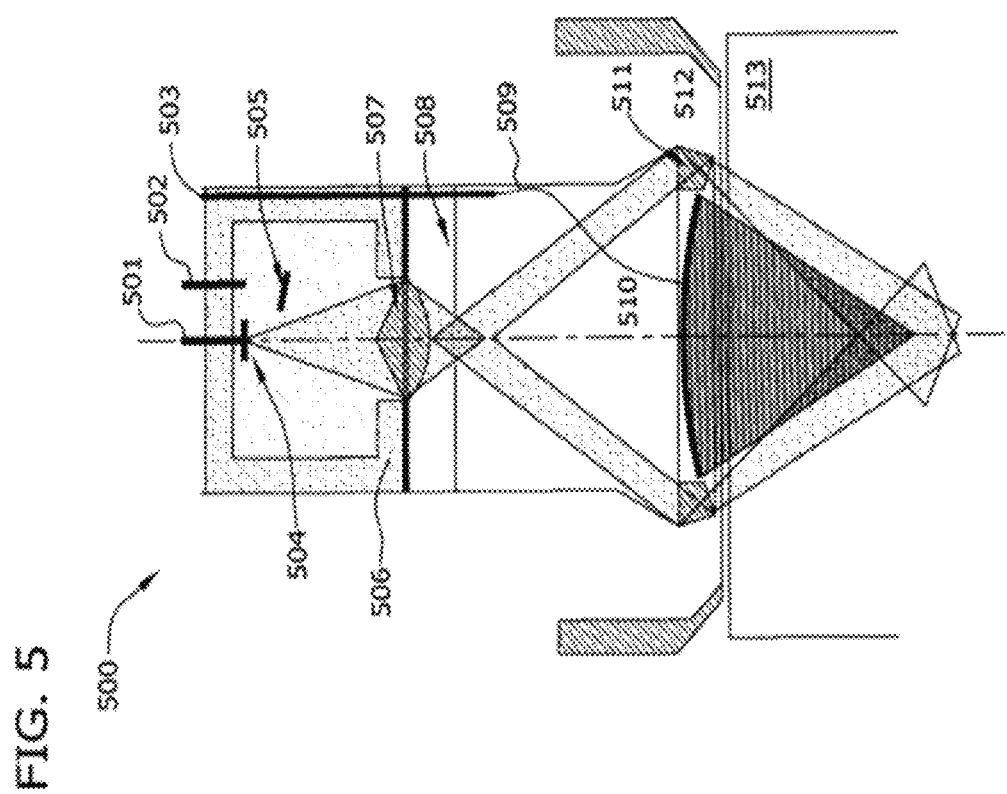
FIG. 5 is a schematic diagram of an exemplary photoacoustic head that may be used with the measurement system shown in FIG. 3, including a single-element spherically focusing transducer.

A diagram of a photoacoustic sensor assembly 500 of the imaging system in accordance with the main embodiment of the embodiments of the invention is shown in FIG. 5. More specifically, FIG. 5 shows a diagram of one embodiment of a photoacoustic sensor 500 in accordance with the scanner design shown in FIG. 1. A laser pulse is delivered via optical fiber 501, expanded by a conical lens 507, passed around the ultrasonic transducer 510, and focused by a conical prism 511. The transducer 510, focusing optics 507 and 511, optical fibers 501 and 502, and electrical wires connecting the transducer are placed inside the cylindrically shaped cantilever beam 509. In a non-scattering object, the laser energy distribution along the ultrasonic transducer axis would be confined to the transducer's depth of focus. In highly scattering media, the laser energy distribution is broader. The laser light penetrates through the transparent membrane 512 and the surface of the object 513 to a sufficient depth, selectively heating targets in the tissue that have higher optical absorption and producing ultrasonic waves. The ultrasonic waves that propagate toward the tissue surface are detected by an acoustic transducer 510, and digitized and transferred to a computer for data analysis. Part of the energy of the laser pulse is reflected from the lens surface, and the reflected light is homogenized by multiple reflections from the diffusively reflective coating of an integrating chamber 506 and reaches the sensing optical fiber 502. The output of the sensing optical fiber 502 is connected to a photo-detector (not shown). This measurement is used to compensate for the fluctuations in the laser output. An iris diaphragm 508 prevents most ambient light from entering the integrating chamber. An optical absorber 504 absorbs collimated back reflected and ambient light, which enters the integrating chamber through the iris aperture. A baffle 505 shields the sensing fiber from direct exposure to light reflected from the conical lens.

Figure 6:
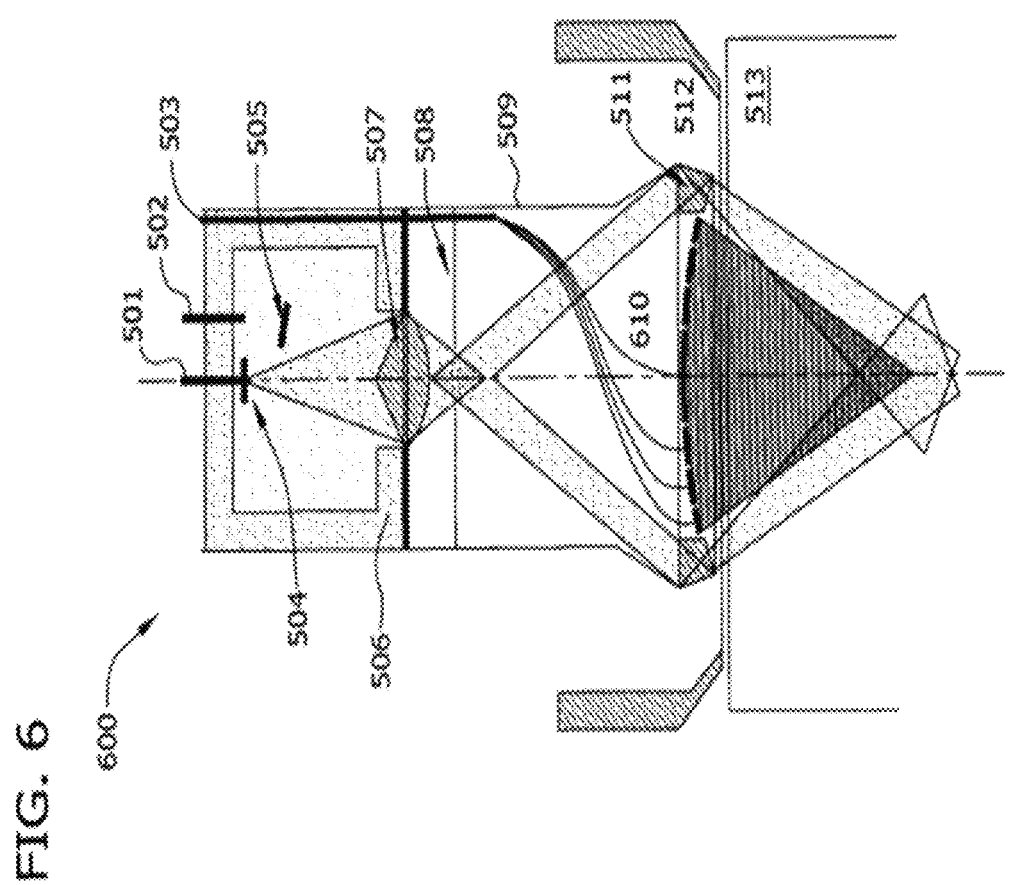
FIG. 6 is a schematic diagram of a second exemplary photoacoustic head that may be used with the measurement system shown in FIG. 3, including a spherically focusing annular transducer array.

FIG. 6 shows a diagram of another embodiment of a photoacoustic sensor 600 of the imaging system in accordance with FIG. 1. The photoacoustic sensor 600 is similar to photoacoustic sensor 500 (shown in FIG. 5), except that the single-element focused ultrasonic transducer is replaced with a multi-element annular piezoelectric transducer array 610. The ultrasonic transducer array 610 may be dynamically focused to different depths for a single laser pulse by introducing time-of flight-dependent time delays between signals from different transducer elements, thus extending the depth range of the cross-sectional (B-scan) image with high lateral resolution.

Figure 7:
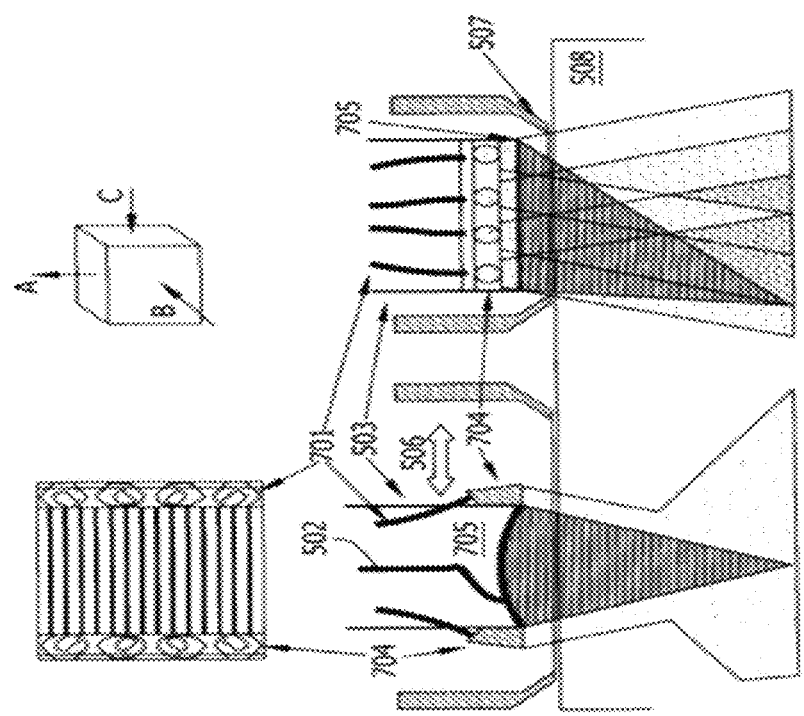
FIG. 7 is a schematic diagram of a third exemplary photoacoustic head that may be used with the measurement system shown in FIG. 3, including a linear phase array of ultrasonic transducers.

FIG. 7 shows a diagram of yet another embodiment of a photoacoustic sensor 700 of the imaging system 100 shown in FIG. 1. The photoacoustic sensor 700 uses a multitude of optical fibers 701, a system of prisms 704 to deliver light pulses, and a one-dimensional cylindrically focused transducer array 705 to form a photoacoustic B-scan image. In this embodiment, the photoacoustic sensor 700 uses translational symmetry instead of cylindrical symmetry. Unlike the embodiments shown in FIGS. 5 and 6, a wedge-shaped light beam is formed instead of a cone-shaped one, and a linear transducer array 705, similar to one used in medical ultrasonic diagnostics, is used to acquire photoacoustic signals. Using beam forming, such a device may produce a complete photoacoustic B-scan image with a single laser pulse, making possible ultrafast real-time photoacoustic imaging with the B-scan frame rate limited by the pulse repetition rate of the laser. Sector scanning the single row of piezoelectric elements produces volumetric photoacoustic images at potential rates of approximately thirty volumetric frames per second.

Figure 8:
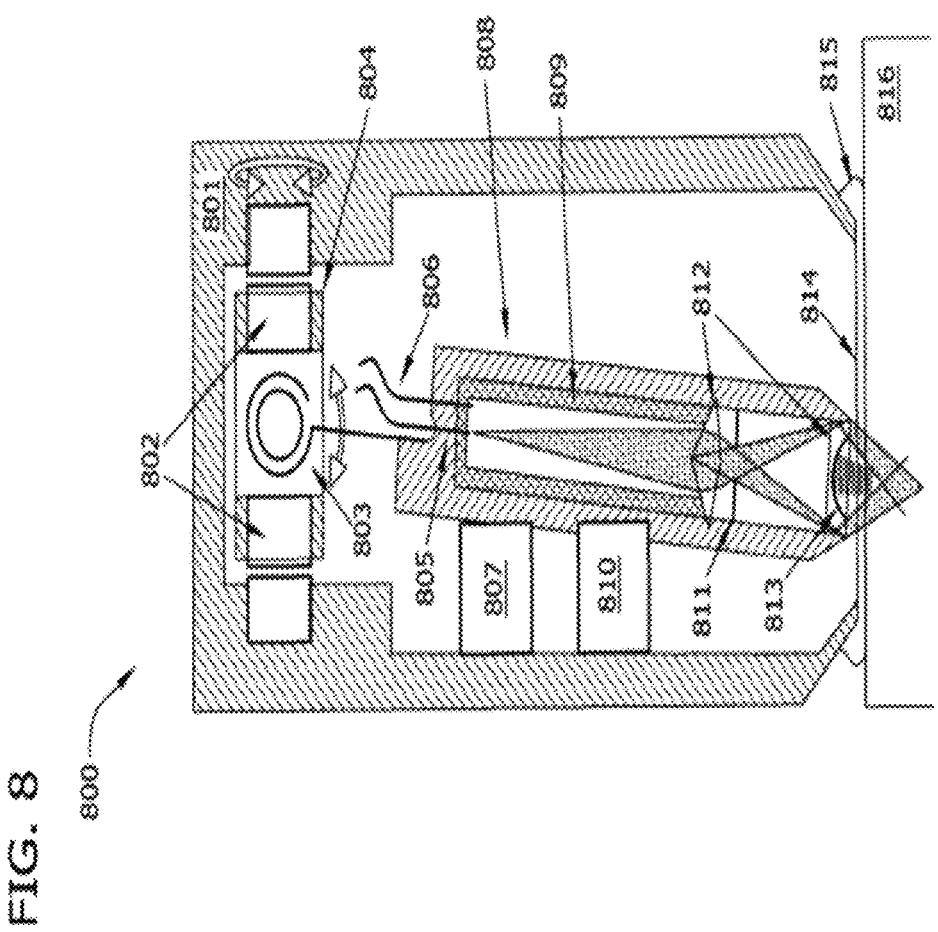
FIG. 8 is a schematic diagram of an exemplary photoacoustic scanner system that uses cantilever beam-based two-dimensional scanning for volumetric imaging.

FIG. 8 is a block diagram of another embodiment of a photoacoustic scanner 800 that uses sector scanning in two perpendicular directions. A laser pulse is coupled into an optical fiber 805, which is coaxially positioned with the focused ultrasonic transducer 813. With the help of the focusing optics 812, the laser light from the fiber 805 is expanded, passed around the transducer, and then converged towards the ultrasonic focus inside the object under investigation 816. The optical focal region overlaps with the focal spot of the ultrasonic transducer 813, thus forming a confocal optical dark-field illumination and ultrasonic detection configuration. The photoacoustic setup is mounted inside a hollow cylindrical cantilever beam 808 supported by a first flexure bearing 803. The bearing 803 is mounted in a frame 804, which is mounted inside a container 801 on second and third flexure bearings 802. The axis of rotation of the second and third bearings 802 is perpendicular to the axis of rotation of the first bearing 803. Tilting of the cantilever beam 808 in two perpendicular directions results in two dimensional scanning along the object surface. The container 801 is filled with immersion liquid and sealed by an optically and acoustically transparent membrane 814. The object (e.g., animal or human) 816 is placed outside the container 801 below the membrane 814, and ultrasonic coupling is further secured by coupling gel 815. The cantilever beam 808 is moved by an actuator 807, and its inclination angle is controlled by a sensor 810. Part of the laser pulse energy is reflected from the focusing optics, such as conical lens 812, and, after multiple reflections from the diffusely reflective coating of an integrating chamber 809, is transmitted by the sensing optical fiber 806 to a photo-detector (not shown). The signal from the photo-detector is used as a reference signal to offset the energy fluctuations of the laser output. An aperture diaphragm 811 screens the photo-detector from ambient light and sample surface reflection.

Figure 9:
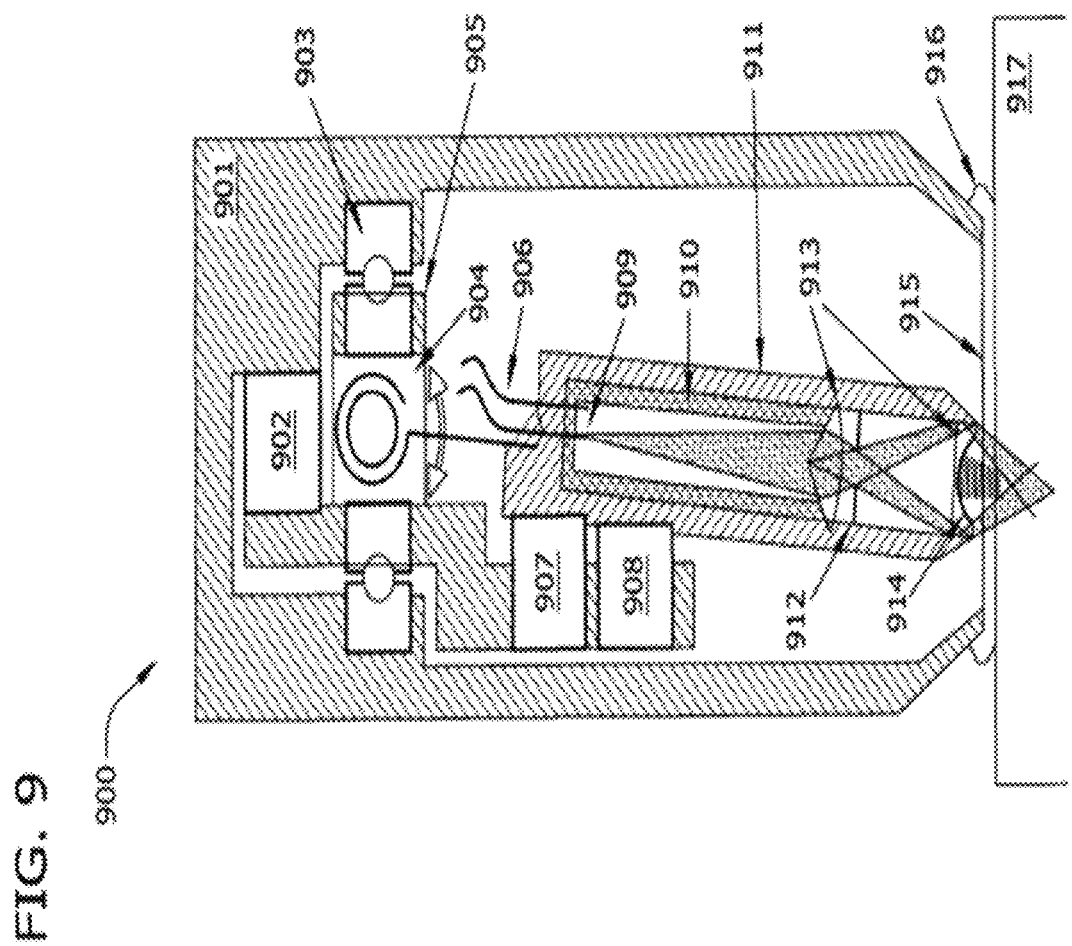
FIG. 9 is a schematic diagram of a second exemplary photoacoustic scanner system that combines cantilever beam scanning and linear translation scanning for volumetric imaging.

FIG. 9 is a block diagram of another embodiment of a photoacoustic scanner 900 that uses sector scanning in one direction and linear scanning in a perpendicular direction. A laser pulse is coupled into optical fiber 909, which is coaxially positioned with a focused ultrasonic transducer 914. With the help of a focusing optics 913, the laser light from the fiber 909 is expanded, passed around the transducer 914, and then converged towards the ultrasonic focus inside the object under investigation 917. The optical focal region overlaps with the focal spot of the ultrasonic transducer 914, thus forming a confocal optical dark-field illumination and ultrasonic detection configuration. The photoacoustic detector setup is mounted inside a hollow cylindrical cantilever beam 911 supported by a flexure bearing 904, which is mounted in a frame 905. The frame 905 is mounted on a translation stage 903 inside a container 901. The axis of rotation of the bearing 904 is perpendicular to the displacement direction of the translation stage 903. Tilting of the cantilever beam 911 in combination with linear motion in a perpendicular direction results in two dimensional scanning along the object surface. The container 901 is filled with immersion liquid and sealed with optically and acoustically transparent membrane 915. The sample (e.g., animal or human) 917 is placed outside the container 901 below the membrane 915, and the ultrasonic coupling is further secured by coupling gel 916. The cantilever beam 911 is moved by an actuator 907, and its inclination angle is controlled by a sensor 908. The translation stage 903 is moved by a motor 902, which may be a combination of a ball screw, belts, a step motor, a voice coil linear actuator, or piezoelectric actuator. Part of the laser pulse energy is reflected from the focusing optics, such as conical lens 913, and, after multiple reflections from the diffusely reflective coating of an integrating chamber 910, is transmitted by the sensing optical fiber 906 to a photo-detector (not shown). The signal from the photo-detector is used as a reference signal to compensate for the energy fluctuations of the laser output. An aperture diaphragm 912 screens the photo-detector from ambient light and sample surface reflections.

Figures 10A, 10B:
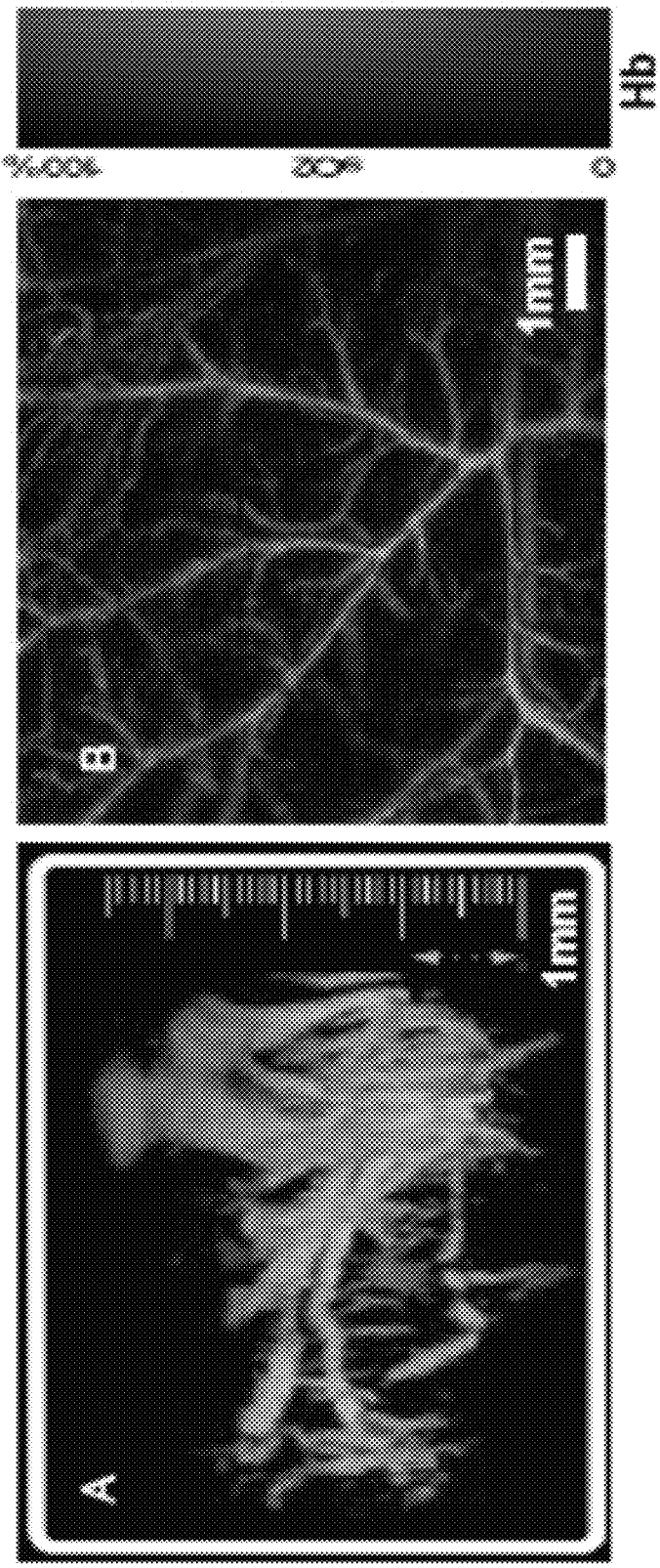
FIG. 10A shows a blood flow image in a mouse prostate taken by an ultrasonic system.
FIG. 10B shows a blood oxygenation level image acquired with photoacoustic imaging.

FIG. 10A shows a blood flow image in a mouse prostate taken by an ultrasonic system and FIG. 10B shows a blood oxygenation level image acquired with photoacoustic imaging. More specifically, FIG. 10A shows 3D tumor perfusion and flow architecture in a mouse prostate tumor imaged by an ultrasonic system, and FIG. 10B shows a photoacoustic image of $sO_2$ in subcutaneous blood vessels in a 200-g Sprague-Dawley rat in vivo. Structural image data reflects the total hemoglobin concentration acquired at 584 nm, color reflects the $sO_2$. The combination of these two contrasts can shed light on tissue oxygen consumption within the volume of for example a relatively small tumor or small organ, which reflects the metabolic rate of the tissue.

Figure 11A:
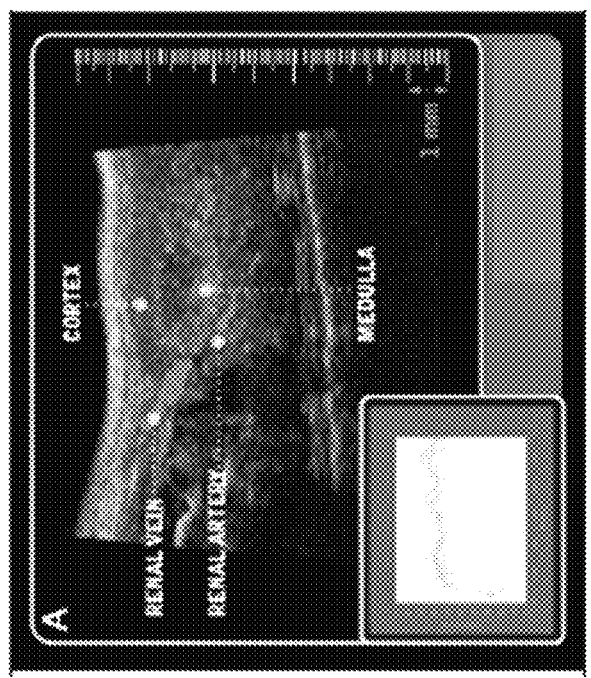
FIG. 11A shows an ultrasonic image of blood vessels.
Figure 11C:
FIG. 11C shows an ex-vivo microsphere-perfusion image of arterioles (red) and venules (blue).
Figure 11B:
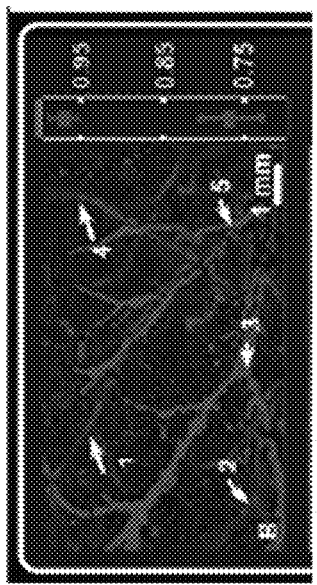
FIG. 11B shows a photoacoustic image of oxygen saturation of hemoglobin ($sO_2$).

Similarly, a contrast agent enhanced ultrasonic image, as shown in FIG. 11A, taken by an ultrasonic system shows blood perfusion and major veins and arteries but must rely on anatomical cues to distinguish between veins and arteries. By contrast, such a distinction can be made by photoacoustic imaging directly using the imaged oxygen saturation of hemoglobin, as shown in FIG. 11B. This distinction is confirmed as shown in FIG. 11C, which shows ex-vivo microsphere-perfusion image of arterioles (red) and venules (blue).

By recording photoacoustic signals obtained at various optical wavelengths, the optical absorption spectrum of the object may be measured. The optical absorption coefficient is dominated by the absorption of hemoglobin in many cases. Because two forms of hemoglobin—oxygenated and deoxygenated—have distinctly different absorption spectra, one may recover the partial concentrations of the two forms of hemoglobin. This value may be used to quantify the oxygen saturation of hemoglobin and the relative total concentration of hemoglobin. Of course, this example merely illustrates the principle, which may be extended to the measurement of other optical absorbers using two or more excitation optical wavelengths.

Because of the fast frame rate, the device in the embodiments of the invention may combine blood flow measurement into and out of regions of interest using the pulse-Doppler technique with blood oxygenation measurements to estimate oxygen metabolism in tissues and organs. The oxygen metabolic rate ($MRO_2$) is the amount of oxygen consumed in a given tissue region per unit time per 100 g of tissue or of the organ of interest. In typical physiological conditions, since hemoglobin is the dominant carrier of oxygen, the key measure of blood oxygenation is the oxygen saturation of hemoglobin ($sO_2$). Therefore, we have $$MRO_2 \propto (sO_{2,in} - sO_{2,out}) \cdot C_{Hb} \cdot A_{in} \cdot \bar{v}_{in} \quad \text{Eqn. (1)}$$

in which $A_{in}$ is the area of the incoming vessel, $\bar{v}_{in}$ is the mean flow velocity of blood in the incoming vessel, and $C_{Hb}$ is the total concentration of hemoglobin. While $A_{in}$ and $\bar{v}_{in}$ may be estimated using ultrasound imaging, $sO_2$ and relative $C_{Hb}$ may be estimated from multi-wavelength photoacoustic methods.

Figure 12:
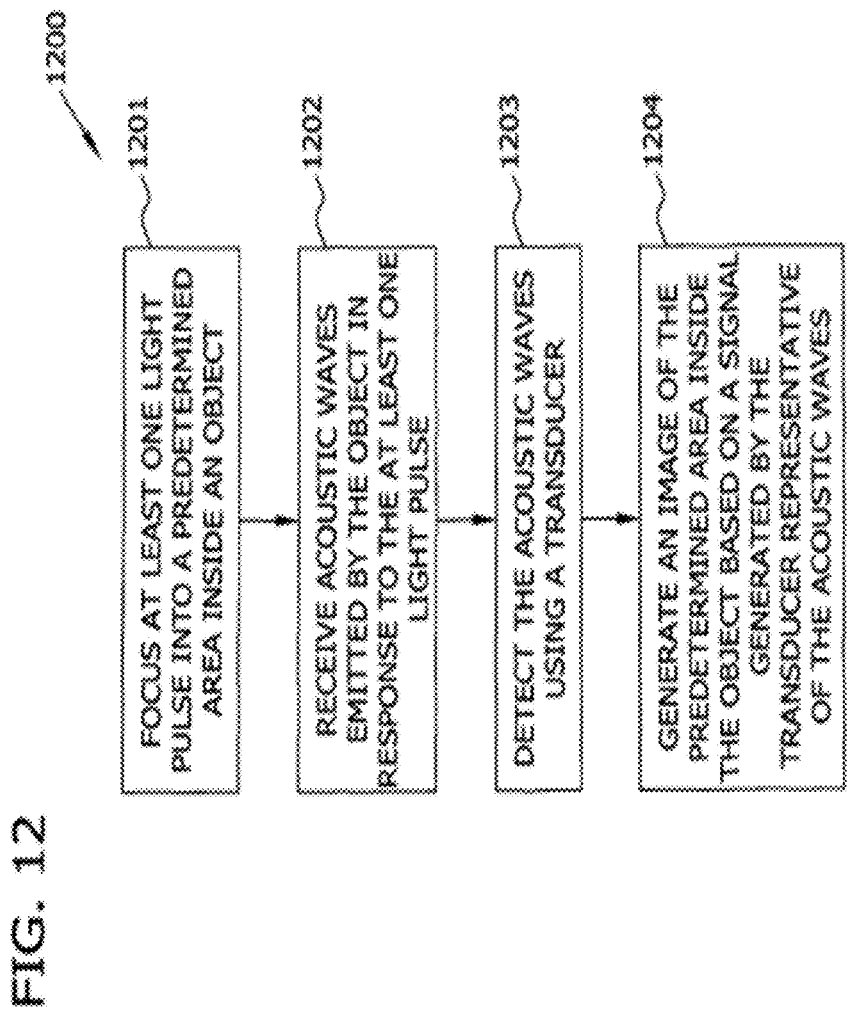
FIG. 12 is a flowchart illustrating an exemplary photoacoustic tomography imaging method.

FIG. 12 is a flowchart 1200 illustrating an exemplary photoacoustic tomography imaging method that characterizes a tissue by focusing 1201 one or more laser pulses on a region of interest in the tissue and illuminating the region of interest. More specifically, the laser pulses are emitted from collimating optics mounted on a cantilever beam that is flexibly mounted within a handheld device. In one embodiment, the cantilever beam is a semi-rigid cantilever beam supported by a flexure bearing. In another embodiment, the cantilever beam is a fixed-end flexible cantilever beam. In another embodiment, the cantilever beam is mounted with two degrees of freedom and is supported by perpendicular flexure bearings. In yet another embodiment, the cantilever beam is supported by a flexure bearing that is coupled to a linear scanning cage. Acoustic waves induced in the object by optical absorption are received 1202 and a signal is generated 1203 representative of the acoustic waves using one or more ultrasonic transducers that are focused on the same region of interest. The signal is then used to image 1204 the structure or composition of the object. The one or more laser pulses are focused by an optical assembly, which typically includes lenses, prisms, and/or mirrors. The optical assembly converges the laser light towards the focal point of the ultrasonic transducer. The focused laser light selectively heats the region of interest, causing the object to expand and produce a pressure wave having a temporal profile that reflects the optical absorption and thermo-mechanical properties of the object. In addition to a single-element, focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one-directional or two-directional sector scanning of the object. The cantilever beam is suspended inside a closed, liquid-filled container, which has an acoustically and optically transparent window on a side of the transducer-light delivery optics assembly. The window is positioned on an object surface and acoustic coupling gel is applied. The received acoustic waves are digitized and the digitized acoustic waves are transmitted to a computer for analysis. An image of the object is then formed from the digitized acoustic waves.

Figure 13:
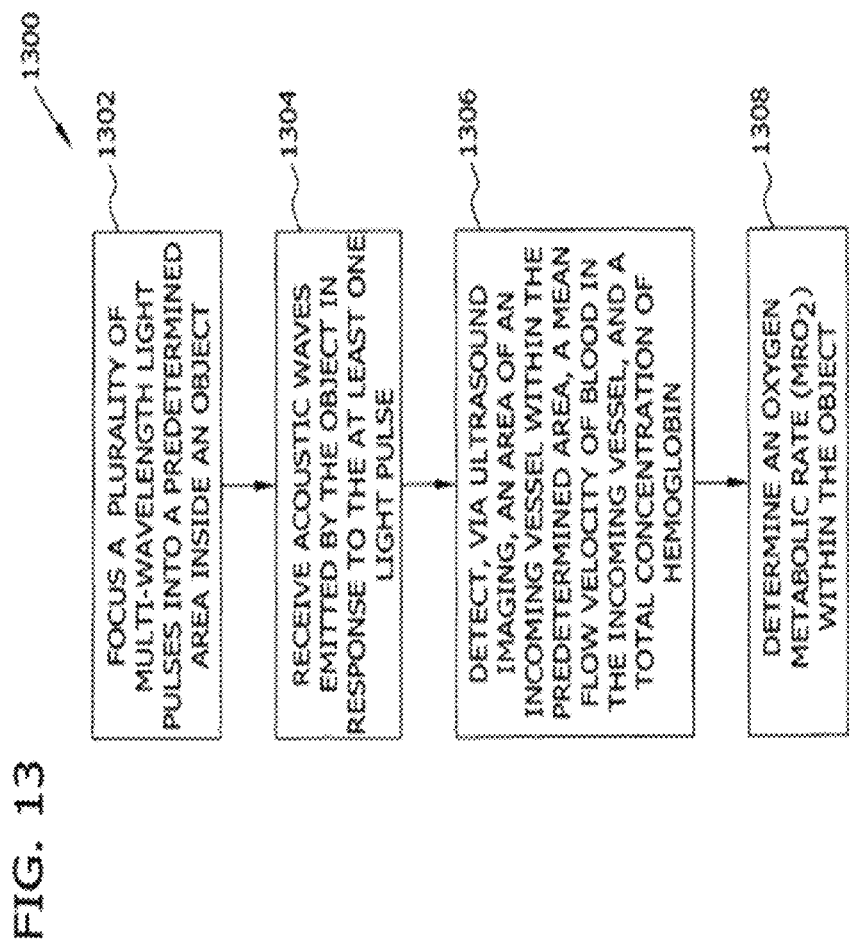
FIG. 13 is a flowchart illustrating an exemplary method for determining an oxygen metabolic rate within a biological tissue.

FIG. 13 is a flowchart 1300 illustrating an exemplary method for determining an oxygen metabolic rate ($MRO_2$) within a biological tissue using a handheld device. A plurality of multi-wavelength light pulses are focused 1302 on a region of interest in the tissue and illuminating the region of interest. More specifically, the laser pulses are emitted from collimating optics mounted on a cantilever beam that is flexibly mounted within a handheld device. In one embodiment, the cantilever beam is a semi-rigid cantilever beam supported by a flexure bearing. In another embodiment, the cantilever beam is a fixed-end flexible cantilever beam. In another embodiment, the cantilever beam is mounted with two degrees of freedom and is supported by perpendicular flexure bearings. In yet another embodiment, the cantilever beam is supported by a flexure bearing that is coupled to a linear scanning cage. Acoustic waves induced in the object by optical absorption are received 1304 using one or more ultrasonic transducers that are focused on the same region of interest. The signal is then used to detect 1306 an area of an incoming vessel within the predetermined area, a mean flow velocity of blood in the incoming vessel, and a total concentration of hemoglobin. The area of the incoming vessel and the mean flow velocity are based on measurements obtained by ultrasound imaging, and the total concentration of hemoglobin is based on measurements obtained by the plurality of multi-wavelength light pulses. The $MRO_2$ is determined 1308 based on the area of the incoming vessel, the mean flow velocity of blood in the incoming vessel, and the total concentration of hemoglobin using Equation (1) as explained above. The $MRO_2$ is the amount of oxygen consumed in a given tissue region per unit time per 100 g of tissue or of the organ of interest. In typical physiological conditions, since hemoglobin is the dominant carrier of oxygen, the key measure of blood oxygenation is the oxygen saturation of hemoglobin ($sO_2$). The one or more laser pulses are focused by an optical assembly, which typically includes lenses, prisms, and/or mirrors. The optical assembly converges the laser light towards the focal point of the ultrasonic transducer. The focused laser light selectively heats the region of interest, causing the object to expand and produce a pressure wave having a temporal profile that reflects the optical absorption and thermo-mechanical properties of the object. In addition to a single-element, focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one-directional or two-directional sector scanning of the object. The cantilever beam is suspended inside a closed, liquid-filled container, which has an acoustically and optically transparent window on a side of the transducer-light delivery optics assembly. The window is positioned on an object surface and acoustic coupling gel is applied. The received acoustic waves are digitized and the digitized acoustic waves are transmitted to a computer for analysis. An image of the object is then formed from the digitized acoustic waves.

By implementing photoacoustic imaging capabilities on a commercial ultrasound system, ultrasound and photoacoustic pulse sequences may be interleaved to obtain (1) structural images from ultrasound B-mode scans, (2) functional images of total hemoglobin concentration from photoacoustic scans, (3) functional images of hemoglobin oxygen saturation ($sO_2$) from photoacoustic scans, and (4) images of melanin concentration from photoacoustic scans as well. Therefore, photoacoustic imaging will significantly enrich the contrast of ultrasound imaging and provide a wealth of functional information.

A single-RBC photoacoustic flowoxigraphy (FOG) device is provided in another aspect. In this aspect, the device delivers laser pulses of two different wavelengths separated by a pulse separation period of about 20 µs. This separation period is sufficiently brief to enable pulses of two different wavelengths to illuminate the same single moving RBC. The acoustic signals elicited by the single RBC in response to the laser pulses of two different wavelengths may be analyzed using pulse oximetry methods similar to those described herein below to simultaneously determine a variety of functional parameters including, but not limited to: total hemoglobin concentration ($C_{Hb}$), oxygen saturation ($sO_2$), gradient of oxygen saturation ($\nabla sO_2$), flow speed ($V_{flow}$), and metabolic rate of oxygen ($MRO_2$), and any combination thereof.

Single-RBC FOG may be an effective tool for in vivo imaging of the oxygen exchange between single RBCs and their local environments. The optical diffraction-limited lateral spatial resolution and the >100-Hz two-dimensional imaging rate enable resolution of single flowing RBCs in real time. The short, 20 µs, dual wavelength switching time, enables the detection of oxygenation in flowing RBCs. Other time intervals may be used. During fast scanning, this imaging modality maintains the confocal alignment between the optical and acoustic foci. This provides superior SNR compared with pure optical scanning, and may be of great importance for sensitive functional imaging. The single-RBC FOG also has the advantage of label-free imaging, relying on intrinsic optical absorption contrast from $HbO_2$ and Hb. This feature avoids the use of contrast agents that might be chemically toxic, phototoxic, radioactive, or disruptive to the imaging targets. Taking full advantage of the single-RBC FOG, the dynamic processes of single RBCs delivering oxygen to local cells and tissues in vivo at multiple anatomical sites, including the brain, may be directly imaged.

The single-RBC FOG is able to simultaneously measure multiple functional parameters, which include $C_{Hb}$, $sO_2$, $\nabla sO_2$, $V_{flow}$, and $MRO_2$. Such a capability can uncover the relationships between these tightly related parameters, and provide a comprehensive view of cell and tissue oxygenation with high spatiotemporal resolution. Dynamics of single-RBC oxygen release may be imaged under normoxia and during a transition from hypoxia to hyperoxia. Experimental results show that the RBC oxygen delivery may be regulated by $V_{flow}$ and $sO_2$.

Single RBCs, as basic oxygen carriers, play a key role in oxygenating most cells and tissues. To date, the lack of technologies available for direct functional imaging of single RBCs in vivo has been a major limiting factor in studies of oxygen metabolism at high temporal and spatial resolution. The single-RBC FOG demonstrated here has broken through this limitation by directly imaging the oxygen release processes from single RBCs, as well as allowing for simultaneous measurement of $C_{Hb}$, $sO_2$, $\nabla sO_2$, $V_{flow}$, and $MRO_2$. This advance in single-RBC FOG may open new avenues for studying fundamental principles in oxygen metabolism and related diseases. This device may be used in clinical or pre-clinical applications, to diagnose or study some microvascular diseases, such as septic shock, sickle cell anemia, and circulating tumor cells; or some metabolic diseases such as diabetes and cancer.

Figure 19:
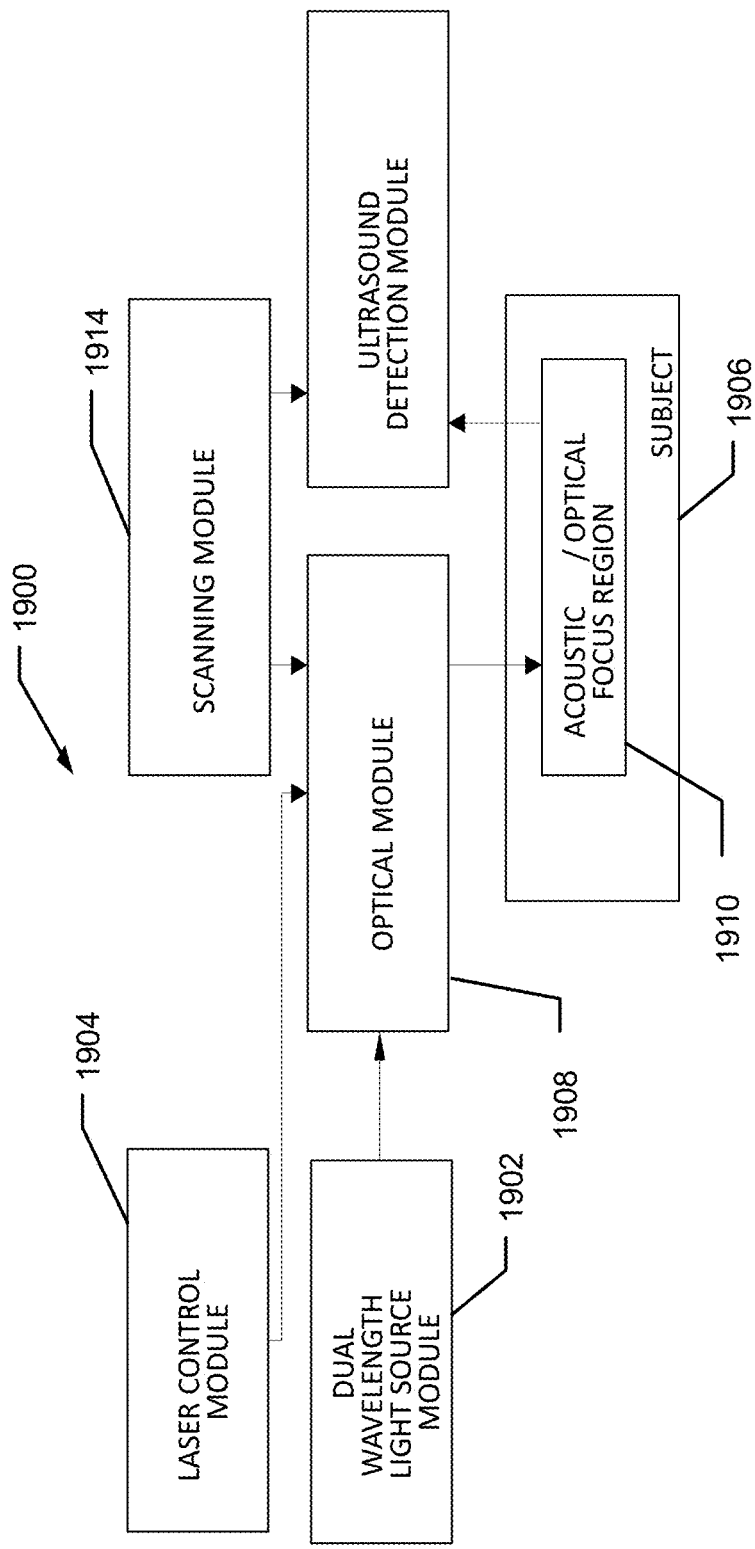
FIG. 19 is a block diagram illustrating the arrangement of modules of a single red blood cell (RBC) photoacoustic flowoxigraphy (FOG) system.

FIG. 19 is a schematic illustration showing the arrangement of the components and devices of the single-RBC photoacoustic flowoxigraphy (FOG) device 1900 in one aspect. The device 1900 may include a dual wavelength light source module to produce a series of isosbestic laser pulses at an isosbestic wavelength, an isosbestic pulse width of less than about 10 ns and an isosbestic pulse repetition rate of at least 2 kHz and a series of non-isosbestic laser pulses at a non-isosbestic wavelength, a non-isosbestic pulse width of less than about 10 ns and a non-isosbestic pulse repetition rate of at least 2 kHz. In an aspect, the isosbestic wavelength may be any wavelength with a hemoglobin absorbance that is essentially equal to an oxyhemoglobin absorbance. Non-limiting examples of suitable isosbestic wavelengths include: 532 nm, 548 nm, 568 nm, 587 nm, and 805 nm. In this same aspect, the non-isosbestic wavelength may be any wavelength with a hemoglobin absorbance that is not equal to the oxyhemoglobin absorbance. In another aspect, the isosbestic wavelength is about 532 nm and the non-isosbestic wavelength is about 560 nm.

In another aspect, the dual wavelength light source module 1902 may include an isosbestic laser (not shown) to produce the series of isosbestic laser pulses and a non-isosbestic laser (not shown) to produce the series of non-isosbestic laser pulses. Any known laser device with the capable of producing laser pulses at the wavelengths, pulse widths, and pulse repetition rates as described herein above may be used. Various suitable laser devices are described herein previously.

Referring again to FIG. 19, the device 1900 may further include a laser control module 1904 to trigger the delivery of each isosbestic laser pulse and each non-isosbestic laser pulse, wherein each isosbestic laser pulse is delivered at a pulse separation period of about 20 µs before or after each adjacent non-isosbestic laser pulse. The 20 µs pulse separation period is sufficiently brief so that both an isosbestic laser pulse and a non-isosbestic laser pulse may illuminate each individual RBC as it moves through a vessel in the subject 1906. In addition, the 20 µs pulse separation period provides sufficient time for each acoustic signal corresponding to each pulse to be emitted and detected without interfering with previous or subsequent acoustic signals induced by previous or subsequent laser pulses. Methods of controlling and timing the operation of the lasers is provided previously herein.

Referring again to FIG. 19, the device 1900 may further include an optical module 1908 to direct the series of isosbestic laser pulses and the series of non-isosbestic laser pulses through an optical focus region 1910 in a cylindrical beam with a beam cross-sectional diameter of less than about 10 µm. The optical focus region, as described previously herein, may typically include a capillary or other vessel or tissue of interest within the subject 1906. In one aspect, the optical module 1908 may include an optical fiber (not shown) connected to the isosbestic laser and the non-isosbestic laser at a first end. The optical fiber may receive both isosbestic and non-isosbestic laser pulses in a combined stream and direct the combined pulse streams to the optical focus region 1910. Any known optical fiber may be included in the optical module 1908 including, but not limited to a single-mode fiber. The optical fiber may further include optical couplers to direct the output of the lasers into the optical fiber.

In another aspect, the optical module 1908 may further include additional optical components (not shown) to focus the laser pulses delivered by the optical fiber into a beam with a beam diameter of less than about 10 µm through the optical focus region 1910. Any known optical components described previously herein may be incorporated into the optical module 1908 including, but not limited to lenses, mirrors, prisms, condensers, and any other suitable known optical component. In one aspect, the optical module 1908 may further include a pair of optical lenses including, but not limited to a pair of achromatic doublets with a numerical aperture in water of about 0.1. In this aspect, the additional optical components maybe operatively attached to the optical fiber at a second end of the optical fiber opposite to the first end of the optical fiber.

Referring again to FIG. 19, the device 1900 may further include an ultrasound detection module 1912 to detect acoustic signals generated within the optical focus region 1910 in response to the series of isosbestic and non-isosbestic laser pulses. The ultrasound detection module may include any ultrasound detector (not shown) capable of detecting an acoustic signal within an acoustic focus region 1910 that is aligned with the optical focus region 1910. Any suitable known ultrasound transducer may be incorporated into the ultrasound detection module including any of the ultrasound transducers described herein previously. In one aspect, the ultrasound detection module 1910 may include a focused ultrasound transducer with a central frequency of about 50 MHz. In this aspect, this focused ultrasound transducer may result in an axial spatial resolution of about 15 µm.

In order to maintain the acoustic and optical focus regions 1910 in an aligned orientation, the optical module 1908 may further include an additional element to reflect the focused laser pulses in a direction that is essentially aligned with the detection axis of the focused ultrasound transducer. In one aspect, the optical module 1908 may further include an acoustically transparent optical reflector to transmit acoustic signals from the acoustic focus region 1910 to the focused ultrasound transducer and to reflect the series of isosbestic and non-isosbestic laser pulses from the optical assembly to the optical focus region 1910.

Figure 20:
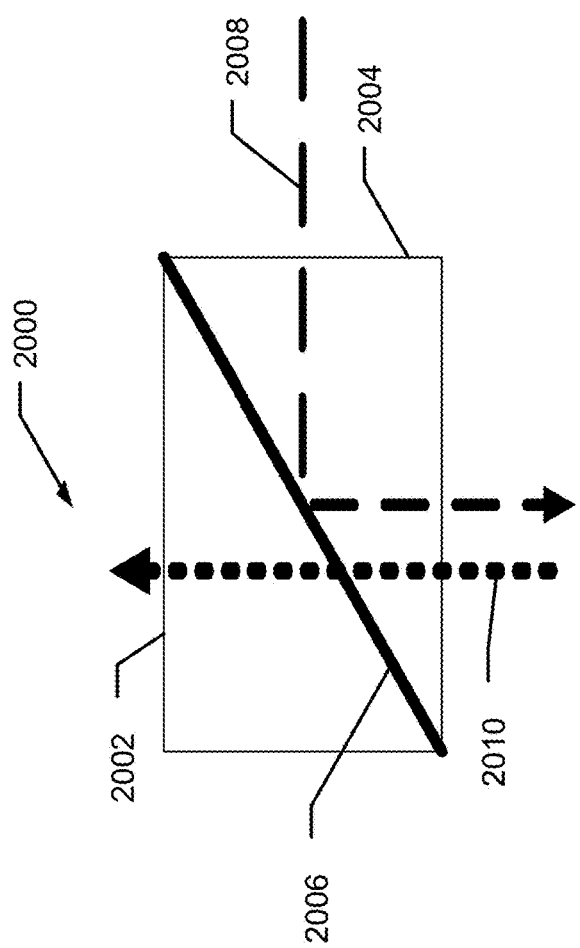
FIG. 20 is an illustration of an acoustically transparent optical reflector in an aspect.

FIG. 20 is a schematic diagram of an acoustically transparent optical reflector focusing assembly 2000 in one aspect. The assembly 2000 may include a first right-angle prism 2002 and a second first right-angle prism 2004 with a sub-micron reflective aluminum coating layer 2006 sandwiched between the two prisms 2002/2004, forming a reflective plane. The aluminum layer 2006 reflects incoming laser pulses 2008 in a downward direction, but also transmits acoustic signals 2010 propagating upward from the optical/acoustic focus region. As a result, the directions of the incoming laser pulses 2008 and the outgoing acoustic signals 2010 are aligned, resulting in a reduced signal-to-noise ratio (SNR).

Referring again to FIG. 19, the device 1900 may further include a scanning module 1914 to move the optical module 1908 and the ultrasound detection module 1912 in a linear scanning pattern. In this arrangement, the device 1900 may obtain imaging data over a linear transect that may be used to obtain a two-dimensional plane image corresponding to a vertical slice extending the length of the linear scan and the depth corresponding to the focus range of the ultrasound transducer of the ultrasound detection module 1912. Because both the optical module 1908 and the ultrasound detection module 1912 are translated together in a synchronized manner, the alignment of the laser pulses and the acoustic signals is maintained, resulting in higher quality imaging data as discussed herein previously. In order to obtain images in real time, the scanning module may have a scanning rate of at least 100 linear scans per second. In one aspect, the scanning module 1912 may include any linear scanner described herein previously capable of rapid scanning. In another aspect, the scanning module 1912 may include a voice-coil scanner with a scanning rate of at least 100 linear scans per second.

Figure 14:
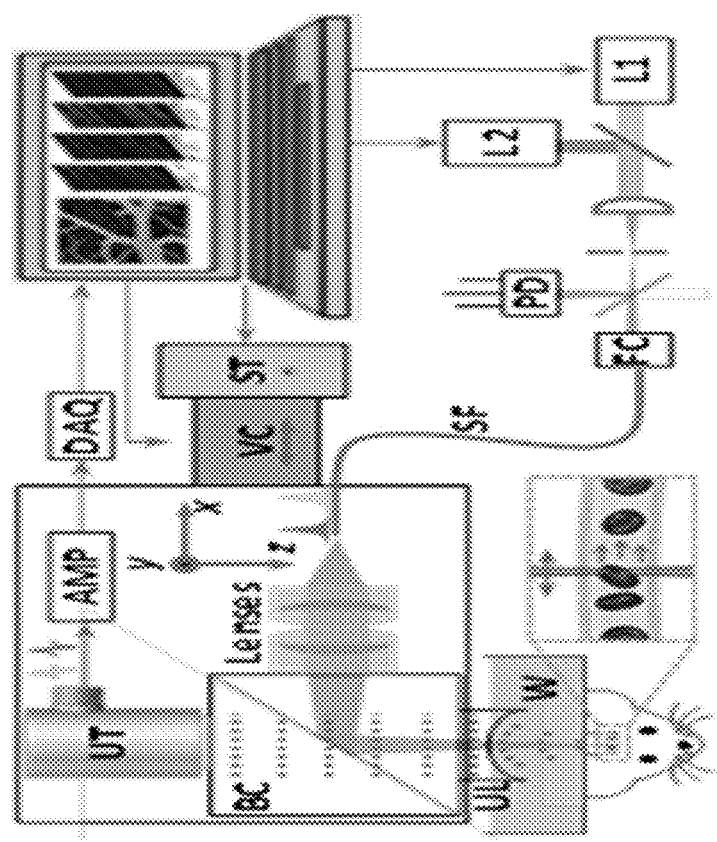
FIG. 14 is a schematic diagram of a single red blood cell (RBC) photoacoustic flowoxigraphy (FOG) device.

FIG. 14 is a schematic diagram illustrating the arrangement of elements and components of a single-RBC photoacoustic flowoxigraphy (FOG) device in one aspect. In this aspect, two lasers L1 and L2 are employed to periodically generate two 20-µs-apart laser pulses at 560 nm (non-isosbestic wavelength) and 532 nm (isosbestic wavelength), respectively with pulse widths of less than 10 ns. Both lasers L1 and L2 operate at a 2-kHz pulse repetition rate. Other wavelengths may also be used as long as the deoxy-hemoglobin and oxy-hemoglobin have different absorption coefficients.

The two laser beams are merged into a single-mode optical fiber SF by way of a fiber coupler FC and then delivered to a PA probe. The energy of each laser pulse is detected by a biased photodiode PD for pulse-to-pulse calibration. The laser beam from the fiber SF is focused onto targets through a pair of optical lenses (numerical aperture in water: 0.1), an acoustic-optical beam combiner BC, and an ultrasound lens UL. The optical lenses can be adjusted to accurately align the acoustic and optical foci. The acoustic-optical beam combiner BC, which is composed of two prisms and a coated aluminum layer in the middle, reflects light, but transmits sound. The tight optical focus provides a 3.4-µm lateral spatial resolution. Laser-excited PA signals are collected by the ultrasound lens UL, transmitted through the acoustic-optical beam combiner BC, and detected by a high-frequency ultrasound transducer UT.

By way of non-limiting example, the ultrasound transducer may be a model V214 Olympus NDT, 50 MHz central frequency transducer which provides an axial spatial resolution of 15 µm. The PA signals are amplified by an amplifier AMP, filtered and digitized at 500 MHz by a digitizer DAQ.

Referring again to FIG. 14, the PA probe is mounted onto a fast voice-coil linear scanner VC to enable acquisitions of at least 100 cross-sectional (B-scan) images per second. Mechanically scanning the entire PA probe maintains the acoustic-optical confocal alignment, and therefore achieves higher signal-to-noise ratio (SNR) than pure optical scanning in a fixed acoustic focus. A field-programmable gate array card (PCI-7830R, National Instrument, not shown) may be programmed to synchronize the trigger signals and motion control commands in an aspect. By fast scanning the PA probe along a segment of a capillary, single RBCs flowing through the field of view may be imaged, and the amount of oxygen bound to each RBC may be directly measured.

At each position, the two laser pulses sequentially excite nearly the same region of the target to acquire two depth-resolved PA signals (A-lines). Taking 10-mm·s$^{-1}$ flow speed as an example, the target may move 0.2 µm during the wavelength switching, which is a small distance relative to the spatial resolution of the device. As a result, image artifacts due to movement of the individual RBCs during wavelength switching are minimal. Because $HbO_2$ and Hb have molar extinction coefficients of different spectral characteristics, and because PA signals are linearly related with the concentrations of $HbO_2$ and Hb at low excitation laser energy (<100 nJ per pulse), the relative concentrations of $HbO_2$ and Hb may be computed from the PA signals of the same RBC excited at 532 nm and 560 nm pulses. The relative $C_{Hb}$ and $sO_2$ of single RBCs may readily be calculated from the $HbO_2$ and Hb concentrations using methods similar to those described herein previously. To quantify the local oxygen delivery, the average hemoglobin concentration $\langle C_{Hb}\rangle$ may be computed by averaging $C_{Hb}$ over the imaged segment of a capillary of the subject.

In an aspect, when $sO_2$ reaches a dynamic equilibrium, the amount of oxygen delivered by RBCs may be assumed to be equal to the oxygen consumed by the perfused tissues; hence, the $MRO_2$ can be determined from Eqn. (2):

$$MRO_2 = k \cdot \langle C_{Hb} \rangle \cdot \nabla sO_2 \cdot V_{flow} \quad \text{Eqn. (2)}$$

where k is a constant coefficient related to the hemoglobin oxygen binding capacity and the weight of the local tissue surrounding a unit length of the capillary. Note that, the $\nabla sO_2$, $V_{flow}$, and $MRO_2$ represent the averages of the capillary segment within the field of view.

The embodiments described herein relate to noninvasively imaging capillaries. Some of the embodiments relate to microscopic photoacoustic imaging using focused optical illumination and focused ultrasonic detection. For example, an embodiment performs optical-resolution photoacoustic microscopy (OR-PAM), which facilitates providing a lateral resolution of 5 micrometers ($\mu m$) and a maximum imaging depth of greater than 0.7 millimeters (mm) based on endogenous optical absorption contrast. In vivo images of healthy capillary networks and laser coagulated microvessels in mouse ears, for example, are demonstrated as examples of applications of OR-PAM in biomedical research.

In an embodiment, the lateral resolution is dominantly determined by the optical focus. A tightly focused optical illumination produces a local temperature rise due to light absorption. The temperature rise leads to thermal expansion, which results in photoacoustic emission. The photoacoustic emission may be detected by a high-frequency large numerical-aperture spherically focused ultrasonic transducer that is coaxial and confocal with the light focusing system. The photoacoustic emission may also be measured by an ultrasonic transducer array, a phase sensitive optical coherence tomography apparatus, a laser optical interferometer, and/or a capacitive surface displacement sensor. By focusing light to a focal spot of several micrometers in diameter, embodiments of the invention significantly improve the image resolution of photoacoustic microscopy of biological tissue or other optically scattering media. It combines the high spatial resolution of optical confocal microscopy and the high optical absorption contrast of photoacoustic tomography.

The embodiments described herein provide for reflection-mode microscopic photoacoustic imaging using focused optical illumination. Embodiments of the invention use a nearly diffraction-limited focused optical illumination to achieve high spatial resolution. Embodiments of the invention use a confocal arrangement between the optical focus and the ultrasonic focus of a high-frequency large numerical-aperture (NA) spherically focused ultrasonic transducer to achieve high sensitivity. The ultrasonic transducer may be replaced with another detector capable of measuring local thermal expansion. By tightly focusing light, the lateral resolution limitations of existing photoacoustic microscopy based on the resolution of the ultrasonic focusing system may be overcome. In addition, because a photoacoustic signal is proportional to the optical fluence at the target, the currently described embodiments require only a low laser pulse energy and, hence, may be made relatively compact, fast, and inexpensive. In the exemplary embodiment, a laser pulse energy of approximately 100 nanojoules (nJ) may be used.

Moreover, exemplary embodiments utilize optical focusing and time-resolved detection of laser-induced pressure waves to obtain three-dimensional images of the distribution of optical-absorption contrast within a sampling volume. The exemplary embodiments provide non-invasive imaging of scattering media, such as, but not limited to, biological tissue in vivo. The exemplary embodiments provide non-invasive imaging up to approximately one optical transport mean free path deep. For most biological tissue, an optical transport mean free path is approximately 1.0 millimeter (mm). In the exemplary embodiment, resolution on the order of 1.0 micrometer ($\mu m$) is attainable. Further, the exemplary embodiment images optical-absorption contrast in biological tissue up to approximately 0.7 mm deep with a lateral resolution of approximately 5.0 $\mu m$. In embodiments of the invention, a large numerical-aperture (NA) spherically focused ultrasonic transducer is used in a confocal coaxial arrangement with the light focusing optics to facilitate providing high axial resolution of between 10.0 and 15.0 $\mu m$.

An imaging procedure, which uses a confocal photoacoustic imaging system, is one of the possible embodiments and is aimed at medical and biological applications. The presently described embodiments are complementary to the structural information that may be obtained from pure optical and ultrasonic imaging technologies and may be used for diagnostic, monitoring or research purposes. Applications of the technology include, but are not limited to, the imaging of arteries, veins, capillaries (the smallest blood vessels), pigmented tumors such as melanomas, and sebaceous glands in vivo in humans or animals. The presently described embodiments may use the spectral properties of intrinsic optical contrast to monitor blood oxygenation (oxygen saturation of hemoglobin), blood volume (total hemoglobin concentration), and even the metabolic rate of oxygen consumption; it may also use the spectral properties of a variety of dyes or other contrast agents to obtain additional functional or molecular-specific information. In other words, the presently described embodiments are capable of functional and molecular imaging. Further, the presently described embodiments may be used to monitor possible tissue changes during x-ray radiation therapy, chemotherapy, or other treatment. In addition, presently described embodiments may also be used to monitor topical application of cosmetics, skin creams, sun-blocks or other skin treatment products. The presently described embodiments, when miniaturized, may also be used endoscopically, e.g., for the imaging of atherosclerotic lesions in blood vessels.

Further, the presently described embodiments provide a method of characterizing a target within a tissue by focusing one or more laser pulses on the region of interest in the tissue so as to penetrate the tissue and illuminate the region of interest, receiving the pressure waves induced in the object by optical absorption using one or more ultrasonic transducers that are focused on the same region of interest, and recording the received acoustic waves so that the structure or composition of the object may be imaged. The one or more laser pulses are focused by a microscope objective lens or a similar tightly focusing optical system, which typically includes an optical assembly of lenses and/or mirrors, which converges the one or more laser pulses towards the focal point of the ultrasonic transducer. The focusing device may also use one or more optical spatial filters, which may be a diaphragm or a single-mode fiber, to reduce the focal spot of the optical system to the smallest possible size so that the highest possible spatial resolution may be achieved. The focused one or more laser pulses selectively heat the region of interest, causing the object to expand and produce a pressure wave whose temporal profile reflects the optical absorption and thermo-mechanical properties of the target. Alternatively, an annular array of ultrasonic transducers may be used along the tissue to enhance a depth of field of an imaging system by using synthetic aperture image reconstruction. The signal recording includes digitizing the received acoustic waves and transferring the digitized acoustic waves to a computer for analysis. The image of the object is formed from the recorded acoustic waves.

In addition, the presently described embodiments may also include an electronic system in communication with the focusing device, the one or more ultrasonic transducers, or a combination thereof. In one embodiment, the electronic system includes an XYZ or circular scanner or scanners, an amplifier, a digitizer, a laser wavelength tuning electronics, a computer, a processor, a display, a storage device, or combination thereof. One or more component of the electronic system may be in communication remotely with the other components of the electronic system, the apparatus, or both.

Figure 21:
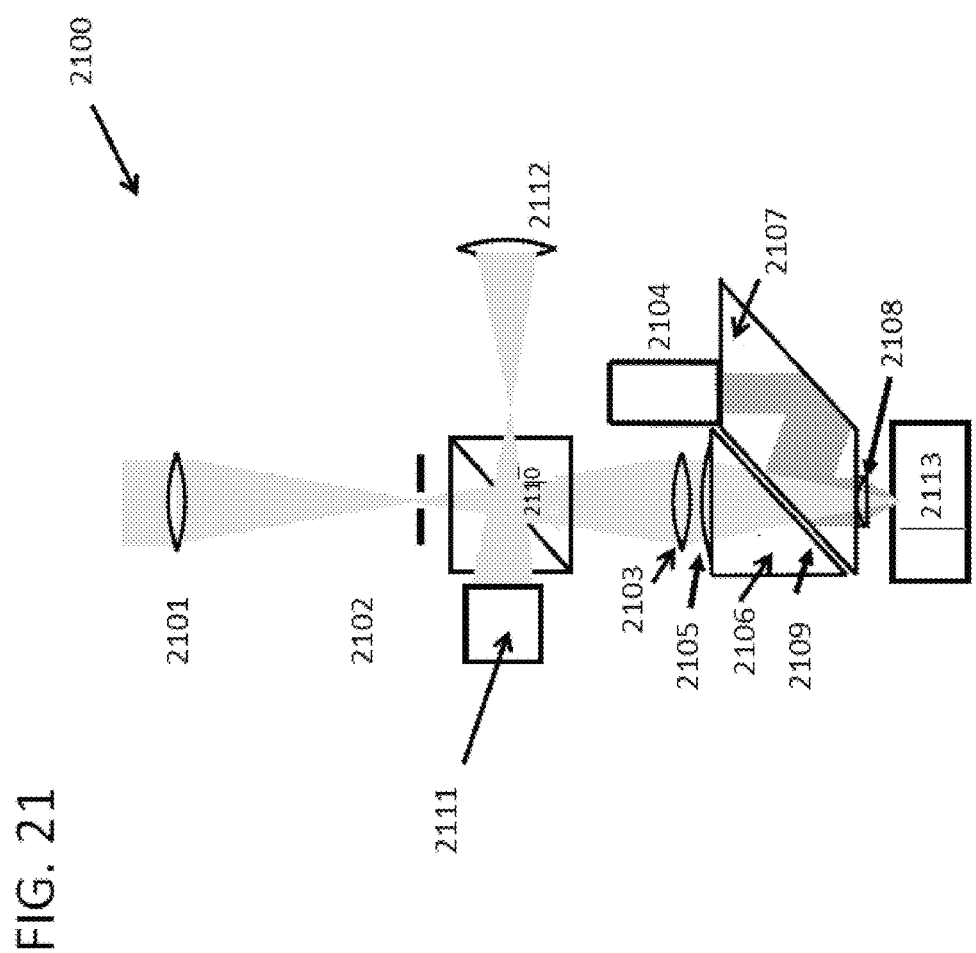
FIG. 21 is a diagram of a photoacoustic sensor that may be used with an imaging system.

FIG. 21 shows a schematic of an exemplary focusing assembly 2100 which uses the confocal photoacoustic microscopy method. The light out of the dye laser is focused by a condenser lens 2101 on a diaphragm (pinhole) 2102 for spatial filtering. Sampling beam splitter 2110 is used to monitor the laser output power through photo-detector 2111 and to optically image the object surface through eyepiece or aligning optics 2112 for alignment. The light coming out of the spatial filter is focused by microscope objective lens 2103 onto object 2113 through beam separating element 2106, 2107, 2109, and acoustic lens 2108. Correction lens 2105 placed on top of the beam separation element compensates for the aberrations introduced by the prisms and the acoustic lens. The distance between the pinhole and the objective lens is approximately 400 millimeters (mm), which gives an optical focusing spot size of approximately 3.7 micrometers (μm) in diameter and a focal zone of approximately 200 μm in water. The laser pulse energy measured after the objective lens is approximately 100 nanojoules (nJ). The beam separation element consists of an isosceles triangular prism 2106 with an apex angle of approximately 52.5° and a rhomboidal 52.5° prism 2107. Prisms 2106 and 2107 are adjoined along the diagonal surfaces with a gap of approximately 0.1 mm in between. Gap 2109 is filled with an optical refractive-index-matching, low-acoustic-impedance, nonvolatile liquid such as 1000 cSt silicone oil, commercially available from Clearco Products. The silicone oil and the glass have a good optical refractive index match (glass: 1.5; silicone oil: 1.4) but a large acoustic impedance mismatch (glass: $12.1 \times 10^6$ N·s/m$^3$; silicone oil: $0.95 \times 10^6$ N·s/m$^3$). As a result, the silicone oil layer is optically transparent but acted as an acoustic reflector. The photoacoustic signal emitted by the target is transformed by the acoustic lens 2108, having a radius of curvature of approximately 5.2 mm, a diameter of approximately 6.35 mm, a NA of approximately 0.46 in water, and an ultrasonic focal spot size of approximately 27 μm, into a plane elastic wave in rhomboidal prism 2107 and is then detected by the high-frequency direct-contact ultrasonic transducer 2104 such as a model V2012-BC transducer, commercially available from Panametrics-NDT with a center frequency of approximately 75 MHz, a bandwidth of approximately 80%, and an active element diameter of approximately 6.35 mm. Within the bandwidth of the ultrasonic transducer 2104, ultrasonic absorption in silicone oil is high enough to dampen ultrasonic reverberations in the matching layer and thus minimize interferences to the image.

Figure 22:
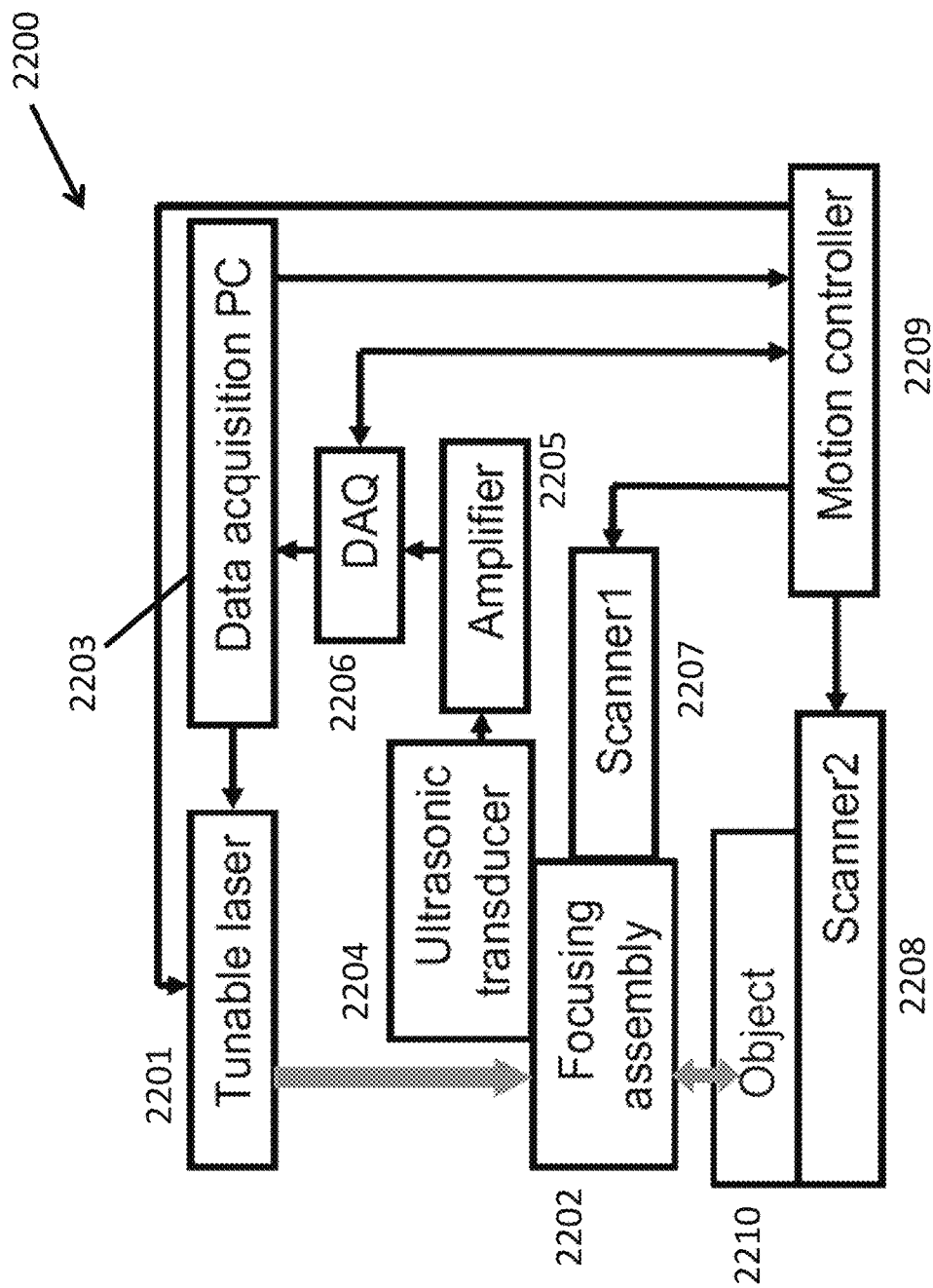
FIG. 22 is a block diagram of a system that uses confocal photoacoustic microscopy.

FIG. 22 is a block diagram of a system 2200 based on confocal photoacoustic microscopy, which is capable of contour scanning and quantitative spectroscopic measurement. The system includes a pulsed tunable laser 2201 including a tunable laser pumped by a Q-switched laser, a focusing assembly 2202, one or more ultrasonic transducers 2204, and an electronic system (not illustrated). The electronic system includes data acquisition personal computer (PC) 2203, motion controller 2209, first and second scanners 2207 and 2208, amplifier 2205, and data acquisition subsystem (DAQ) 2206, which includes a signal conditioner and a digitizer. Focusing assembly 2202 receives one or more laser pulses and focuses the one or more laser pulses into an area inside the sample object 2210 so as to penetrate the tissue and illuminate the region of interest. The one or more ultrasonic transducers 2204 are focused on the same the region of interest and receive the acoustic or pressure waves induced in the region of interest by the one or more laser pulses. The electronic system records and processes the received acoustic or pressure waves. The laser pulse generation, data acquisition, and object scanning are synchronized with the pulses produced by the motor controller at programmed locations of the laser focus with respect to object 2210. As described above, the focusing assembly 2202 includes an optical assembly of lenses and/or mirrors that focuses one or more laser beams on the object 2210 in such a way that the focal point of the optical focusing device coincides with that of the one or more ultrasonic transducers 2204.

The focusing assembly 2202 is placed on an XYZ translation stage to perform raster scanning along the object surface with simultaneous adjustment of the sensor's axial position to compensate for the curvature of the object surface. Other embodiments may use different ways of image formation, which include, but are not limited to, circular scanning, sector scanning, optical scanning, electronic focusing using a transducer array, and array-based image reconstruction. The recorded pressure-wave time histories are displayed by the computer 2203 versus the focusing assembly position to construct a three dimensional image of the distribution of the optical contrast within the tissue, i.e., a three dimensional tomographic image of the object 2210.

System 2200 employs a tunable dye laser 2201, such as a model CBR-D laser, commercially available from Sirah, pumped by a neodymium-doped yttrium lithium fluoride (Nd:YLF) laser, such as the INNOSLAB laser, commercially available from Edgewave, as the irradiation source. The laser pulse duration is approximately 7 nanoseconds (ns) and the pulse repetition rate, which is controlled by the external triggering signal, is as high as approximately 2 kilohertz (kHz). In alternative embodiments, a plurality of sources of penetrating radiation, which may be confined to or concentrated in a small volume within the object 2210, may be used. Such sources include, but are not limited to, pulsed lasers, flash lamps, other pulsed electromagnetic sources, particle beams, or their intensity-modulated continuous-wave counterparts.

The one or more focused short laser pulses are delivered to an object 2210 (e.g., human or animal body, tissue or organ) under investigation, where a small area of the object 2210 inside the focal area of the ultrasonic transducer 2204 is illuminated. The laser wavelength is selected as a compromise between the desired light penetration depth and the contrast between the structures of interest and the surrounding medium. Light absorption by the internal structures causes a transient temperature rise which, due to thermoelastic expansion of the medium, produces elastic waves that may travel through the medium.

High-frequency ultrasonic waves generated in tissue by the laser pulse are recorded and analyzed by a PC 2203 to form a three-dimensional image. The shape and dimensions of the optical-contrast structures are generally determined from the temporal profile of the laser-induced ultrasonic waves and the position of the focusing assembly 2202. Ordinarily, a raster scan by the focusing assembly 2202 is used to form a three-dimensional image. However, a transducer array may be used to reduce the time of scanning and the total light exposure. When the tissue under investigation is an internal organ, the optical fiber and ultrasonic transducer 2204 may be incorporated in an endoscope and positioned inside the body. The following examples will be provided for the purpose of illustrating various embodiments of the invention and are not meant to limit the present invention in any fashion.

As illustrated in FIGS. 23, 24, 25, and 26, the presently described embodiments provide an optical resolution confocal microscopic photoacoustic imaging technology to image biological tissues in vivo. The exemplary embodiment has a lateral resolution as high as approximately 5 μm and a maximum imaging depth of approximately 0.7 mm. In alternative embodiments, the image resolution may be further improved by increasing the frequency of the ultrasonic transducer and the numerical aperture of the optical objective lens perhaps at the cost of imaging depth. The photoacoustic images shown in FIGS. 32,33, 34, 35, and 36 were obtained with minimal signal averaging and, therefore, could be further improved by averaging, at the expense of data acquisition time, in another embodiment of the invention. The current imaging speed is limited by the pulse repetition rate of the laser. Because lasers with pulse repetition rates of up to 100 KHz are now available, other embodiments involve faster photoacoustic imaging, which can reduce motion artifacts, and extensive signal averaging.

The presently described embodiments include any realization of light focusing using any kind of mirrors, lenses, fibers, and diaphragms that may produce well focused (preferably diffraction-limited) illumination confined to the focal area of the focused ultrasonic transducer. The presently described embodiments also cover any confocal photoacoustic techniques with any light delivery and detection arrangements in which the lateral resolution is defined by the focusing of the incident radiation rather than the acoustic detection unit.

One or more of the following embodiments may be used to implement laser focusing for the purpose described herein: (1) an optical microscope objective lens that focuses a well-collimated single-mode laser beam into a nearly diffraction-limited point, (2) an objective lens that forms an image of a small pinhole on the region of interest, (3) a focusing system in which a single-mode optical fiber is used instead of pinhole, (4) a focusing system in which an oscillating mirror scans the optical focus rapidly within the larger focal area of the ultrasonic transducer. The following embodiments, and further alternative embodiments, may also be used to implement laser focusing for further, undescribed purposes. Various examples of the focusing assembly will now be described in reference to FIGS. 23, 24, 25, 26, 27, 28, 29, and 30, wherein the focusing assembly includes, for example, an optical focusing device, and one or more ultrasonic transducers in the piezoelectric, optical, or another form.

Figure 23:
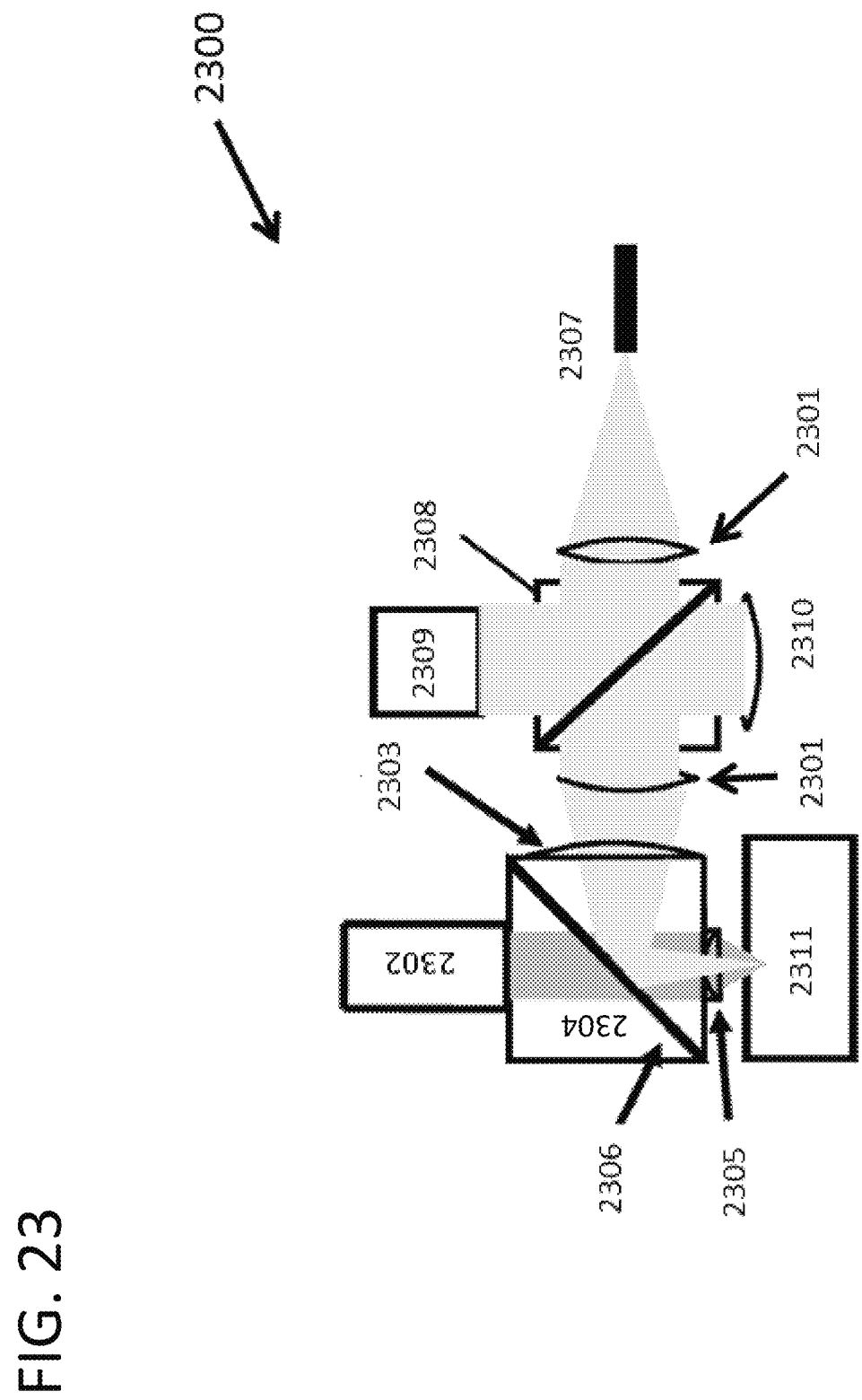
FIG. 23 is a diagram of a photoacoustic sensor that may be used with the imaging system shown in FIG. 22.

FIG. 23 is a diagram of a focusing assembly 2300 of imaging system 2200 (shown in FIG. 22). A custom-made cubic beam splitter or right-angle prism 2304 with a submicron reflective aluminum coating layer 2306 sandwiched between the two prisms is used to couple the optical and ultrasonic radiations. A pair of optical objective lenses 2301 focuses the laser light from the single-mode optical fiber 2307 onto the region of interest inside the object 2311, where metal coating 2306 is used to reflect the optical beam. A sampling beam splitter 2308 is placed between the objective lenses 2301 to monitor the laser output power with a photo-detector 2309 and to view the object surface for alignment with an eyepiece or aligning optics 2310. Ultrasonic radiation emitted by the object 2311 passes through an acoustic lens 2305, the aluminum optical reflector 2306, and reaches an ultrasonic transducer 2302.

Figure 24:
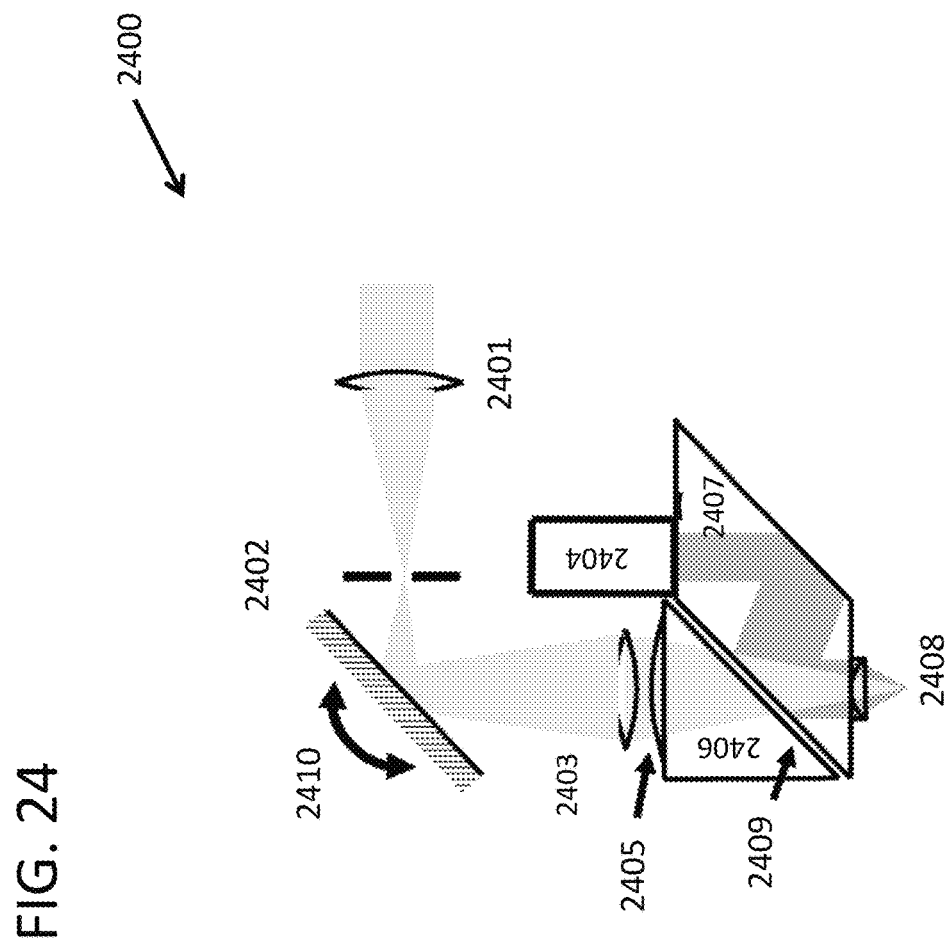
FIG. 24 is a diagram of an alternative photoacoustic sensor that may be used with the imaging system shown in FIG. 22.

FIG. 24 is a diagram of a focusing assembly 2400 of imaging system 2200 (shown in FIG. 22). A laser pulse from a pulse laser is focused by a condenser lens 2401 on a diaphragm 2402 for spatial filtering. The light coming out of the spatial filter 2402 is reflected by an oscillating mirror 2410, which performs fast optical scanning within the wider focal area of an ultrasonic transducer 2404. The laser beam is focused into an object by a microscope objective lens 2403 through a beam splitting element 2406, 2407, 2409 and an acoustic lens 2408. A thin plano-convex optical lens 2405 is placed on top of the beam splitting element 2406, 2407, 2409 to compensate for the aberrations introduced by the prisms 2406 and 2407 and the acoustic lens 2408. The beam splitting element 2406, 2407, and 2409 consists of an isosceles triangular prism 2406 with an apex angle of 52.5° and a rhomboidal 52.5° prism 2407. Prisms 2406 and 2407 are adjoined along the diagonal surfaces but are separated by a thin layer of refractive-index-matching, low-acoustic-impedance, and nonvolatile liquid, such as a low-molecular-weight silicone oil 2409. The photoacoustic signal emitted by the object is transformed by the acoustic lens 2408 into a plane elastic wave in rhomboidal prism 2407. Ultrasonic reflection from the boundary of silicone oil 2409 converts at least 98% of the energy of the incident longitudinal wave into that of a shear wave, which is transformed back into a longitudinal wave on the free surface of rhomboidal prism 2407 and then detected by high-frequency direct-contact ultrasonic transducer 2404. Because the acoustic focus is generally several times wider than the optical focus, taking advantage of fast optical scanning in this embodiment may significantly decrease the image acquisition time.

Figure 25:
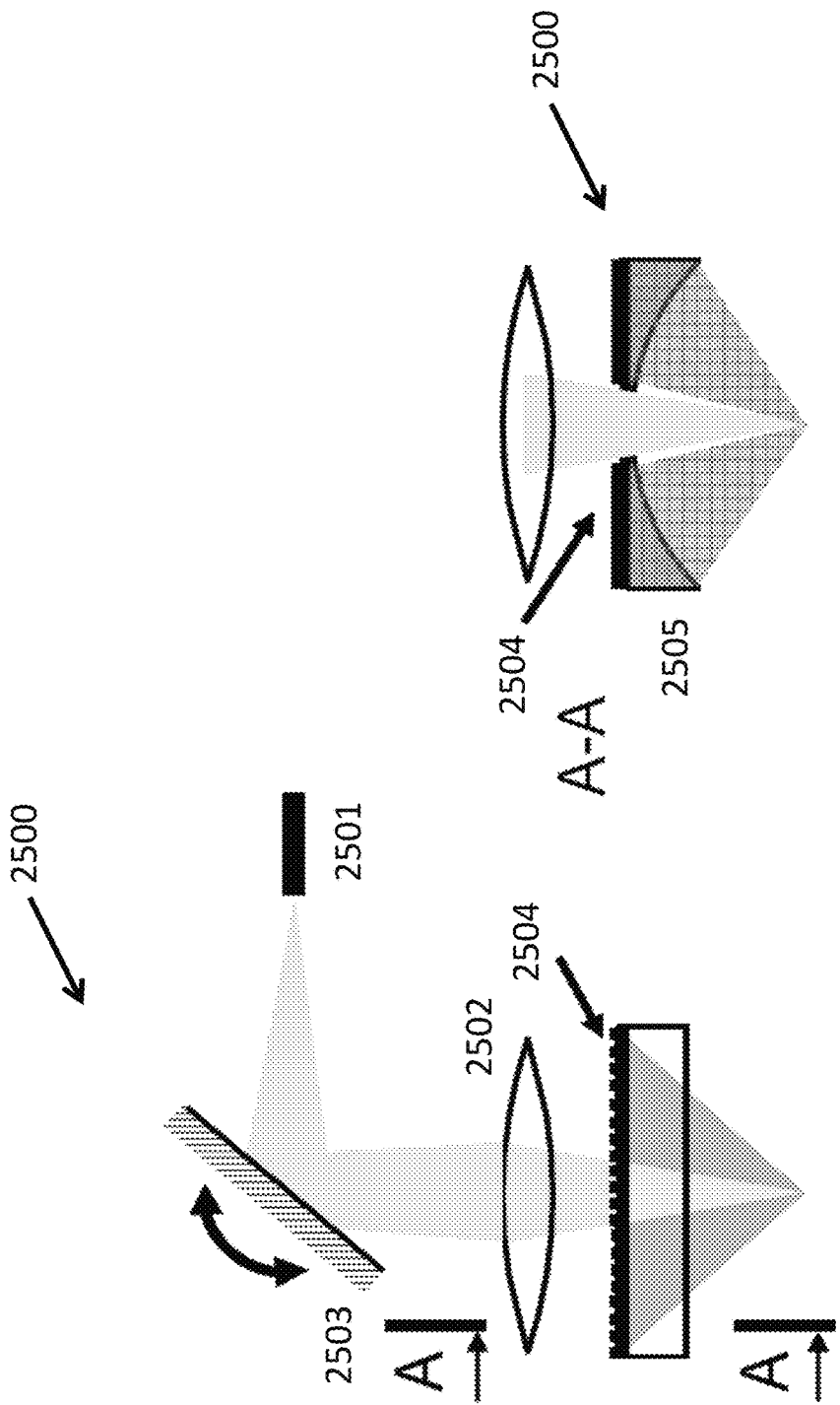
FIG. 25A is a schematic diagram of a second alternative photoacoustic sensor that may be used with the imaging system shown in FIG. 22.
FIG. 25B is a cross-sectional schematic diagram of the second alternative photoacoustic sensor shown in FIG. 25A.

FIG. 25 is a diagram of a focusing assembly 2500 of imaging system 2200 (shown in FIG. 22). An optical objective lens 2502 focuses the output aperture of a single-mode optical fiber 2501 into the object through the optically clear slit window in a one-dimensional ultrasonic array transducer 2504 placed on an optically transparent substrate 2505. Substrate 2505 serves as a wave-guide for acoustic waves and may have a cylindrical focus acoustic lens on its outer surface. The light coming out of the spatial filter is reflected by an oscillating mirror 2503, which performs fast optical scanning. Ultrasonic radiation emitted by the object is collected by ultrasonic transducer array 4. A multiple-element piezoelectric transducer array 2504 may accelerate the image acquisition time in one dimension owing to the electronic focusing of the transducer array 2504. The acoustic focus provided by assembly 2500 follows the focal position of the laser beam without mechanically scanning the ultrasonic transducer 2504 over the object. Three-dimensional images may be acquired by mechanically translating the focusing assembly perpendicularly to the slit.

Figure 26:
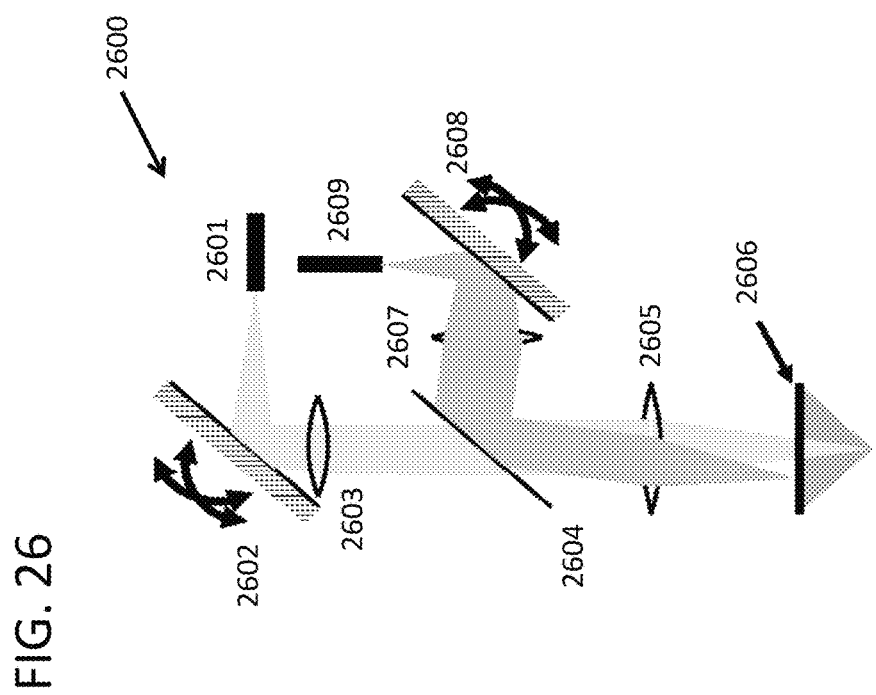
FIG. 26 is a schematic diagram of a third alternative photoacoustic sensor that may be used with the imaging system shown in FIG. 22.

FIG. 26 is a diagram of a focusing assembly 2600 of imaging system 2200 (shown in FIG. 22). The light output from a single-mode optical fiber 2601 is reflected by a mirror scanner 2602, collimated by an optical objective or excitation lens 2603, passed through a dichroic mirror 2604, and then focused by another objective lens 2605 on a region of interest through a Fabry-Perot etalon 2606, which is acoustically coupled to the object. Mirror scanner 2602 performs rapid 2D raster scanning of the object by sweeping the excitation laser beam. The photoacoustic wave from the object causes a transient strain distribution in Fabry-Perot etalon 2606, which shifts its resonance wavelengths. Another laser (probing laser) 2609 working at a different optical wavelength scans over Fabry-Perot etalon 2606 through a second mirror scanner 2608, a second objective lens 2607, and dichroic mirror 2604 to read the strain distribution in Fabry-Perot etalon 2606. The strain is then converted into the photoacoustic pressure distribution. In the exemplary embodiment, no mechanical scanning is necessary to form a 3D image of the object.

Figure 27:
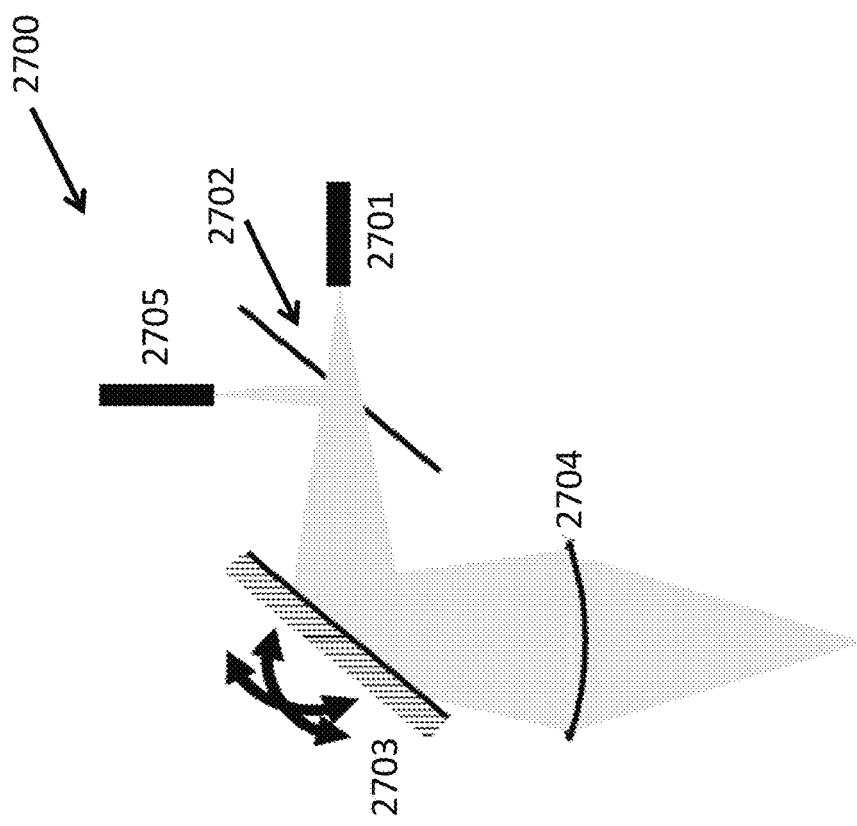
FIG. 27 is a schematic diagram of a fourth alternative photoacoustic sensor that may be used with the imaging system shown in FIG. 22.

FIG. 27 is a diagram of a focusing assembly 2700 of imaging system 2200 (shown in FIG. 22). An optical objective lens 2704 focuses the output aperture of a single-mode optical fiber 2701 into a region of interest in an object to excite photoacoustic waves. A 2D mirror scanner 2703 is introduced in the optical path to perform 2D scanning of the object. A phase-sensitive optical coherence tomography (OCT) system 2705 working at a different optical wavelength is focused on the same region of interest by the optical objective lens 2704 and 2D mirror scanner 2703. The two light beams of different wavelengths are coupled by a dichroic mirror 2702. The phase-sensitive OCT system measures, within the optical focal spot inside the object, the photothermal effect due to absorption of the laser pulse. The photothermal effect in the object is measured before pressure waves propagate to the surface of the object. In the exemplary embodiment, focusing assembly 2700 forms a 3D image without translating the objective lens 2704 and does not require direct contact with the object. Correspondingly, it may be potentially very fast and may be used where non-contact imaging is preferred.

Figure 28:
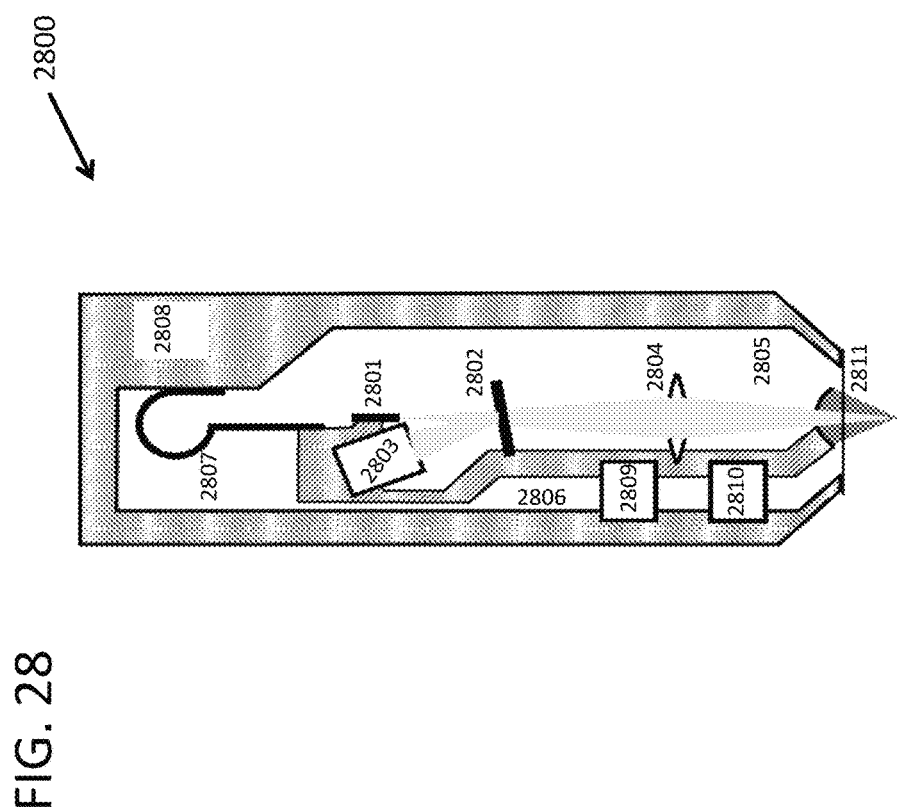
FIG. 28 is a diagram of a fifth alternative photoacoustic sensor that may be used with the imaging system shown in FIG. 22.

FIG. 28 is a diagram of an alternative embodiment of the focusing assembly 2800 suitable for hand-held operation. An optical objective lens 2804 images the aperture of a single-mode optical fiber 2801 onto the region of interest in the object through an optically clear window 2811 in a spherically focused ultrasonic transducer 2805. A sampling beam splitter 2802 reflects a small portion of the incident light to monitor the laser output power with a photo-detector 2803. The ultrasonic radiation emitted by the object is received by the ultrasonic transducer 2805. The photoacoustic assembly is mounted on a pendulum 2806, which is attached to a frame 2808 through a flexible mount, such as a flat spring 2807. The frame 2808 is water-tight and contains optically transparent acoustic coupling fluid, such as water, for light delivery and acoustic coupling. Moved by an actuator 2809, pendulum 2806 may perform sector scanning of the object rapidly. A position sensor 2810 monitors the position of the optical focus and is used to synchronize the pulse laser so that image distortion due to varying scanning velocity is minimized.

Figure 29:
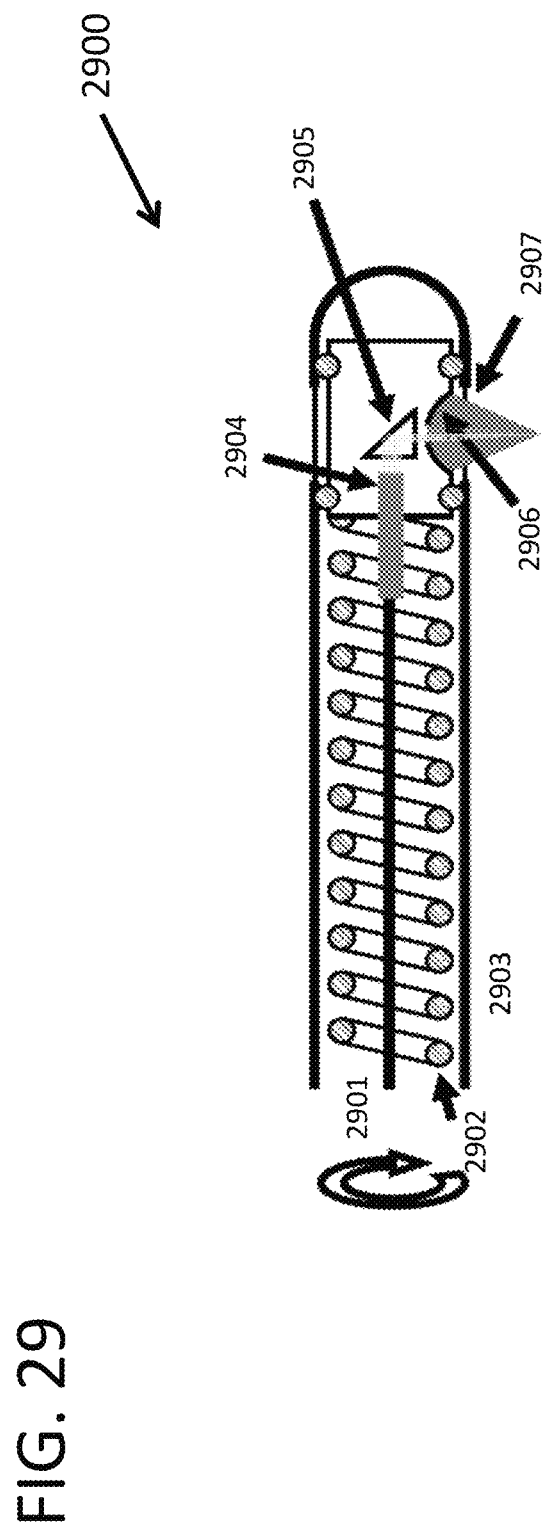
FIG. 29 is a schematic diagram of a sixth alternative photoacoustic sensor that may be used with the imaging system shown in FIG. 22.

FIG. 29 is a diagram of another alternative embodiment of a focusing assembly 2900 suitable for applications inside body cavities such as inter-vascular imaging. A laser pulse delivered by a single-mode fiber 2901 is focused on the region of interest in the object by an optical lens assembly 2904 through an optically clear window 2907 in a spherically focused ultrasonic transducer 2906. Ultrasonic transducer 2906 together with a right-angled prism 2905 is connected to a flexible shaft 2902 located inside a catheter 2903. Optically and acoustically transparent circular window 2907 allows the optical beam and ultrasonic radiation to pass freely to and from the object. Photoacoustic images are formed by rotating the shaft 2902 with respect to the axis of the catheter 2903 and axially translating the catheter 2903.

Figure 30:
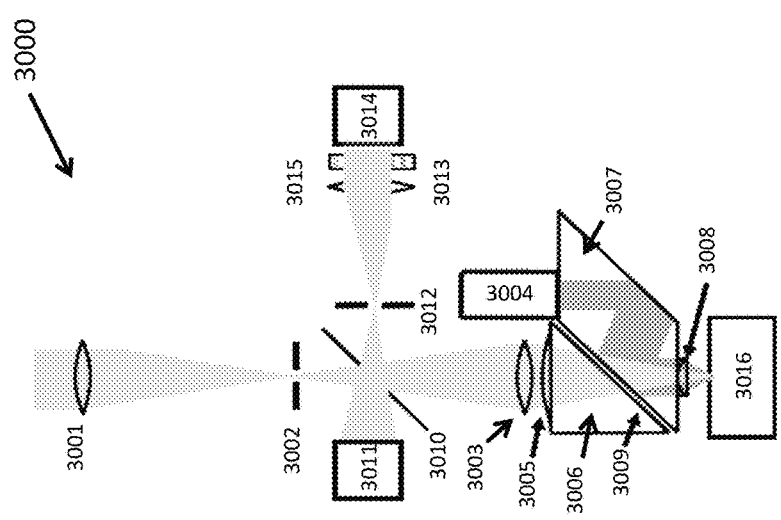
FIG. 30 is a schematic diagram of a seventh alternative photoacoustic sensor that may be used with the imaging system shown in FIG. 22.

FIG. 30 is a block diagram of another alternative embodiment of a focusing assembly 3000 which uses the confocal photoacoustic microscopy method simultaneously with optical confocal microscopy. The light coming out of the pulsed laser is focused by a condenser lens 3001 on a diaphragm (pinhole) 3002 for spatial filtering. A dichroic beam splitter or mirror 3010 is used to monitor the laser output power with a photo-detector 3011 and to form an optical fluorescence confocal image of the object 3016. The optical fluorescence confocal imaging portion consists of a pinhole, or diaphragm, 3012, a focusing system or lens 3013, a low pass optical filter 3015, and a photo-detector (such as a photomultiplier) 3014. The light coming out of the spatial filter 3002 is focused by a microscope objective lens 3003 on the object 3016 through a beam splitting element. The beam splitting element consists of an isosceles triangular prism 3006 with an apex angle of 52.5° and a rhomboidal 52.5° prism 3007. Prisms 3006 and 3007 are adjoined along the diagonal surfaces with a gap in between 3009. Gap 3009 is filled with refractive-index-matching, low-acoustic-impedance, nonvolatile liquid. A correction lens 3005 is placed on top of the beam splitting element to compensate for aberrations introduced by the prisms 3006 and 3007, and the acoustic lens 3008. The photoacoustic signal emitted by the object 3016 is transformed by an acoustic lens 3008 into a plane elastic wave in rhomboidal prism 3007. Ultrasonic reflection from the boundary of the prism 3007 converts the incident longitudinal elastic wave into a shear wave. The shear wave propagates toward the free surface of the rhomboidal prism 3007, where it is transformed back into a longitudinal wave and detected by a high-frequency direct-contact ultrasonic transducer 3004 for image formation and spectral measurements of the target 3016.

The fusion of the optical confocal microscopy and photoacoustic microscopy provides complementary information about the object. One feature is the quantitative measurement of the optical absorption spectrum of the object by simultaneously using the fluorescence signal from the optical confocal microscope and the photoacoustic signal from the photoacoustic microscope. The quantitative measurement of the optical absorption spectrum of the object requires knowledge of the spectral variation of the excitation optical fluence at the focus, which may be measured using the fluorescent signals as illustrated below.

In the exemplary embodiment, two excitation optical wavelengths are used. If a fluorescence dye is present, the detected fluorescence signal $V_f(\lambda_{xi}, \lambda_m)$ at the $i^{th}$ excitation wavelength $\lambda_{xi}$ and the emission wavelength $\lambda_m$ is a product of the unknown local excitation optical fluence $F(\lambda_{xi})$, the concentration of dye C, the known molar optical absorption coefficient of the dye $\varepsilon_{af}(\lambda_{xi})$, the quantum yield of the dye Q, and the fluorescence detection sensitivity $S_f(\lambda_m)$. For i=1 and 2, the following ratio in Eqn. (3) is present:

$$\frac{V_f(\lambda_{x1}, \lambda_m)}{V_f(\lambda_{x2}, \lambda_m)} = \frac{\varepsilon_{af}(\lambda_{x1})F(\lambda_{x1})}{\varepsilon_{af}(\lambda_{x2})F(\lambda_{x2})}. \quad \text{Eqn. (3)}$$

Therefore, the local excitation optical fluence ratio may be recovered as in Eqn. (4):

$$\frac{F(\lambda_{x1})}{F(\lambda_{x2})} = \frac{V_f(\lambda_{x1}, \lambda_m)}{V_f(\lambda_{x2}, \lambda_m)} \Big/ \frac{\varepsilon_{af}(\lambda_{x1})}{\varepsilon_{af}(\lambda_{x2})}. \quad \text{Eqn. (4)}$$

Similarly, the detected photoacoustic signal $V_{pa}(\lambda_{xi})$ is a product of the local excitation optical fluence $F(\lambda_{xi})$, the optical absorption coefficient of dominantly absorbing hemoglobin $\mu_{ah}(\lambda_{xi})$, and the acoustic detection sensitivity Sa. Assuming that the hemoglobin absorbs much more than the fluorescent dye, the following ratio in Eqn. (5) is developed:

$$\frac{V_{pa}(\lambda_{x1}, \lambda_m)}{V_{pa}(\lambda_{x2}, \lambda_m)} = \frac{\mu_{ah}(\lambda_{x1})F(\lambda_{x1})}{\mu_{ah}(\lambda_{x2})F(\lambda_{x2})}. \quad \text{Eqn. (5)}$$

From the above two equations, the ratio of the hemoglobin absorption coefficient may be recovered as in Eqn. (6):

$$\frac{\mu_{ah}(\lambda_{x1})}{\mu_{ah}(\lambda_{x2})} = \frac{V_{pa}(\lambda_{x1}, \lambda_m)}{V_{pa}(\lambda_{x2}, \lambda_m)} \frac{V_f(\lambda_{x2}, \lambda_m)}{V_f(\lambda_{x1}, \lambda_m)} \frac{\varepsilon_{af}(\lambda_{x1})}{\varepsilon_{af}(\lambda_{x2})}. \quad \text{Eqn. (6)}$$

This ratio may be used to quantify the oxygen saturation of hemoglobin and the relative total concentration of hemoglobin. Of course, this example merely illustrates the principle, which may be extended to the measurement of other optical absorbers using two or more excitation optical wavelengths.

The presently described embodiments may be used to estimate oxygen metabolism in tissues and organs, by combining measurements of blood flow and oxygenation into and out of regions of interest. Oxygen metabolic rate ($MRO_2$) is the amount of oxygen consumed in a given tissue region per unit time per 100 grams (g) of tissue or of the organ of interest. Since in typical physiological conditions, hemoglobin is the dominant carrier of oxygen, the key measure of blood oxygenation is oxygen saturation of hemoglobin ($sO_2$), as expressed in Eqn. (1) from above.

Exemplary advantages of photoacoustic microscopy over traditional optical and ultrasonic imaging include the detection of endogenous optical absorption contrast at ultrasonic resolution. In photoacoustic microscopy, a pulsed laser beam is focused into the biological tissue to produce emission of ultrasonic waves due to the photoacoustic effect. The short-wavelength pulsed ultrasonic waves are then detected with a focused ultrasonic transducer to form high-resolution tomographic images. Among the existing photoacoustic imaging technologies, the spatial resolutions depend almost solely on the ultrasonic parameters including the center frequency, bandwidth, and numerical aperture (NA). For example, using dark-field confocal PAM, a lateral resolution of approximately 50 µm has been achieved with a center frequency of approximately 50 megahertz (MHz) and an NA of approximately 0.44. This resolution from prior systems is inadequate to resolve smaller structures such as capillaries between approximately 3 µm and approximately 7 µm in diameter with endogenous optical absorption contrast. Aspects of the invention provide improved spatial resolution.

If such an improvement is achieved by increasing the ultrasonic focusing capability, an approximately 5-µm lateral resolution requires an ultrasonic center frequency greater than 300 MHz. At such a high frequency, unfortunately, the ultrasonic attenuation, which is approximately 400 $\mu m^{-1}$ in water and 100 $\mu m^{-1}$ in tissue, limits the penetration depth to approximately 100 µm. An alternative is to use fine optical focusing to provide the lateral resolution while ultrasonic temporal detection provides axial resolution. Such an alternative, called OR-PAM, is primarily sensitive to optical absorption contrast, whereas conventional reflection-mode optical confocal microscopy is dominantly sensitive to scattering or fluorescence.

Figure 31:
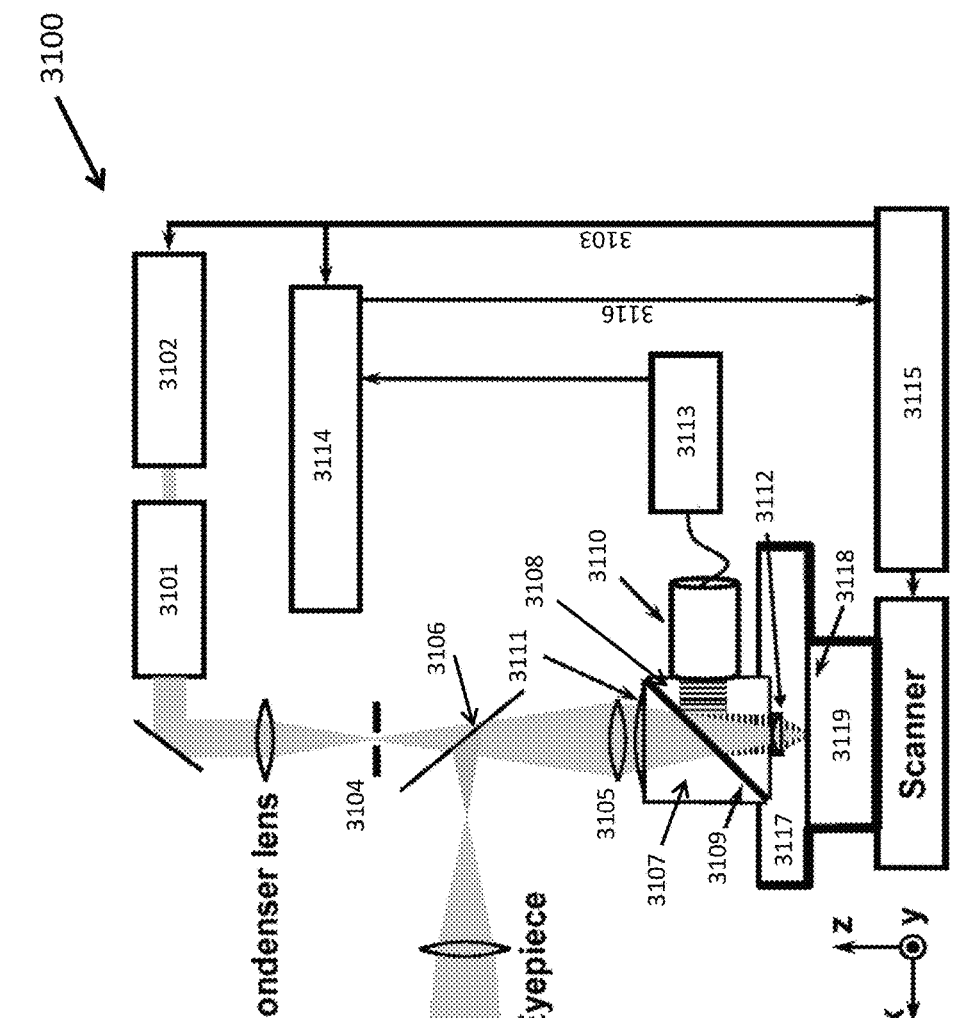
FIG. 31 is a schematic diagram of an eighth photoacoustic sensor that may be used with the imaging system shown in FIG. 22.

FIG. 31 is a schematic of another exemplary embodiment 3100 of the OR-PAM imaging system. In this embodiment, the system employs nearly diffraction limited optical focusing with bright field optical illumination to achieve µm-level lateral resolution. A dye laser 3101, such as a CBR-D laser commercially available from Sirah, pumped by an Nd:YLF pump laser 3102 is used as the irradiation source. The laser pulse duration is approximately 5 ns and the pulse repetition rate, controlled by an external trigger 3103, is as high as 2 kHz. The light from the dye laser 3101 is attenuated by one thousand times, passed through a spatial filter 3104, such as a 25 µm pinhole, commercially available as P250S from Thorlabs, and then focused by a microscope objective lens 3105, such as a RMS4× lens available from Thorlabs and including a NA of approximately 0.1, a focal length of approximately 45 mm, and a working distance of approximately 22 mm. The distance between the pinhole 3104 and the objective lens 3105 is approximately 400 mm. The input aperture of the microscope objective 3105 is approximately 0.8 times the diameter of the Airy disk of the spatial filter 3104. As a result, the diffraction-limited focus of the objective 3105 in water is approximately 3.7 µm in diameter and approximately 200 µm in focal zone. The laser pulse energy after the objective lens 3105 measures approximately 100 nJ. An optional beam splitter 3106 is located between the pinhole 3104 and the objective lens 3105 to facilitate focus adjustment and system alignment. Two right-angled prisms 3107 and 3108, the NT32-545 prism available from Edmund Optics, for example, form a cube with a gap 3109 of approximately 0.1 mm between the hypotenuses. The gap 3109 is filled with silicone oil. As described above, the silicone oil and the glass have a good optical refractive index match but a large acoustic impedance mismatch. As a result, this silicone oil layer is optically transparent but acoustically reflecting. An ultrasonic transducer 3110, such as a V2012-BC transducer available from Panametrics-NDT, with a center frequency of 75 MHz, a bandwidth of 80%, and an active-element diameter of 6.35 mm, is attached to a cathetus of the bottom prism 3108 as shown in FIG. 31. A plano-concave lens 3112 with an approximately 5.2 mm radius of curvature and an approximately 6.35 mm aperture is attached to the bottom of the cube to function as an acoustic lens, which has an NA of approximately 0.46 in water and a focal diameter of approximately 27 µm. Of course, this lens 3112 also functions as a negative optical lens, which is compensated for by a correcting positive optical lens 3111 placed on top of the cube.

The photoacoustic signal detected by the ultrasonic transducer 3110 is amplified by approximately 48 dB using, for example, two ZFL 500LN amplifiers 3113 commercially available from Mini-Circuits, then digitized by a 14-bit digital acquisition board 3114 using, for example, a CompuScope 12400 from Gage Applied Sciences. A raster scanning is controlled by a separate PC 3115, which triggers both the data-acquisition PC 3114 and the pump laser 3102. The trigger signal 3103 is synchronized with the clock-out signal 3116 from the digital acquisition board 3114.

An acoustic lens 3112 is immersed in water inside a heated container 3117. A window is opened at the bottom of the container 3117 and sealed with an ultrasonically and optically transparent 25-μm thick polyethylene membrane 3118. The animal 3119 is placed under the water tank with the region of interest (ROI) exposed below the window 3118. Ultrasonic gel, such as Clear Image, available from SonoTech, is applied to the ROI for acoustic coupling. For simplicity, the raster scanning is implemented by translating the water tank 3117 and the animal 3119 together along the horizontal (x-y) plane. One-dimensional (1D) photoacoustic signal (A-line) at each horizontal location is recorded for 1 μs at a sampling rate of 200 MS/s. A volumetric photoacoustic image is formed by combining the time-resolved photoacoustic signals and may be viewed in direct volumetric rendering, cross-sectional (B-scan) images, or maximum amplitude projection (MAP) images.

FIGS. 32A, 32B, and 32C are images representing a lateral resolution measurement by the imaging system. FIG. 32A is a MAP image of an Air Force resolution test target, FIG. 32B is a magnified image of the region within the dashed box of FIG. 32A, and FIG. 32C is a MAP image of a 6-μm-diameter carbon fiber. The lateral resolution of the OR-PAM system was experimentally measured by imaging an Air Force resolution test target immersed in clear liquid. Images were acquired at the optical wavelength of approximately 590 nm and no signal averaging was performed during data acquisition. In FIGS. 32A and 32B, the highlighted well-resolved bars, shown as group 6, element 5, have gaps of approximately 4.9 μm, a spatial frequency of approximately 102 $mm^{-1}$, and a modulation transfer function value of 0.65. Other pairs of spatial frequency and modulation transfer function values include, for example, a 64 $mm^{-1}$ spatial frequency with a 0.95 modulation transfer function value, and an 80 $mm^{-1}$ spatial frequency with a 0.8 modulation transfer function value. Nonlinearly fitting of the modulation transfer function yields a lateral resolution of approximately 5 μm, which is 30% greater than the diffraction limit of 3.7 μm. As an illustration of the lateral resolution, an MAP image of a 6-μm-diameter carbon fiber immersed in water is shown in FIG. 32C. The mean full-width-at-half-maximum (FWHM) value of the imaged fiber is approximately 9.8 μm, which is 3.8 μm wider than the fiber diameter and hence in agreement with the ~5 μm resolution. The axial resolution was estimated to be approximately 15 μm based on the measured transducer bandwidth, approximately 100 MHz in receiving-only mode, and the speed of sound in tissue, approximately 1.5 mm/μs. In tissue, both the lateral and the axial resolutions deteriorate with imaging depth because of optical scattering and frequency-dependent acoustic attenuation, respectively.

Figures 33A, 33B:
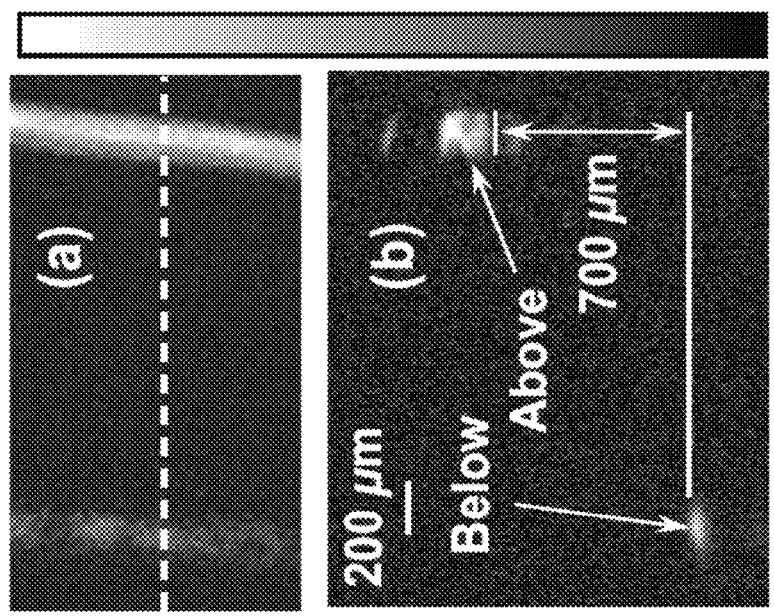
FIGS. 33A and 33B are images representing a measurement of the imaging depth by the imaging system.

FIGS. 33A and 33B are images representing a measurement of the imaging depth by the imaging system. FIG. 33A is a MAP image of two horse hairs placed above and below a piece of rat skin acquired with the OR-PAM system. FIG. 33B is a B-scan image at the location marked by the dashed line in FIG. 33A. The imaging depth of this system was measured by imaging two horse hairs with a diameter of approximately 200 μm placed above and below a piece of freshly harvested rat scalp. A photoacoustic image was acquired with 32 times signal averaging at the optical wavelength of 630 nm. Both hairs are clearly visible, where the bottom hair shows a weaker photoacoustic signal because of both optical and acoustic attenuation in the skin. The B-scan image shows that the bottom hair is 700 μm deep in the tissue. Therefore, the maximum imaging depth is at least 700 μm.

The microvessels in the ear of a nude mouse were imaged in vivo by this OR-PAM at the optical wavelength of 570 nm. Nude mouse ears having a thickness of approximately 300 μm have well-developed vasculature and have been widely used to study tumor angiogenesis and other microvascular diseases. During image acquisition, the animal was kept motionless using a breathing anesthesia system and was kept warm using an infrared lamp. Unlike studies published elsewhere, no optical clearing agent was applied to the skin surface. An area of 1 $mm^2$ was scanned with a step size of approximately 1.25 μm. For each pixel, 16 (i.e., 4 by 4) neighboring A-lines were averaged to increase the signal-to-noise ratio (SNR). The scanning time for a complete volumetric dataset was approximately 18 minutes. After data acquisition, the animal recovered naturally without observable laser damage.

FIGS. 34A and 34B are photoacoustic images of a microvasculature by the imaging system. FIG. 34C is a photograph of the microvasculature of FIGS. 34A and 34B, taken from a transmission microscope. More specifically, FIG. 34A is an in vivo photoacoustic image of microvasculature in a nude mouse ear, FIG. 34B is a 3D visualization of the volumetric photoacoustic data with pseudocolor, and FIG. 34C is a photograph taken with trans-illumination optical microscopy. In FIGS. 34A, 34B, and 34C, the area denoted as C is a capillary, the area denoted as CB is a capillary bed, and the area denoted as SG is a sebaceous gland. The photoacoustic image of the microvasculature (FIGS. 34A and 34B) agrees with the photograph (FIG. 34C) taken from a transmission microscope with a 4× magnification. However, capillaries are imaged by only the OR-PAM system described above. The mean ratio of the photoacoustic amplitudes between the blood vessels and the background is 20:1, which demonstrates a high endogenous optical-absorption-based imaging contrast. Some vessels, e.g. the vessel labeled with C in FIG. 34A, only occupy a single pixel, which presumably indicates a capillary with a diameter of approximately 5 μm. A volumetric rendering of the photoacoustic data (FIG. 34B) shows the three-dimensional connectivity of the blood vessels. Parallel arteriole-venule pairs and their branching are clearly observed. The diameter and the morphological pattern of the vessel within the dashed-box in both FIGS. 34A and 34B suggest that these microvessels belong to a capillary bed. Therefore, OR-PAM, as described above, is able to image capillaries in vivo with endogenous optical absorption contrast due to hemoglobin. In addition, sebaceous glands may also be imaged at the same time.

Figures 35A, 35B:
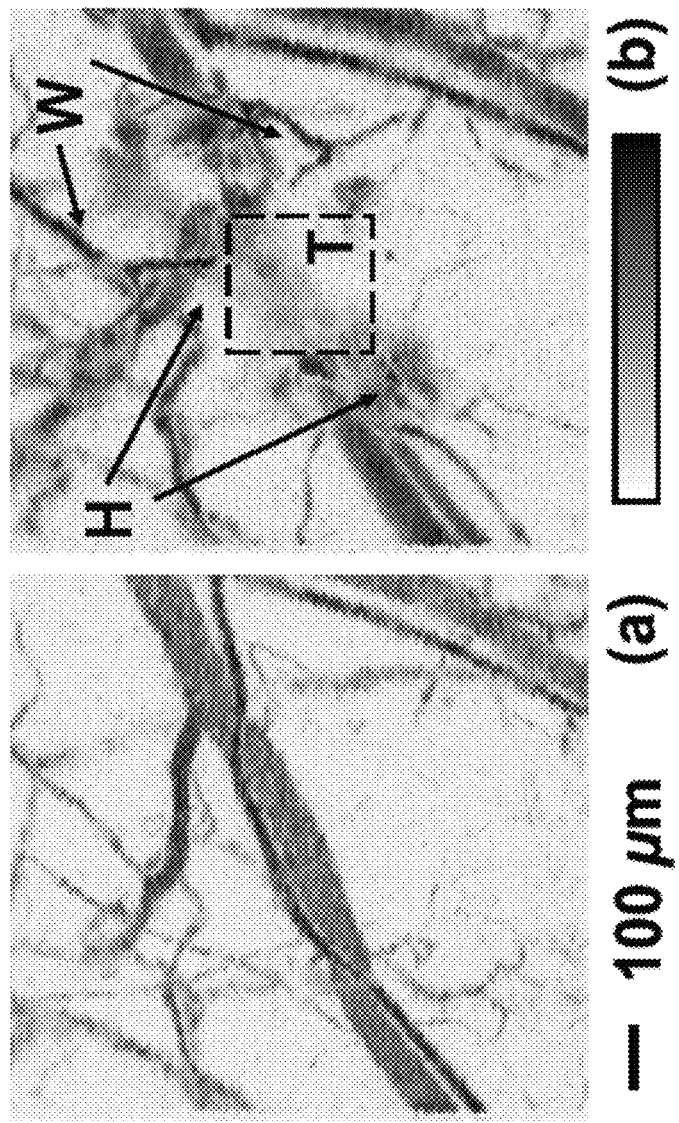
FIGS. 35A and 35B are maximum amplitude projection (MAP) images acquired before (FIG. 34A) and after (FIG. 34B) a high-intensity laser treatment.

FIGS. 35A and 35B are MAP images acquired before and after a high-intensity laser treatment. FIG. 35A is an in vivo photoacoustic image of laser-induced vessel destruction in a Swiss Webster mouse ear before a laser treatment. FIG. 35B is an in vivo photoacoustic image after the laser treatment. In FIGS. 35A and 35B, the area denoted as T is the laser treated area, the area denoted as W is widened blood vessels, and the area denoted as H is a possible hemorrhage. To further demonstrate the potential of OR-PAM, the high-intensity laser destruction of microvessels in the ear of a Swiss Webster mouse were imaged. This type of destruction is clinically used to remove port wine stains in humans. FIGS. 35A and 35B show the MAP images acquired before and after the high-intensity laser treatment. After the healthy vasculature was imaged by the OR-PAM system (shown in FIG. 35A), the center region measuring approximately 0.25×0.25 mm$^2$ was treated by high-intensity laser pulses having a peak optical fluence of approximately 10 J/cm$^2$ scanned with the step size of approximately 1.25 µm. For the high-intensity illumination, the attenuator and the pin hole were removed from the light path. A second image (shown in FIG. 35B) was acquired 15 minutes after the laser treatment. Disruption of the vessels within the treated region was clearly observed in the dashed box. Further, the destruction of the blood vessels dilated several neighboring vessels and produced possibly hemorrhage.

FIG. 36A is an in vivo photoacoustic image of a capillary bed in a mouse ear, captured using the OR-PAM imaging system with a focusing depth of approximately 50 µm. FIG. 36B is an in vivo photoacoustic image of multiple levels of blood vessel bifurcations in a mouse ear, captured using the OR-PAM imaging systems with a focusing depths of approximately 150 µm.

The embodiments described herein use (1) optical focusing to achieve high lateral resolution, (2) time-resolved detection of laser-induced pressure waves to obtain high axial resolution, and/or (3) confocal arrangement between the optical excitation and ultrasonic receiving foci to achieve high sensitivity. In alternative embodiments, the focused ultrasonic receiving may be replaced with optical sensing of the photothermal effect directly inside the object. Three-dimensional images of the distribution of optical contrast within a sampling volume are acquired.

In an existing system, an intensity-modulated continuous-wave beam of radiation is combined with the detection of the magnitude of the photoacoustic signal. In the embodiments described herein, short pulsed excitation is combined with time-resolved detection of the photoacoustic signal, which has the advantage of time-of-flight based axial resolution. Therefore, the presently described embodiments provide, for example, (a) enhanced axial resolution, (b) 3D imaging of optical contrast from a 2D raster scan, and (c) minimal image artifacts due to the interference of photoacoustic waves from various targets within the light illumination volume, in contrast to the existing system.

Another existing system uses focused light to produce thermal expansion and uses optical detection, based on the thermal lens effect, or an ultrasonic detector to monitor the resulting pressure/density transients. Such a system lacks axial resolution. In addition, the lateral resolution of such a system is determined by the detector rather than the excitation optics. Utilization of the thermal lens effect in such a system requires transmission illumination in an optically clear medium, which limits the applications of the technology. Moreover, in using an unfocused ultrasonic transducer and an unfocused ultrasonic detector, the excitation beam has a large separation, which affects the detection sensitivity. The frequency mismatch between the central frequency of the photoacoustic waves (>100 MHz) and the central frequency of the ultrasonic transducer (<10 MHz) also limits the SNR of such a system.

Another existing system uses laser excitation in a coaxial arrangement with a focused ultrasonic detection. However, the laser beam used in such a system is not focused. In fact, the laser beam is divergent because the positive acoustic lens functions as a negative optical lens. The negative optical lens actually broadens the optical beam. More importantly, such a system neither achieves nor claims optically defined lateral resolution, which is a key feature in the presently described embodiments.

The ability to image microstructures such as the microvascular network in the skin or brain cortex and monitor physiological functions of tissue is invaluable. One of the promising technologies for accomplishing this objective is photoacoustic microscopy. Current high-resolution optical imaging techniques, such as optical coherence tomography, can image up to approximately one transport mean free path of between 1 to 2 mm into biological tissues. However, such techniques are sensitive to the backscattering that is related to tissue morphology, and are insensitive to the optical absorption that is related to important biochemical information. Other known techniques such as confocal microscopy and multi-photon microscopy have even more restrictive penetration depth limitation and often involve the introduction of exogenous dyes, which with a few notable exceptions have relatively high toxicity. Acoustic microscopic imaging and spectroscopy systems are sensitive to acoustic impedance variations, which have little functional information about biological tissue and have low contrast in soft tissue. Other imaging techniques such as diffuse optical tomography or thermal wave microscopy have low depth to resolution ratio. Photoacoustic imaging as in embodiments of the invention provides high optical-absorption contrast while maintaining high penetration depth and high ultrasonic resolution. Moreover, because photoacoustic wave magnitude is, within certain bounds, linearly proportional to the optical contrast, optical spectral measurement can be performed to gain functional, i.e., physiological, information such as the local blood oxygenation level. However, increasing the resolution power beyond several tens of micrometers meets serious challenges. At ultrasonic frequencies required to achieve such resolution, which is above approximately 100 MHz, ultrasonic absorption in tissue gradually becomes proportional to the square of the ultrasonic frequency. Consequently, a resolution of several micrometers will have penetration depth of a few tens of micrometers that is much less than the penetration depth of other optical imaging techniques such as confocal microscopy. Embodiments of the present invention overcome the resolution limitation by using optical focusing to achieve high lateral resolution and ultrasonic detection to achieve axial resolution.

Although imaging of photothermal treatment of microvessels itself is biomedically significant, the capability of OR-PAM to image physiological and pathological changes in capillaries has broader applications. Other possible applications include imaging of vasodilation and vasoconstriction in stroke models, tumor angiogenesis, and tumor extravasations. Mouse ears were chosen as the initial organ to test OR-PAM because transmission optical microscopy could be used to validate the photoacoustic images. Since OR-PAM operates in reflection mode, it may be applied to many other anatomical sites.

Several alternative embodiments are possible. First, photoacoustic images may be acquired by scanning the optical-acoustic dual foci instead of the sample and the transducer container. Second, it is possible to scan only the optical focus within the acoustic focusing area to reduce the image acquisition time significantly. Third, by varying the excitation optical wavelength, physiological parameters such as hemoglobin oxygen saturation and blood volume may be quantified for in vivo functional imaging using endogenous contrast. Similarly, targeted exogenous contrast agents such as indocyanine green (ICG) and nanoparticles may be quantified for in vivo molecular imaging. Fourth, the acoustic coupling cube may be made to transmit photoacoustic waves ten times more efficiently without transformation from p-waves into sv-waves so that the SNR may be improved. Acoustic antireflection coating on the lens should further increase the SNR by approximately 10 dB.

When the optical focus is 100 µm below the tissue surface, the surface optical fluence is close to the ANSI safety limit of 20 mJ/cm$^2$ in the visible spectral region. Although the ANSI standards regulate only the surface fluence, the spatial peak optical fluence is calculated at the focus in water, which is approximately 500 mJ/cm$^2$. This focal fluence is still less than the experimentally observed damage threshold in live tissue. After the aforementioned improvements are implemented, the optical fluence may be reduced without affecting the SNR.

It will be understood that particular embodiments described herein are shown by way of illustration and not as limitations of the invention. The principal features in embodiments of this invention may be employed in various embodiments without departing from the scope of the invention. Those skilled in the art will recognize, or be able to ascertain using no more than routine experimentation, numerous equivalents to the procedures described herein. Such equivalents are considered to be within the scope of this invention and are covered by the claims.

All of the compositions and/or methods disclosed and claimed herein may be made and executed without undue experimentation in light of the present disclosure. While embodiments of this invention have been described in terms of preferred embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope and concept of the invention as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine, and/or combination of computing devices), a digital signal processor ("DSP"), an application specific integrated circuit ("ASIC"), a field programmable gate array ("FPGA"), or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

Although embodiments of the present invention have been described in detail, it will be understood by those skilled in the art that various modifications may be made therein without departing from the spirit and scope of the invention as set forth in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

The following examples illustrate various aspects of the disclosure.

Example 1: Quantitative Measurement of Oxygen Release from Single Red Blood Cells In Vivo To demonstrate the measurement of oxygen release from individual RBCs in vivo, the following experiment was conducted. Using a device similar to the single-RBC photoacoustic flowoxigraphy (FOG) device described in FIG. 14, a set of B-scan images were acquired at varied time points, shown in FIG. 15A were obtained to record real-time oxygen delivery as single RBCs flowed from the left to the right side of the field of view. The oxygen release from single RBCs was clearly imaged cell by cell. Taking advantage of the ultra-short wavelength switching time, fast scanning speed, and high spatial resolution, $C_{Hb}$, $sO_2$, $\nabla sO_2$, $V_{flow}$, and $MRO_2$ can simultaneously be quantified from images of single RBCs, as shown in FIG. 15B. By operating a 532-nm single-wavelength laser at a 20-kHz pulse repetition rate, three-dimensional imaging of flowing single RBCs with a 20-Hz rate may be achieved. Other rates may be used.

The ears of nude mice (Hsd:Athymic Nude-FoxlNU, Harlan Co., 4-6 weeks old, 20-25 g of weight) and the brains of white mice (Hsd:ND4 Swiss Webster, Harlan Co., four to six weeks old, 20-25 g of weight) were imaged for all in vivo studies. During imaging, mice were placed on top of a 37° C. heating pad, secured with a head holder, and anaesthetized with isoflurane (Isothesia, Isoflurane USP, Buttler Animal Health Supply). Ultrasound gel was applied between the imaging areas and the water tank. After the ear imaging experiments, the mice naturally recovered. Brain imaging experiments were studied through a small craniotomy. After the brain imaging experiments, the mice were sacrificed via cervical dislocation under deep anesthesia. The laser pulse energy used for the brain imaging was 40-50 nJ usually, and up to 100 nJ when deep RBCs were imaged. To offset skin attenuation, 80 nJ was used when the mouse ear was imaged. Note that the current experimental setup can image capillary segments within a small angle (<10°) from the voice-coil scanning axis (x-axis). For capillaries outside the angular range, either the scanner or the animal was rotated to reduce the angle.

Example 2: Oxygen Delivery Regulated by $V_{flow}$ and $sO_2$ Under Normoxia

In order to study the mechanisms that regulate oxygen delivery, single RBCs in mouse brain capillaries were imaged at a 20-Hz B-scan rate while the mice were breathing air mixed with isoflurane using a device similar to the device used in Ex. 1. Even under normoxia, oxygen delivery fluctuates within a range. The imaged capillaries were 60-150 μm deep from the top surface of the brain cortex, and had segments of 30-60 μm in length within the B-scan window. More than 6000 B-scan images at each wavelength were acquired. Multiple functional parameters from the single RBC images were simultaneously calculated and averaged every 20 B-scans.

FIGS. 15C-15E summarize the relationships among $<sO_2>$, $\nabla sO_2$, $V_{flow}$, and $MRO_2$. In FIG. 15C, it was observed that $MRO_2$ increases with both $\nabla sO_2$ and $V_{flow}$ as expected from Eq. (1). While $\nabla sO_2$ is related to the amount of oxygen released by each RBC, $V_{flow}$ determines the rate of RBCs flowing through the capillary segment. FIG. 15D shows that increasing $MRO_2$ increases $V_{flow}$ if $<sO_2>$ is maintained constant, but decreases $<sO_2>$ if $V_{flow}$ is held constant. From FIGS. 15C and 15D, it was also observed that, for constant $MRO_2$, increasing $V_{flow}$ decreases $\nabla sO_2$ and increases $<sO_2>$. FIG. 15E shows that a decrease of either $V_{flow}$ or $<sO_2>$ is correlated with increasing $\nabla sO_2$.

From these observations, two mechanisms that regulate oxygen release from single RBCs to local tissue under normoxia can be identified. The first one is via $sO_2$ while $V_{flow}$ and $C_{Hb}$ are held constant. When the local tissue consumes more oxygen (i.e., increases the $MRO_2$), $\nabla sO_2$ in the capillary increases; consequently, $<sO_2>$ decreases. The other mechanism is via $V_{flow}$ while $sO_2$ and $C_{Hb}$ are held constant. When the tissue demands more oxygen, it is known that $V_{flow}$ is actively increased so that more RBCs flow through the capillary within a given time period. Because increasing $V_{flow}$ shortens the time for oxygen to diffuse from blood plasma to local tissue, the increasing trend of $\nabla sO_2$ due to the first mechanism is moderated, which allows each RBC to carry oxygen further downstream along the capillary.

Example 3: Dynamic Imaging of Oxygen Delivery Under a Transition from Hypoxia to Hyperoxia Using the device of Ex. 1, the dynamic oxygen delivery process in the mouse ear was imaged under a transition from systemic hypoxia to hyperoxia. Initially, the mouse was breathing in hypoxic gas (5% $O_2$) for over 10 minutes. When the animal reached a stable systemic hypoxic state, the hypoxic gas was altered to pure oxygen, and immediately started at time 0 to acquire B-scan images at 20 Hz along a segment of a capillary. As shown in FIG. 16A, a dramatic increase in single RBC $sO_2$ was observed within 60 seconds. Single-RBC functional parameters, including $<C_{Hb}>$, $<sO_2>$, $\nabla sO_2$, $V_{flow}$, and $MRO_2$, were plotted in FIGS. 16B, 16C, 16D, 16E, and 16F. Each parameter was computed from the images of single RBCs and averaged over every second. Every 10 data points (10 seconds) were grouped for comparison. Statistical tests show that $<C_{Hb}>$, $<sO_2>$, $\nabla sO_2$, and $MRO_2$ increased by 49%±3%, 71%±2%, 96%±7%, and 270%±22%, respectively, but $V_{flow}$ did not change significantly.

In contrast to the correlation in normoxia, the correlation between the $<sO_2>$ and during the transition from hypoxia to hyperoxia is positive. When the inspired gas was switched from low to high oxygen concentration, the capillary $sO_2$ rapidly increased, and the capillary $pO_2$ increased along with the $sO_2$. However, the $pO_2$ in the surrounding tissue changed more slowly than that in blood. As the enhanced radial gradient in $pO_2$ increased oxygen diffusion from capillary blood to tissue, $\nabla sO_2$ was steepened.

Example 4: Glucose-Associated Oxygen Metabolism in the Brain

Figure 17A:
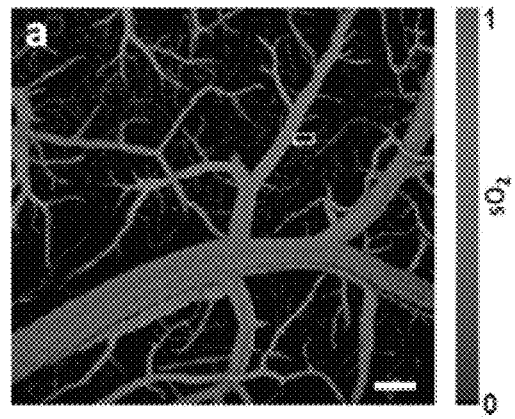
FIG. 17A is a $sO_2$ maximum-amplitude-projection (MAP) image of a mouse brain cortex obtained using a single red blood cell (RBC) photoacoustic flowoxigraphy (FOG) device; the dashed box within the image encloses a capillary segment of interest and the scale bar equals 200 µm.
Figure 17B:
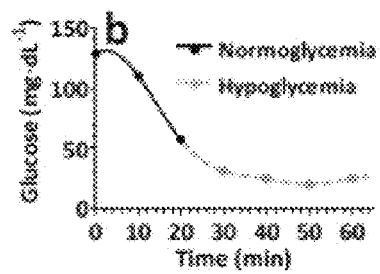
FIG. 17B is a graph summarizing the measured systemic blood glucose level measured every 10 minutes after insulin injection.

The device of Ex. 1 was used to study glucose-associated oxygen metabolism at high resolution. As shown in FIG. 17A, $sO_2$ was imaged over a large field of view in the mouse brain to identify a capillary of interest. Insulin (30 UI per kilogram) was subcutaneously injected into the mouse to induce a systemic decrease in blood glucose. Immediately after the injection, single-RBC functional images were acquired at 100 Hz for over 60 minutes. The blood glucose concentration was measured with a glucose meter (Freestyle Lite, Abbott Diabetes Care Inc.) by drawing blood once every 10 minutes from the mouse tail. FIG. 17B shows the decrease of the blood glucose level with time. FIGS. 17C, 17D, 17E, 17F, and 17G summarize the multiple functional parameters computed from the single-RBC images and averaged over every second. It was observed that the blood glucose level determined the local $MRO_2$. The functional parameters, in particular $MRO_2$ levels, were characterized by striking biphasic responses.

Figure 17C:
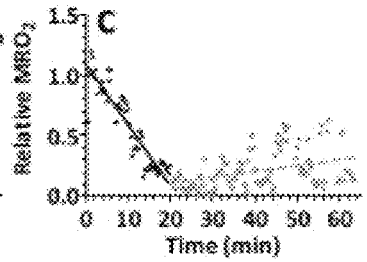
FIGS. 17C, 17D, 17E, 17F, and 17G are graphs summarizing $MRO_2$, $<C_{Hb}>$, $<sO_2>$, $\nabla sO_2$, and $V_{flow}$ quantified from single-RBC images of the capillary segment of interest.
Figure 17D:
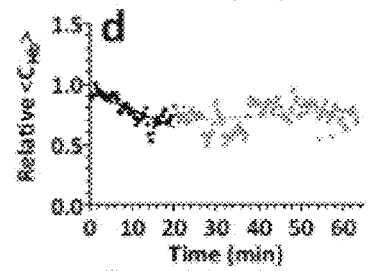
Figure 17E:
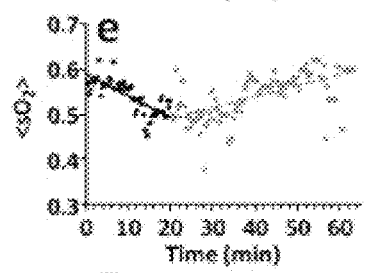
Figure 17F:
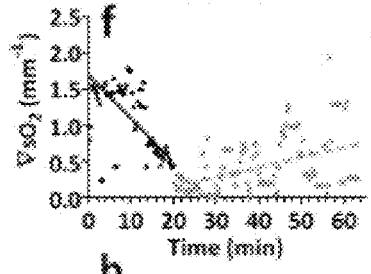

The $MRO_2$ data in FIG. 17C was fitted with a bi-segmental linear regression model according to Eqn. (7):

$$y = \begin{cases} k_1 t + c_1 & \text{if } t \le t_0 \\ k_2(t - t_0) + y_0 & \text{if } t > t_0 \end{cases} \qquad \text{Eqn. (7)}$$

where $y_0 = k_1 t_0 + c_1$, and $t_0$ is the separation time point between the two linear segments. At the fitted $t_0$ equal to 19.6 minutes, the blood glucose concentration is 58.5 mg/dL, which agrees well with the dividing point between normoglycemia and hypoglycemia determined independently. Therefore, the quantitative measurements of glucose concentration, $MRO_2$, $<C_{Hb}>$, $<sO_2>$, $\nabla sO_2$, and $V_{flow}$ were divided into two phases accordingly as illustrated in FIGS. 17B, 17C, 17D, 17E, 17F, and 17G. The first phase was defined as normoglycemia (glucose concentration≥58.5 mg/dL), and the second phase was defined as the hypoglycemia (glucose concentration<58.5 mg/dL). The data of each phase were averaged and fitted to a linear regression model to compare the means and slopes as summarized in FIGS. 17H and 17I.

Figure 17G:
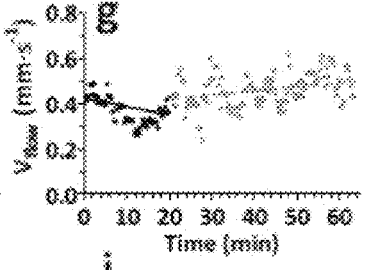
Figure 17H:
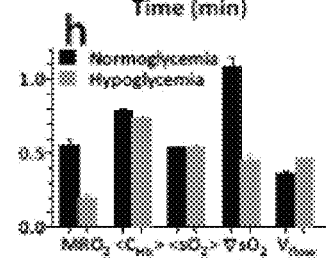
FIG. 17H is a graph comparing average $MRO_2$, $<C_{Hb}>$, $<sO_2>$, $\nabla sO_2$, and $V_{flow}$ during normoglycemia and hypoglycemia; error bars are SEM.
Figure 17I:
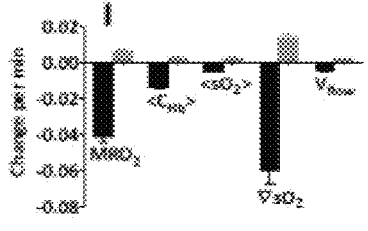
FIG. 17I is a graph comparing the fitted slopes of $MRO_2$, $<C_{Hb}>$, $<sO_2>$, $\nabla sO_2$, and $V_{flow}$ during normoglycemia and hypoglycemia; error bars are SD.

In the normoglycemia phase, $MRO_2$ decreased with the decreasing glucose concentration (FIG. 17C). The other functional parameters including $<C_{Hb}>$, $<sO_2>$, $\nabla sO_2$, and $V_{flow}$ decreased as well. Upon transition from normoglycemia to hypoglycemia, the flow speed was actively increased to compensate for the extremely low glucose metabolism (FIG. 17G). Consequently, $MRO_2$ and the associated functional parameters started to climb.

Example 5: Imaging of Neuron-Single-RBC Coupling

Study of neurovascular coupling has gained broad interest because hemodynamics can be used as an important surrogate to explore neuroscience and study brain disorders. However, existing imaging modalities are limited by either poor spatial resolution or the inability to directly measure $MRO_2$. Here, the device of Ex. 1 was applied to study coupling between visual neural activity and single RBC functions in the brain.

As shown in FIG. 18A, optical stimulation from a bright white LED was applied to the left eye of a white mouse. Target capillaries were imaged in the right visual cortex region of the brain through a craniotomy. FIG. 18B are graphs summarizing transient responses of single RBCs to single visual stimulations (0.5 second flashing). Each functional parameter is first computed from images of single RBCs, and then averaged over one second for 104 trials. Statistical analyses showed that $<sO_2>$, $\nabla sO_2$, $V_{flow}$, and $MRO_2$ changed significantly after visual stimulation, but $<C_{Hb}>$ did not show obvious changes. An increase in flow speed was observed after stimulation, reaching its peak 4-10 seconds after initial stimulation. The single-RBC $<sO_2>$ exhibited a biphasic response: it remained unchanged within 3-5 seconds after stimulation, then proceeded to rise and peaked after 8-10 seconds. The response of $\nabla sO_2$ and $MRO_2$ also showed similar behaviors as $<sO_2>$. This result revealed a clear process of functional hyperemia in the target capillary evoked by visual stimulation.

The coupling between neurons and single RBCs was also imaged under continuous visual stimulation by flashing the LED light at 1 Hz. Capillary segments in the visual cortex region were imaged at 20-100 Hz, varied according to the blood flow speed. FIGS. 18C and 18D show representative $sO_2$ images acquired without and with continuous visual stimulation, respectively. It was found that the $<sO_2>$ decreased after 3 minutes of continuous visual stimulation. The $MRO_2$ was also measured while alternating the continuous visual stimulus on and off. Although the individual data points varied considerably, the mean $MRO_2$ value in each on or off period correlated well with the applied stimulations. All of the single RBC functional parameters, including $<C_{Hb}>$, $<sO_2>$, $\nabla sO_2$, $V_{flow}$, and $MRO_2$, were compared between without and with continuous visual stimulations. Each of the parameters was normalized to its mean value computed from the control images (without stimulation) and plotted as relative values in FIG. 18E. While the $<C_{Hb}>$ did not have significant changes, the $<sO_2>$ decreased by 4%±0.8%, and the $\nabla sO_2$, $V_{flow}$, and $MRO_2$ increased by 53%±6%, 8%±1%, and 56%±9%, respectively.

With the single-RBC resolution, the probability distributions of the single-RBC functional parameters were further quantified. FIGS. 18F, 18G, 18H, and 18I show the cumulative distribution functions (CDFs) of the significantly changed single-RBC functional parameters. With continuous stimulation, it was observed that the single-RBC functions exhibited different distributions from those in the control experiment, i.e., lower $<sO_2>$, higher $\nabla sO_2$, $V_{flow}$, and $MRO_2$, which are consistent with the data shown in FIG. 18E.

It will be understood that the particular embodiments described herein are shown by way of illustration and not as limitations of the invention. The principal features of this invention may be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein may be made and executed without undue experimentation in light of the present disclosure. While the compositions and methods of this invention have been described in terms of embodiments, it will be apparent to those of skill in the art that variations may be applied to the compositions and/or methods and in the operations or in the sequence of operations of the method described herein without departing from the concept, spirit and scope of the invention. All such similar substitutes and modifications apparent to those skilled in the art are deemed to be within the spirit, scope and concept of the invention as defined by the appended claims.

It will be understood by those of skill in the art that information and signals may be represented using any of a variety of different technologies and techniques (e.g., data, instructions, commands. information, signals, bits, symbols, and chips may be represented by voltages. currents, electromagnetic waves, magnetic fields or particles, optical fields or particles, or any combination thereof). Likewise, the various illustrative logical blocks, modules, circuits, and algorithm operations described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, operations of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the invention have been described in detail, it will he understood by those skilled in the art that various modifications may be made therein without departing from the spirit and scope of the invention as set forth in the appended claims.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

What is claimed is:

1. A device for real-time spectral imaging of single moving red blood cells in a subject in vivo, the device comprising:
   an isosbestic laser to deliver a series of isosbestic laser pulses at an isosbestic wavelength;
   a non-isosbestic laser to deliver a series of non-isosbestic laser pulses at a non-isosbestic wavelength;
   an optical fiber to direct the series of isosbestic laser pulses and the series of non-isosbestic laser pulses to an optical assembly;
   the optical assembly to focus the series of isosbestic laser pulses and the series of non-isosbestic laser pulses into a beam with a beam cross-sectional diameter of less than 10 μm through an optical focus region;

a focused ultrasound transducer to detect acoustic signals generated within the optical focus region in response to the series of isosbestic and non-isosbestic laser pulses, the focused ultrasound transducer comprising an acoustic focus region that is aligned with the optical focus region; and an acoustically transparent optical reflector to transmit acoustic signals from the acoustic focus region to the focused ultrasound transducer and to reflect the series of isosbestic and non-isosbestic laser pulses from the optical assembly to the optical focus region;

wherein each isosbestic laser pulse is delivered at a pulse separation period of 20 µs before or after each adjacent non-isosbestic laser pulse.

2. The device of claim 1, wherein: the isosbestic wavelength is a wavelength with a hemoglobin absorbance that corresponds to an oxyhemoglobin absorbance; the isosbestic wavelength is chosen from 532 nm, 548 nm, 568 nm, 587 nm, and 805 nm; and the non-isosbestic wavelength is any wavelength with the hemoglobin absorbance that does not correspond to the oxyhemoglobin absorbance.

3. The device of claim 2, wherein the isosbestic wavelength is 532 nm and the non-isosbestic wavelength is 560 nm.

4. The device of claim 1, wherein the optical assembly comprises a pair of optical lenses comprising two achromatic doublets with a numerical aperture in water of 0.1.

5. The device of claim 1, wherein the focused ultrasound transducer further comprises a central frequency of at least 10 MHz.

6. The device of claim 5, wherein the central frequency is 50 MHz and the focused ultrasound transducer further comprises an axial spatial resolution of 15 µm.

7. The device of claim 5, further comprising a linear scanner to move the optical assembly and the focused ultrasound transducer in a linear scanning pattern.

8. The device of claim 7, wherein the linear scanner is a voice-coil scanner with a scanning rate of at least 100 linear scans per second.

9. The device of claim 1, wherein the acoustically transparent optical reflector comprises a first prism and a second prism, wherein a first face of the first prism and a second face of the second prism are arranged on opposite sides of an aluminum layer forming a planar optical reflector aligned at an angle of 45° relative to an axis of the optical assembly.

10. A system for real-time spectral imaging of single moving red blood cells in a subject in vivo, the system comprising:

a dual wavelength light source module to produce a series of isosbestic laser pulses and a series of non-isosbestic laser pulses at a non-isosbestic wavelength;

an optical module to direct the series of isosbestic laser pulses and the series of non-isosbestic laser pulses through an optical focus region in a cylindrical beam with a beam cross-sectional diameter of less than 10 µm;

an ultrasound detection module to detect acoustic signals generated within the optical focus region in response to the series of isosbestic and non-isosbestic laser pulses, the ultrasound detection module comprising a focused ultrasound transducer, the focused ultrasound transducer comprising an acoustic focus region that is aligned with the optical focus region; and an acoustically transparent optical reflector to transmit acoustic signals from the acoustic focus region to the focused ultrasound transducer and to reflect the series of isosbestic and non-isosbestic laser pulses from the optical module to the optical focus region;

wherein each isosbestic laser pulse is delivered at a pulse separation period of 20 µs before or after each adjacent non-isosbestic laser pulse.

11. The system of claim 10, wherein the dual wavelength light source module comprises an isosbestic laser to produce the series of isosbestic laser pulses and a non-isosbestic laser to produce the series of non-isosbestic laser pulses.

12. The system of claim 10, wherein: the isosbestic wavelength is a wavelength with a hemoglobin absorbance that corresponds to an oxyhemoglobin absorbance; the isosbestic wavelength is chosen from 532 nm, 548 nm, 568 nm, 587 nm, and 805 nm; and the non-isosbestic wavelength is any wavelength with the hemoglobin absorbance that does not correspond to the oxyhemoglobin absorbance.

13. The system of claim 12, wherein the isosbestic wavelength is 532 nm and the non-isosbestic wavelength is 560 nm.

14. The system of claim 10, wherein the optical module comprises an optical fiber operatively connected to the isosbestic laser and the non-isosbestic laser at a first end and operatively connected to a pair of optical lenses comprising two achromatic doublets with a numerical aperture in water of 0.1 at a second end opposite to the first end of the optical fiber.

15. The system of claim 10, wherein the focused ultrasound transducer further comprises a central frequency of 50 MHz.

16. The system of claim 15, further comprising a scanning module to move the optical module and the ultrasound detection module in a linear scanning pattern, wherein the scanning module comprises a voice-coil scanner with a scanning rate of at least 100 linear scans per second.

17. The system of claim 15, wherein the system obtains images of the single moving red blood cells at an axial spatial resolution of 15 µm and a lateral spatial resolution of 3.4 µm.

18. The system of claim 15, wherein the system simultaneously obtains one or more functional parameters of the single moving red blood cells using a pulse oximetry method, wherein the one or more functional parameters are chosen from: total hemoglobin concentration, oxygen saturation, gradient of oxygen saturation, flow speed, metabolic rate of oxygen, and any combination thereof.

* * * * *

UNITED STATES PATENT AND TRADEMARK OFFICE
CERTIFICATE OF CORRECTION

PATENT NO. : 10,433,733 B2
APPLICATION NO. : 15/148685
DATED : October 8, 2019
INVENTOR(S) : Lihong Wang, Lidai Wang and Konstantin Maslov Page 1 of 1

It is certified that error appears in the above-identified patent and that said Letters Patent is hereby corrected as shown below:

In the Specification

Column 1, Lines 37-40, delete "This invention was made with government support under grants R01 EB000712 and R01 NS46214, both awarded by the U.S. National Institutes of Health. The government has certain rights in the invention." and insert therefor --This invention was made with government support under EB000712 and NS046214 awarded by National Institutes of Health. The government has certain rights in the invention.--.

Signed and Sealed this
Thirty-first Day of March, 2020

Andrei Iancu
*Director of the United States Patent and Trademark Office*